(12) United States Patent
Wisniewski et al.

(10) Patent No.: US 11,975,259 B2
(45) Date of Patent: *May 7, 2024

(54) SYSTEMS AND TECHNIQUES FOR GENERATING SCENT

(71) Applicant: OVR Tech, LLC, Burlington, VT (US)

(72) Inventors: Aaron Wisniewski, Burlington, VT (US); Alexander Toulan, Burlington, VT (US); Matthew Flego, Burlington, VT (US); Samuel Wisniewski, Burlington, VT (US); Erik Cooper, Burlington, VT (US); Sarah Socia, Burlington, VT (US)

(73) Assignee: OVR Tech, LLC, Burlington, VT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/833,756

(22) Filed: Jun. 6, 2022

(65) Prior Publication Data

US 2022/0379200 A1 Dec. 1, 2022

Related U.S. Application Data

(63) Continuation of application No. 17/031,509, filed on Sep. 24, 2020, now Pat. No. 11,351,450, which is a
(Continued)

(51) Int. Cl.
*A63F 13/25* (2014.01)
*A61L 9/12* (2006.01)
(Continued)

(52) U.S. Cl.
CPC ............... *A63F 13/25* (2014.09); *A61L 9/122* (2013.01); *A61L 9/125* (2013.01); *A61L 9/14* (2013.01);
(Continued)

(58) Field of Classification Search
CPC .......... A63F 13/25; A63F 13/26; A63F 13/28; A63F 13/50; A63F 13/53; A63F 13/90;
(Continued)

(56) References Cited

U.S. PATENT DOCUMENTS

| 4,952,024 A | 8/1990 | Gale |
| 5,318,503 A | 6/1994 | Lord |

(Continued)

FOREIGN PATENT DOCUMENTS

| CA | 2814977 A1 | 5/2012 |
| CN | 102076387 A | 5/2011 |

(Continued)

OTHER PUBLICATIONS

U.S. Appl. No. 18/154,320, filed Jan. 13, 2023, Flego et al.
(Continued)

*Primary Examiner* — Omkar A Deodhar
(74) *Attorney, Agent, or Firm* — Wolf, Greenfield & Sacks, P.C.

(57) ABSTRACT

Described herein are systems and techniques for generating odor impressions of scents. Some embodiments provide odor impressions in an extended reality (XR) environment (e.g., virtual reality (VR) and/or augmented reality (AR)). The system determines spatial characteristics of an odor impression that is to be generated in the XR environment. The system generates one or more commands for generating the odor impression based on the spatial characteristics. The system transmits the command(s) to a controller for execution. The controller may control dispersal of scented media to generate the odor impression.

21 Claims, 31 Drawing Sheets

Related U.S. Application Data continuation-in-part of application No. 16/871,447, filed on May 11, 2020, now Pat. No. 11,351,449, which is a continuation of application No. 16/219,028, filed on Dec. 13, 2018, now Pat. No. 10,688,389.

(60) Provisional application No. 62/905,916, filed on Sep. 25, 2019, provisional application No. 62/905,936, filed on Sep. 25, 2019, provisional application No. 62/598,357, filed on Dec. 13, 2017.

(51) Int. Cl.
*A61L 9/14* (2006.01)
*A63F 13/52* (2014.01)
*G06F 3/01* (2006.01)

(52) U.S. Cl.
CPC ............... *A63F 13/52* (2014.09); *G06F 3/01* (2013.01); *A61L 2209/111* (2013.01); *A61L 2209/132* (2013.01); *A61L 2209/133* (2013.01); *A63F 2250/021* (2013.01); *A63F 2300/308* (2013.01)

(58) Field of Classification Search
CPC ............ A63F 2250/021; A63F 2250/30; A63F 2300/8082; G06F 3/011
See application file for complete search history.

(56) References Cited

U.S. PATENT DOCUMENTS

| | | |
|---|---|---|
| 5,591,409 A | 1/1997 | Watkins |
| 5,610,674 A | 3/1997 | Martin |
| 5,898,475 A | 4/1999 | Martin |
| 6,231,032 B1 | 5/2001 | Ivey, Jr. |
| 6,296,196 B1 | 10/2001 | Denen et al. |
| 6,371,451 B1 | 4/2002 | Choi |
| 6,713,024 B1 | 3/2004 | Arnell et al. |
| 6,737,025 B2 | 5/2004 | Boyd et al. |
| 7,154,579 B2 | 12/2006 | Selander et al. |
| 7,395,507 B2 | 7/2008 | Robarts et al. |
| 7,584,903 B2 | 9/2009 | Koerner et al. |
| 7,651,077 B1 | 1/2010 | Rosener et al. |
| 7,913,933 B2 | 3/2011 | Van Roemburg |
| 8,012,023 B2 | 9/2011 | Gates, III et al. |
| 8,074,640 B2 | 12/2011 | Davies et al. |
| 8,341,022 B2 | 12/2012 | Edwards |
| 8,706,518 B2 | 4/2014 | Hyde et al. |
| 8,727,234 B2 | 5/2014 | Haran |
| 8,821,802 B2 | 9/2014 | Haran |
| 8,881,999 B2 | 11/2014 | Blaylock et al. |
| 9,283,296 B2 | 3/2016 | Haran et al. |
| 9,289,530 B2 | 3/2016 | Haran et al. |
| 9,446,162 B2 | 9/2016 | Chandler et al. |
| 9,586,228 B2 | 3/2017 | Roemburg et al. |
| 9,648,907 B2 | 5/2017 | Kobal et al. |
| 9,652,037 B2 | 5/2017 | Rubin et al. |
| 9,728,006 B2 | 8/2017 | Varga |
| 9,746,912 B2 | 8/2017 | Meijer et al. |
| 9,755,848 B2 | 9/2017 | Cieszkowski, III et al. |
| 9,811,854 B2 | 11/2017 | Lucido |
| 9,823,473 B2 | 11/2017 | Kobayashi |
| 9,872,968 B2 | 1/2018 | de Zambotti et al. |
| 9,904,358 B2 | 2/2018 | Rubin et al. |
| 9,907,876 B2 | 3/2018 | Jin et al. |
| 10,688,389 B2 | 6/2020 | Flego et al. |
| 11,013,264 B2 | 5/2021 | Sanchez et al. |
| 11,351,449 B2 | 6/2022 | Flego et al. |
| 11,351,450 B2 | 6/2022 | Flego et al. |
| 11,577,268 B2 | 2/2023 | Flego et al. |
| 2002/0129813 A1 | 9/2002 | Litherland et al. |
| 2007/0258849 A1 | 11/2007 | Kent |
| 2008/0092912 A1 | 4/2008 | Robinson et al. |
| 2010/0019057 A1 | 1/2010 | Duru et al. |
| 2011/0045050 A1 | 2/2011 | Elbayoumi et al. |
| 2011/0148607 A1 | 6/2011 | Zeleny |
| 2014/0374503 A1 | 12/2014 | Yoshimura et al. |
| 2015/0038869 A1 | 2/2015 | Simon et al. |
| 2016/0279435 A1 | 9/2016 | Hyde et al. |
| 2016/0296367 A1 | 10/2016 | Ivri |
| 2016/0363280 A1 | 12/2016 | Angelotti |
| 2017/0065000 A1 | 3/2017 | Sears et al. |
| 2017/0112666 A1 | 4/2017 | Fateh |
| 2017/0224938 A1 | 8/2017 | Power et al. |
| 2017/0274279 A1 | 9/2017 | Fateh |
| 2018/0071425 A1 | 3/2018 | Jin et al. |
| 2018/0286351 A1 | 10/2018 | Fateh |
| 2019/0176034 A1 | 6/2019 | Flego et al. |
| 2020/0122182 A1 | 4/2020 | Flego et al. |
| 2020/0330860 A1 | 10/2020 | Flego et al. |
| 2021/0001214 A1 | 1/2021 | Flego et al. |
| 2021/0008446 A1 | 1/2021 | Cooper et al. |
| 2021/0121835 A1 | 4/2021 | Wisniewski et al. |
| 2023/0089379 A1 | 3/2023 | Flego et al. |

FOREIGN PATENT DOCUMENTS

| | | |
|---|---|---|
| CN | 106406548 A | 2/2017 |
| EP | 1598084 A1 | 11/2005 |
| EP | 2 119 465 A1 | 11/2009 |
| JP | 2001-129069 A | 5/2001 |
| JP | 2005-326907 A | 11/2005 |
| JP | 3153624 U | 9/2009 |
| JP | 2014-092673 A | 5/2014 |
| JP | 2018-516719 A | 6/2018 |
| WO | WO 92/05229 A1 | 4/1992 |
| WO | WO 2009/067734 A1 | 6/2009 |
| WO | WO 2014/144690 A2 | 9/2014 |
| WO | WO 2015/143444 A1 | 9/2015 |
| WO | WO 2016/164917 A1 | 10/2016 |
| WO | WO 2016/179167 A1 | 11/2016 |
| WO | WO 2019/035786 A2 | 2/2019 |
| WO | WO 2019/118738 A1 | 6/2019 |

OTHER PUBLICATIONS

Extended European Search Report dated Oct. 26, 2021, in connection with European Application No. 18887380.6.
International Search Report and Written Opinion dated Apr. 5, 2019, in connection with International Application No. PCT/US2018/065476.
International Preliminary Report on Patentability dated Jun. 25, 2020, in connection with International Application No. PCT/US2018/065476.
International Search Report and Written Opinion dated Jan. 14, 2020, in connection with International Application No. PCT/US2019/057023.
International Preliminary Report on Patentability dated Apr. 29, 2021, in connection with International Application No. PCT/US2019/057023.
International Search Report and Written Opinion dated Dec. 17, 2020, in connection with International Application No. PCT/US2020/052543.
International Search Report and Written Opinion dated Dec. 22, 2020, in connection with International Application No. PCT/US2020/052592.
International Search Report and Written Opinion dated Dec. 23, 2020, in connection with International Application No. PCT/US2020/052548.
Ischer et al., How incorporation of scents could enhance immersive virtual experiences. Frontiers in Psychology. Jul. 17, 2014; 5:1-11.
Australian Examination Report dated Oct. 11, 2022, in connection with Australian Application No. 2018383640.
Japanese Office Action dated Oct. 17, 2022, in connection with Japanese Application No. JP 2020-551779.
Decision of Rejection dated Jun. 26, 2023, in connection with Japanese Application No. 2020-551779.

| Proximity | Activity | Duration |
|---|---|---|
| Ambient<br>Burst<br>Specific | Passive<br>Active<br>Invisible<br>Predictive<br>Causal | Burst<br>Sustained<br>Undulating<br>Intervals |

FIG. 6

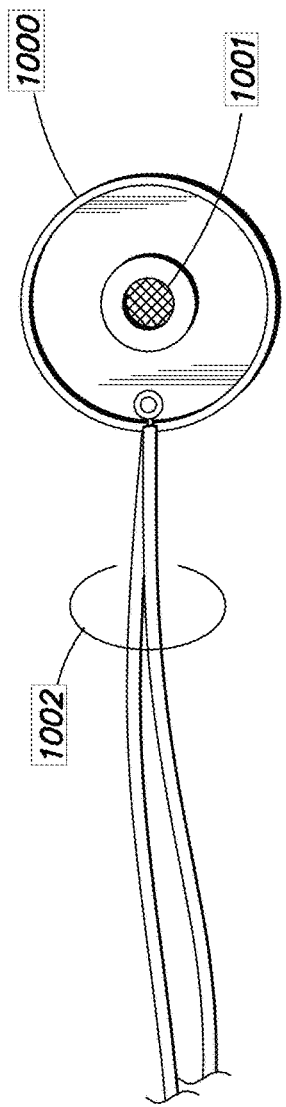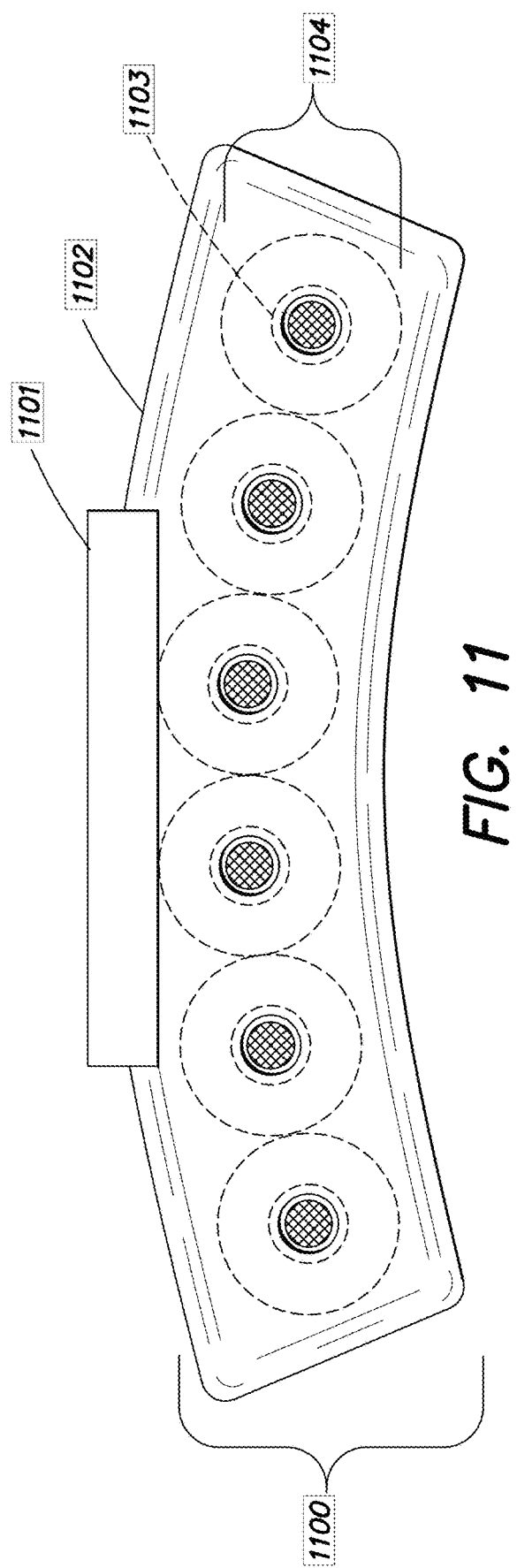

SYSTEMS AND TECHNIQUES FOR GENERATING SCENT

RELATED APPLICATIONS

This Application is a Continuation of U.S. application Ser. No. 17/031,509, filed Sep. 24, 2020, entitled "SYSTEMS AND TECHNIQUES FOR GENERATING SCENT", which is a Continuation-in-part of U.S. application Ser. No. 16/871,447, filed May 11, 2020, entitled "SYSTEM AND METHOD FOR GENERATING OLFACTORY STIMULI", which is a Continuation of U.S. application Ser. No. 16/219,028, filed Dec. 13, 2018, entitled "SYSTEM AND METHOD FOR GENERATING OLFACTORY STIMULI", which is a Non-Provisional of Provisional (35 USC 119(e)) of U.S. Application Ser. No. 62/598,357, filed Dec. 13, 2017, entitled "SYSTEM AND METHOD FOR GENERATING OLFACTORY STIMULI". Application Ser. No. 17/031,509 is a Non-Provisional of Provisional (35 USC 119(e)) of U.S. Application Ser. No. 62/905,916, filed Sep. 25, 2019, entitled "AEROSOL MIXING SYSTEM FOR SCENTED MEDIUM". Application Ser. No. 17/031,509 is a Non-Provisional of Provisional (35 USC 119(e)) of U.S. Application Ser. No. 62/905,936, filed Sep. 25, 2019, entitled "ARCHITECTURE OF SCENT SOFTWARE FRAMEWORK AND API PROCESS". The entire contents of these applications are incorporated herein by reference in their entirety.

FIELD

The present disclosure relates generally to computer-based generation of virtual scent experiences. For example, techniques described herein may be used to create virtual scent experiences in a virtual reality (VR) environment.

BACKGROUND

Virtual reality (VR) provides a computer-generated virtual environment for a user. The user may experience realistic sensations in the virtual environment. VR systems may be implemented on devices such as video game systems and computers. A user may interact in a VR environment through a VR device. For example, a user may view and experience a virtual reality environment through VR goggles.

SUMMARY

The production of scent and human ability to perceive it, interpret it and act upon it is an extremely complex biological mechanism. Human sense of smell is, evolutionarily speaking, the oldest sense and the only one of the senses directly linked to the limbic system of the brain which is the system that is responsible for memory and emotion. Although modern humans rely more heavily on vision than our ancestors, humans' sense of smell it is one of the many senses we have that allow us to understand and navigate the world. But how do we interpret the trillions of scents bombarding us 24 hours a day and make sense of them? According to some aspects, an approach has been developed that simplifies the brain's natural system for interpreting scents and expresses the system into two languages: one for humans, one for computers, and an API that lets them communicate. In some embodiments, there are provided three modalities used to approximate natural human olfaction; proximity-based algorithms, intensity protocol, and a spectrum of odorant appeal. According to some embodiments, a computer system may be programmed to release odorant according to these different modalities.

As described further below, according to some aspects, an architecture of scent (AOS) is provided. As can be appreciated, there are many different ways and methods to classify and categorize odors and odorants and these fall in two primary modalities. The first is biochemical. Odorants act on our bodies in a very predictable manner that can be defined and measured scientifically and empirically. The second is how our brains perceive this biochemical stimulation and the influence it has on our cognition and behavior. At each phase of classification, this behavior is captured in a model. A computer system (e.g., an AR/VR computer system) may be programmed to release scent in a manner consistent with these different modalities. In particular, scent may be released by a computer system at different intensities, times, and in various patterns according to an architecture of scent. In such a system, interfaces (e.g., an API) may be provided to permit an entity to control the release of scent by a computer system to a user.

According to one aspect, a system for generating odor impressions for a user in an extended reality (XR) environment is provided. The system comprises: a processor; a memory storing instructions that, when executed by the processor, cause the processor to perform a scent generating function comprising: determine spatial characteristics of an odor impression that is to be generated in the XR environment; generate at least one command for generating the odor impression based on the spatial characteristics; and transmit the at least one command to a controller, wherein the at least one command, when executed by the controller, causes the controller to generate the odor impression for the user in the XR environment.

According to one embodiment, determining spatial characteristics of the odor impression comprises determining an odorant component in the XR environment. According to one embodiment, the odorant component comprises virtual geometry in the XR environment. According to one embodiment, the virtual geometry is invisible to the user in the XR environment. According to one embodiment, determining spatial characteristics of the odor impression comprises determining one or more dimensions of the virtual geometry; and generating the at least one command comprises determining a scent intensity based on the one or more dimensions of the virtual geometry. According to one embodiment, the odorant component comprises a function for calculating a scalar; and generating the at least one command comprises: using the function to determine the scalar; and determining a scent intensity based on the scalar.

According to one embodiment, determining spatial characteristics of the odor impression comprises determining an indication of scent diffusion direction from a scent generating asset in the XR environment; and generating the at least one command comprises determining a scent intensity based on the indication of scent diffusion direction.

According to one embodiment, determining spatial characteristics of the odor impression comprises determining a measure of proximity of the user to a scent-generating asset in the XR environment; and generating the at least one command comprises determining a scent intensity based on the measure of proximity of the user to the scent-generating asset in the XR environment. According to one embodiment, generating the at least one command for generating the odor impression based on the spatial characteristics comprises: determining, based on the spatial characteristics, a scent intensity to be output to the user; and encoding the scent intensity in the at least one command.

According to one embodiment, generating the at least one command comprises encoding an identification of at least one scent to be output in the at least one command. According to one embodiment, the XR environment comprises an environment of a virtual reality (VR) system, a multimedia system, an entertainment system, a fragrance delivery system, a reactive chemistry system, an advertising system, a medicine delivery system, and/or a skin care system.

According to another aspect, a method for generating odor impressions in an extended reality (XR) environment is provided. The method comprises: using a processor to perform a scent generating function comprising: determining spatial characteristics of an odor impression that is to be generated in the XR environment; generating at least one command for generating the odor impression based on the determined spatial characteristics; and transmitting the at least one command to a controller, wherein the at least one command, when executed by the controller, causes the controller to generate the odor impression for the user in the XR environment.

According to one embodiment, determining spatial characteristics of the odor impression comprises determining an odorant component in the XR environment, wherein the odorant component comprises virtual geometry in the XR environment. According to one embodiment, determining spatial characteristics of the odor impression comprises determining one or more dimensions of the virtual geometry; and generating the at least one command comprises determining a scent intensity based on the one or more dimensions of the virtual geometry.

According to one embodiment, determining spatial characteristics of the odor impression comprises determining a measure of proximity of the user to a scent-generating asset in the XR environment; and generating the at least one command comprises determining a scent intensity based on the measure of proximity of the user to the scent-generating asset. According to one embodiment, determining spatial characteristics of the odor impression comprises determining an indication of scent diffusion direction from a scent generating asset in the XR environment; and generating the at least one command comprises determining a scent intensity based on the indication of scent diffusion direction.

According to another aspect, a computer-readable storage medium for generating odor impressions in an extended reality (XR) environment is provided. The computer-readable storage medium stores instructions that, when executed by a processor, cause the processor to perform a scent generating function comprising: determining spatial characteristics of an odor impression that is to be generated in the XR environment; generating at least one command for generating the odor impression based on the determined spatial characteristics; and transmitting the at least one command to a controller, wherein the at least one command, when executed by the controller, causes the controller to generate the odor impression for the user in the XR environment.

According to another aspect, a system for generating odor impressions is provided. The system comprises; a memory storing instructions; a processor; a plurality of scent generators comprising respective scented mediums; and a controller coupled to the plurality of scent generators; wherein: the instructions, when executed by the processor, cause the processor to perform a scent generating function comprising: generate at least one command for generating an odor impression of a scent; and transmit the at least one command to the controller; and the controller is configured to: control one or more of the plurality of scent generators according to the at least one command to generate the odor impression of the scent.

According to one embodiment, generating the at least one command comprises encoding one or more scent intensities in the at least one command. According to one embodiment, generating the at least one command comprises encoding a duration for each of the one or more scent intensities in the at least one command. According to one embodiment, generating the at least one command comprises encoding an identification of the scent in the at least one command.

According to one embodiment, controlling the one or more of the plurality of scent generators to generate the odor impression comprises: generating one or more control signals for the one or more scent generators according to the at least one command; and inputting the one or more control signals to the one or more scent generators. According to one embodiment, the one or more scent generators comprise at least two scent generators.

According to one embodiment, the controller comprises a driver element configured to translate the at least one command into one or more electrical signals to control the one or more scent generators. According to one embodiment, the plurality of scent generators comprise a plurality of aerosol generators. According to one embodiment, the controller is configured to: store instructions for generating the scent; and control the one or more scent generators to generate the odor impression of the scent by executing the instructions for generating the scent.

According to another aspect, a system is provided. The system comprises: a plurality of aerosol generators, each of which is associated with a different base scented medium; and a controller for interpreting an encoded command, the command identifying a unique odor impression to be rendered, wherein the command includes an identification of a combination of at least two of the plurality of aerosol generators, wherein the controller is configured to translating the command into control signals for activating the at least two of the plurality of aerosol generators to render the unique odor impression.

According to one embodiment, the command includes an identification of a pattern of activation of the at least two of the plurality of aerosol generators. According to one embodiment, the command includes an identification of a duration of activation of the at least two of the plurality of aerosol generators. According to one embodiment, the command includes a unique digital code that identifies the unique odor impression. According to one embodiment, the system further comprises a driver element configured to translate the unique digital code into electrical signals that activate the at least two of the plurality of aerosol generators.

According to one embodiment, the controller is configured to determine a set of unique control signals for activating the plurality of aerosol generators to render a plurality of unique odor impressions that are greater than 1 trillion unique odor impressions. According to one embodiment, the system of claim 1 is part of and/or used in conjunction with at least one of a group comprising: an XR, VR or AR system; a multimedia system and/or application; an entertainment system and/or application; a fragrance delivery system; a reactive chemistry application; an advertising system and/or application; a medicine delivery system; and a skin care system or application.

According to another aspect, a system is provided. The system comprises: one or more scent generators adapted to generate one or more scents to be perceived by a user, the scent generators being capable of being controlled by a computer system; controlling a generation of the one or more scents according to a predetermined architecture of scent function; and providing a computer-based interface that permits the computer system to release the one or more scents responsive to the architecture of scent function.

According to one embodiment, the one or more scent generators are controlled to release scent automatically responsive to actions performed within an AR/VR environment. According to one embodiment, the one or more scent generators are controlled to release scent automatically responsive to a proximity to a scent-generating asset within the AR/VR environment.

According to another aspect, a computer-readable medium storing instructions is provided. The instructions, when executed on by computer, cause the computer to perform a method comprising: providing a computer-based interface to one or more entities, the interface including at least one software function that, when executed, controls a plurality of scent generators to render a desired scent.

According to one embodiment, the computer-based interface further comprises an interface that receives an encoded information identifying a unique scent. According to one embodiment, the method further comprises an act of generating the unique scent, by the plurality of scent generators, responsive to executing the function and receiving of the encoded information.

In some embodiments described above, processes are provided for developing scented media (e.g., liquids) in an architecture of scent. For instance, scented media such as scented liquids may be vaporized by one or more systems. For example, such scented liquids may be vaporized by one or more systems shown and discussed below which show various systems, methods and elements used to vaporize scented liquids in one or more applications.

Historically, there have been many attempts at providing scents in various environments, such as theaters, computer environments, among other situations and locations. However, many of these technologies failed to reach widespread adoption. Also, some attempts have been made to extend scents technology to virtual reality environments, however, it is appreciated that there is no common device available that is capable of rendering scents in such environments. According to some embodiments, a device is provided that is capable of rendering scent stimuli within an augmented and/or virtual reality environment, or any other type of computer-based application.

Such a device, according to some embodiments, may be provided as a companion device or may be fully embedded in an extended reality (XR) (e.g., virtual reality (VR) or augmented/altered reality (AR) headset system (e.g., the well-known HTC Vive, Oculus Rift, Microsoft HoloLens, HTC's Gear VR among other devices and/or systems). The device, may, in some embodiments include a controller (or other type of processor) that is capable of communicating with a game (or content delivery) engine, operating system (e.g., Windows mixed reality, Google daydream) or other type of content delivery processor that produces AR and/or VR content.

In some embodiments, the device, sometimes referred to herein as an OVR (olfactory virtual reality) device or system that provides olfactory stimuli, may include an aerosol generator or AG device for producing vaporized media to render scents. The AG device may include, for example, a piezoelectric vibration device that is used to produce scents corresponding to actions performed in a VR or AR environment. That is, in some implementations, a user interacts with one or more game elements within a game program being executed by the game engine, and responsive to the interaction, the game engine may communicate a series of commands that cause a piezoelectric device of the OVR device to generate scents to be experienced by the user. According to some embodiments, the game engine is coupled to the OVR device via one or more communication channels such as a wireless interface (e.g., Bluetooth, WiFi, etc.). The game engine (or other type of content producer) may communicate with the OVR device using a stream of serial data, which when received by the OVR device, may be translated to scent commands that operate one or more piezoelectric elements of the OVR device.

In some embodiments, the OVR device further includes one or more detachable elements (e.g., a vessel or other element type) that each contain a scent module. The detachable scent modules may, in some embodiments, include one or more scents that can be controlled by the game engine. There could be any number of small scent modules, each associated with a separate piezoelectric element that can be addressed and used to render a scent to the user. The scent modules may be constructed using an element that contains one or more scents, which can be in the form of liquid, gel or solid scent media.

In some embodiments, the microcontroller or other processor type controls an amplitude of a piezoelectric device which in turn controls airflow that interacts with a corresponding detachable scent module. The volume of scent delivered to the user's olfactory organs are controlled more accurately using such a control. Also, in some embodiments, a larger range of rendered scent strengths may be produced as a result.

In some embodiments, there may be one or more stages of piezo elements used to render scent information. As discussed further below, some elements may be used to provide fine control of the outputs of specific scents, while other elements may be used to perform primarily airflow movement, alone or in addition to fan elements or other air moving devices. In some embodiments, the piezo elements may or may not have separate vessels that contain the scent media. In some instances, the piezo elements may come preloaded with scent media. Some types of piezo elements may provide a replaceable form of scent media, such as a wick, insert or other media-containing element. In some embodiments, the piezo driven device vibrates liquid through a fine mesh to an output an aerosol or other atomized output to the user's nose.

The piezo driven aerosol generator (AG) may take many forms, such as devices using vibrating mesh technology (VMT). For example, a ring-shaped piezo device formed around a plate with aperture holes having specified sizes may be used to vibrate a liquid into a fine mist that is dispersed in the air surrounding a user's nose. Such plates may be, in some embodiments, flat or formed (domed). In some embodiments and application types, the size of the holes may be less than 10 microns.

Other piezo-type devices may be used, such as tubes of various shapes and sizes that have a piezo element surface attached to a tube surface, and which is arranged to vibrate and force the liquid into a mist through an aperture plate having holes. It should be appreciated that other arrangements and types of piezo elements may be used.

In some embodiments, an arrangement of piezo elements (e.g., an array) may be used to provide scent information to a user. Such arrangements may be directly addressable via a controller or other device to control each of the piezo elements. Some embodiments use an array of piezo elements positioned near the nose to provide scent output directly to the user.

In some embodiments, a chamber may be formed near or around the user's nose to permit the user to receive the outputs of the piezo elements. The chamber may be formed, for example, using a housing that substantially surrounds the user's nose and that directs outputs of the piezo elements towards the user's nose. In some embodiments, the housing may be adapted to be mounted to an underside of an existing headset device.

According to some embodiments, the device includes a plurality of piezoelectric elements that are capable of being operated within a number of variable states. Such states may be controlled by a processor such as a microcontroller. The piezoelectric elements may operate as pumps that can be used to drive scents within channels that can be positioned near the user's nose. In some embodiments, these channels may be configured in a variety of configurations using, for example, tubes or conduit, air reservoirs, vessels, and other physical constructs to obtain a system that disperses sent into or near the user's nose.

As discussed, the OVR device may include a processor and a serial input that receives an output provided by the game engine or other computing entity (e.g., other programs, systems, etc.). In some embodiments, an application programming interface (API) may be provided as a programmatic interface by which games and other external programs may be used to control and deliver scent information. By transmitting certain sequences of commands, the OVR device may be capable of delivering a scent output by controlling delivery of the variety of scented medium contained within the vessels. The variety of scented medium can be dispersed singularly or in combination to achieve a realistic sense of an object or environment. In some embodiments, the vessels can be designed to contain the different scented media in liquid, solid or even gel form. The vessels may also contain certain functionality or identifiers that allow them to be identified to the OVR system (e.g., what type of scent, level of media, etc.). In some embodiments, different combinations of vessels may be associated with different game formats. In some embodiments, each vessel is intended to be changed out when the scented media is depleted.

As discussed above, the device, according to some embodiments, may be provided as a companion device or may be fully embedded in a Virtual Reality (VR) or Altered Reality (AR) headset system. According to some embodiments, coupling devices are provided to attach the OVR device to various headset systems, such that outputs of the OVR device are positioned near the user's nose. In other embodiments, the OVR device features may be fully incorporated within the headset system. In one implementation of a fully integrated system, commands used to control OVR functions are integrated within the headset inputs provided by the game engine. In other embodiments, it is appreciated that such an OVR device may be integrated with other inputs and outputs, such as blood pressure monitors, haptic feedback devices, heartrate monitors, eye movement monitors or other devices.

In some embodiments, an atomizer is provided for dispensing liquids into the air. In some implementations, a device is provided for generating atomized fluid specifically, but not exclusively, for production of small droplets of scented oil and other fluid-based fragrances, among other types of liquids. In some embodiments, the device comprises a tube having a proximal opening and a distal opening, wherein media inside the tube is forced out of the proximal opening via an aperture plate.

In some embodiments, the tube further includes at least one piezoelectric element (e.g., a plate) that is attached to a face of the tube. The device further includes an aperture plate that is attached to the proximal end of the tube whereas the distal end of the tube is connected to a fluid supply source for supplying fluid through the tube to aperture plate at the proximal end of the tube. In some embodiments, the aperture plate includes a plurality of conical apertures that extend through the thickness of the plate.

In some embodiments, the device comprises a tube having a proximal opening and a distal opening, wherein fluid enters the distal end and is forced out of the proximal opening via an aperture plate. In some embodiments, fluid may be existing within the tube and/or added via the distal end, such as by a mechanism to add fluid as the device operates and forces the fluid out. In some embodiments, the device is provided with the fluid located within the tube.

According to at least one aspect, a system is provided comprising a processor, at least one piezoelectric element controllably coupled to the processor, one or more scented media, and an interface adapted to receive one or more commands from an external content processor, wherein the processor is configured to, responsive to the received one or more commands, control the at least one piezoelectric element to deliver an output scent using the one or more scented media.

In some embodiments, the system further comprises one or more vessels that contain respective ones of the one or more scented media. In some embodiments, the one or more vessels each includes a corresponding piezoelectric element that are controllably coupled to the processor. In some embodiments, the one or more commands includes at least one command that selectively controls an identified piezoelectric element to render a specific scent. In some embodiments, the one or more command includes a plurality of commands that selectively control more than one piezoelectric element to render a blended scent.

In some embodiments, the system further comprises a programmable interface through which the external content processor may control the at least one piezoelectric element. In some embodiments, the one or more commands each specified a duration and intensity value associated with a respective scent. In some embodiments, the system further comprises a housing, the housing comprising a physical coupling to a headset capable of being worn by a user.

In some embodiments, the system includes hardware that delivers an olfactory output to the user, wherein the physical coupling positions the olfactory output of the system proximate to the user's nose. In some embodiments, the processor, the at least one piezoelectric element, the one or more scented media and the interface are part of a VR or AR device. In some embodiments, the one or more vessels that contain respective ones of the one or more scented media are detachable from the system.

In some embodiments, the commands from an external content processor are communicated responsive to an interaction of a user in an AR or VR realm. In some embodiments, the external content processor communicates proximity information to the system responsive to the user's interaction with one or more elements in the AR or VR realm.

In some embodiments, the at least one piezoelectric element comprises a tube having a proximal opening and a distal opening, an aperture element coupled to the proximal opening of the tube, the aperture element having at least one aperture, a piezoelectric element attached to a surface of the tube, the piezoelectric element adapted to receive an electrical signal that causes the piezoelectric element to vibrate and induce a wave along a length of the tube that forces a medium through the at least one aperture. In some embodiments, the tube is at least one of a cross-sectional shape of a square, a triangle, a polygon, a rectangle and a circle. In some embodiments, the tube is adapted to receive the medium through the distal opening. In some embodiments, the medium includes at least one of a solid, a liquid and a gel. In some embodiments, the tube is adapted to receive a wick element that delivers a liquid medium to be dispersed. In some embodiments, the piezoelectric element forms a unimorph element with the tube.

According to some aspects, a computer-implemented method is provided comprising acts of receiving, via an interface of a scent generating device, a data element defining at least one scent to be rendered, processing, by a processor coupled to the interface, the received data element, controlling, responsive to processing the received data element, at least one piezoelectric element to deliver an output scent identified by the received data element. In some embodiments, the scent rendering device includes a plurality of scented media, and wherein the received data element uniquely identifies the output scent among the plurality of scented media to be rendered.

In some embodiments, the data element forms a stream of data, and the method further comprises an act of processing a received stream of data, the stream of data defining a plurality of scents to be rendered. In some embodiments, the a data element defining the at least one scent to be rendered defines a duration and an intensity value associated with the at least one scent to be rendered, and wherein the method further comprises controlling, responsive to processing the received data element, at least one piezoelectric element to deliver an output scent responsive to the defined duration and an intensity value associated with the at least one scent to be rendered. In some embodiments, the data element defining the at least one scent to be rendered defines a start command, and wherein the method further comprises an act of processing, by the processor responsive to the start command, one or more scent rendering commands defined by the data element.

Still other aspects, examples, and advantages of these exemplary aspects and examples, are discussed in detail below. Moreover, it is to be understood that both the foregoing information and the following detailed description are merely illustrative examples of various aspects and examples, and are intended to provide an overview or framework for understanding the nature and character of the claimed aspects and examples. Any example disclosed herein may be combined with any other example in any manner consistent with at least one of the objects, aims, and needs disclosed herein, and references to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example.

BRIEF DESCRIPTION OF DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of a particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. In the figures:

FIG. 6 shows example scent classification information that may be used according to various aspects;

FIG. 10 shows an example device that may be used to render scent according to some embodiments;

FIG. 11 shows an example device that may use one or more devices to render various scents according to some embodiments;

DETAILED DESCRIPTION

Figure 1:
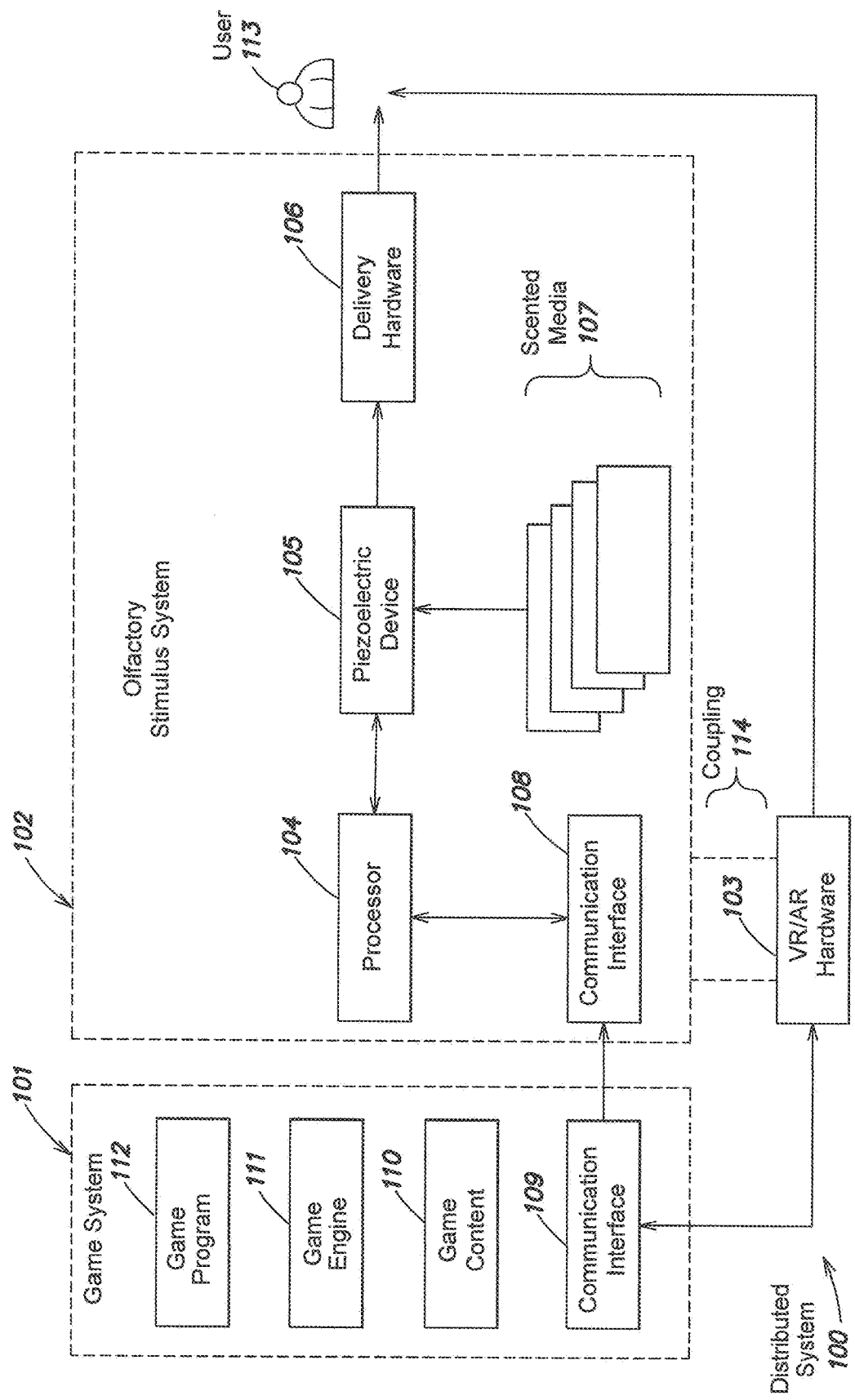
FIG. 1 shows a block diagram of a distributed computer system capable of implementing various aspects.

The inventors have recognized that the human sense of smell is an essential mechanism through which humans experience the world. For example, in a computer-generated extended reality (XR) environment (e.g., a virtual reality (VR) environment), the sense of smell may be a mechanism through which a user experiences the XR reality. The inventors have further recognized that production of scent and human perception of scent are complex biological mechanisms. Conventional techniques for creating scent experiences may not reflect how scent is produced nor how humans perceive scent. For example, conventional techniques of creating scent experiences may not accurately model how scent is dispersed in an environment, nor how a human would experience the scent in the environment. As a result, an XR system employing conventional techniques may not provide users with a realistic experience.

Accordingly, the inventors have developed systems and techniques for generating scent experiences that more closely reflect physical production of scent and human perception of scent. A generated scent experience may be referred to herein as an "odor impression". Described herein are techniques of computer-based generation of odor impressions. For example, techniques described herein may be implemented in an XR system (e.g., a VR system) to provide users with realistic experiences of scent in an XR environment (e.g., a virtual reality). The computer-based techniques described herein may be referred to as "architecture of scent (AOS)."

In embodiments of techniques described herein, a computer system may determine spatial characteristics of an odor impression that is to be generated (e.g., in an XR environment). For example, the system may (1) identify a scent generating asset in a virtual reality environment; and (2) determine spatial characteristics of an odor impression that provides a scent experience from the scent generating asset. The system may generate a command for generating the odor impression based on the determined spatial characteristics. The system may transmit the command to a controller. The command, when executed by the controller, may cause the controller to disperse scented media according to the command to generate the odor expression.

In some embodiments, the system may determine spatial characteristics of an odor impression to be rendered (e.g., in an XR environment) by determining one or more odorant components that are to be generated in the XR environment for the scent generating asset. An odorant component may comprise virtual geometry that represents scent from the scent generating asset in the XR environment. The virtual geometry may provide a computerized model of scent in the XR environment. The system uses the virtual geometry to generate an odor expression for a user.

Describes herein are embodiments of a system for generating odor impressions. The system includes multiple scent generators (e.g., aerosol generators) that have respective scented mediums. The system may include a controller that may control the scent generators to generate (e.g., render) odor impressions. The system may generate one or more commands for generating an odor impression of a scent. The system transmits the generated command(s) to the controller. The controller controls one or more of the scent generators according to the command(s) to generate the odor impression of the scent. The system may generate an odor impression of a scent by controlling multiple scent generators to disperse multiple scented mediums that, when experienced by a user (e.g., at the user's olfactory epithelium), may render the odor impression of the scent. For example, the combination of a first and second scents of the disperse scented mediums may result in an odor impression of the scent.

According to some implementations, a system is provided that is capable of rendering scent information to a user. For instance, it is appreciated that are no adequate commercially-available devices capable of rendering scent information in an AR or VR environment. In particular, according to some embodiments, it is appreciated that it would be beneficial to have a device that could be used with existing AR or VR headsets to render scent information to a user. Such scent information may be rendered by a game engine responsive to activities performed or experienced within the AR or VR realm. In other embodiments, such functionality may be incorporated within such headset devices.

FIG. 1 shows a block diagram of a distributed computer system 100 capable of implementing various aspects. In particular, distributed system 100 includes a game system 101, and olfactory stimulus system 102, and optional separate VR/AR hardware 103. The combination of the olfactory stimulus system 102 (and optionally the VR/AR hardware 103) may be used to communicate information to a user 113. Although the olfactory stimulus system 102 is shown separate from the game system 101 in the example embodiment of FIG. 1, in some embodiment, components of the olfactory stimulus system 102 and game system 101 may be shared. For example, software components (e.g., the architecture of scent software framework) of the olfactory stimulus system 102 may be implemented as part of the game system 101.

Game system 101 may be any suitable computer system. As shown in the example of FIG. 1, the game system 101 includes a game program 112, a game engine 111, game content 110, and a communication interface 109. Game system 101 may use the game engine 111 which may include for example, any processors, code, and development platform used to write game programs (e.g., game program 112). Notably, according to various embodiments, game programs 112 may include interface through which they can communicate with the olfactory stimulus system 102. Such interfaces may include, for instance, an application programming interface (API) that defines commands and data structures for controlling the olfactory stimulus system 102. Further, game system 101 may include one or more communication interfaces 109 which can be used to communicate to system 102. Such interfaces may include, for example, wired or wireless communication interfaces.

In some embodiments, the game engine 111 may generate game content 110. For example, the game engine 111 may use the game program 112 to generate the game content 110. In some embodiments, the game content 110 may include information about a game being played by the user 113. In one example, the game content 110 may include information about an XR environment (e.g., a virtual reality) that is generated by the game engine 111. The game content 110 may include information about objects and/or actions occurring in the XR environment. For example, the game content 110 may include information identifying objects in the XR environment, movement in the XR environment (e.g., by the user and/or other objects therein), a position of the user 113 in the XR environment, and/or other information. In some embodiments the game system 101 may be configured to communicate information from the game content 110 to the olfactory system 102 (e.g., for use in generating odor impressions in a game).

As shown in the example of FIG. 1, the game system 101 includes a communication interface 109. The communication interface 109 may be used by the game system 101 to communicate with the olfactory stimulus system 102. In some embodiments, the communication interface 109 may comprise hardware for communicating with the olfactory stimulus system 102. For example, the communication interface 109 may comprise a network interface device for communicating with the olfactory system 102. In some embodiments, the communication interface 109 may comprise a software interface for communicating with the olfactory stimulus system 102. For example, the communication interface 109 may be an application program interface (API) for communicating with a software component of the olfactory stimulus system 102. The API may include one or more methods, classes, and/or properties for use by the game system 101 to communicate with the olfactory stimulus system 102. In some embodiments, the game system 101 may use the communication interface 109 to transmit information to the olfactory stimulus system 102. The game system 101 may use the communication interface 109 to obtain (e.g., receive) information from the olfactory stimulus system 102.

In some embodiments, the olfactory stimulus system 102 may include a software framework that is used by the game system 101 for indicating scent (e.g., in an XR environment). The software framework may also be referred to herein as architecture of scent framework. For example, the architecture of scent framework may be added to the game engine 111 of the game system 101. As an illustrative example, the game engine 111 may be the Unity game engine developed by Unity Technologies. The architecture of scent framework may be added as a plugin to the Unity game engine to provide the game engine with a mechanism to represent scent in an environment (e.g., an XR environment) generated by the game engine 111.

In some embodiments, the olfactory stimulus system 102 may provide odorant components for use in the game system 101. The odorant components are computer-based representations of scent that may be used by the olfactory stimulus system 102 to generate odor impressions. In some embodiments, the olfactory stimulus system 102 may provide a set of predefined odorant components that may be used by the game system 101. Each of the odorant components may represent different types of scent dispersal. For example, a first odorant component may represent ambient scent in an environment, while a second odorant component may represent a burst of scent (e.g., when a user first smells garbage). Examples of odorant components are described herein with reference to FIGS. 24A-28B. In some embodiments, the odorant components may be provided as software objects that can be used by software code of the game system 101. For example, each odorant component may be class that can be used to instantiate an object by software code of the game system 101. The game system 101 may use the odorant components to generate a virtual representation of scent in an XR environment. For example, the game system 101 may include software code that instantiates odorant component software objects for scent generating assets in the XR environment.

In some embodiments, an odorant component may comprise virtual geometry that spatially represent scent in an XR environment. Different odorant components may have different geometry. For example, a first odorant component may have spherical geometry, and a second odorant component may have cone geometry. Examples of geometry of various odorant components are described herein with reference to FIGS. 24A-28B. In some embodiments, an odorant component may comprise one or more parameters. The parameter(s) may include geometric dimensions, maximum scent intensity, scalar functions, effusion rate, rate of decay, and/or scent identification.

In some embodiments, the olfactory stimulus system 102 may generate odor impressions for a user. The odor impression may provide the user with a scent experience while the user is interacting with an XR environment provided by the game system 101. In some embodiments, the olfactory stimulus system 102 may generate an odor impression by determining spatial characteristics of the odor impression. The olfactory system 102 may determine spatial characteristics of the odor impression by determining odorant components in the XR environment (e.g., generated by software code of the game system 101 using an architecture of scent framework provided by the olfactory stimulus system 102). The olfactory stimulus system 102 may obtain (e.g., from the game system 101) an indication of one or more odorant components in the XR environment. The olfactory stimulus system 102 may use the indication of the odorant component(s) to determine spatial characteristics of the odor expression. For example, the olfactory stimulus system 102 may determine a spatial region in which scent is to be experienced according to geometry of an odorant component. The olfactory stimulus system 102 may generate an odor impression based on a user's interaction with the geometry. The olfactory stimulus system 102 may use parameter(s) of the odorant component (e.g., geometric dimensions, effusion rate, and/or other parameters) to generate the odor impression.

As an illustrative example, a user may smell a flower in an XR environment. An odorant component may be output in the XR environment representing scent from the flower. The olfactory stimulus system 102 may determine spatial characteristics of an odor expression to be generated to create an experience of scent for the flower. The olfactory stimulus system 102 may determine the spatial characteristics from the odorant component output by the game engine 111. The spatial characteristics may include a region in which the scent is experienced, and direction of scent dispersal.

In some embodiments, the olfactory stimulus system 102 may determine spatial characteristics of an odor impression by determining a measure of proximity of a user to scent-generating asset(s) in an XR environment. A user may be represented in the XR environment by an olfactory epithelium object (also referred to herein as "olfactory epithelium"). The olfactory epithelium may represent a user's nose in the XR environment. The olfactory stimulus system 102 may generate an odor impression using the measure of proximity of the user to a scent generating asset. In some embodiments, the measure of proximity may be a distance between the user and the scent-generating asset in the XR environment. In some embodiments, the olfactory stimulus system 102 may determine scent intensity by determining a location of the user in relation to virtual geometry of one or more odorant components. For example, the olfactory stimulus system 102 may determine a distance of the user from a surface of the virtual geometry. As another example, the olfactory stimulus system 102 may determine an angle of the user relative to the virtual geometry.

In some embodiments, the olfactory stimulus system 102 may generate an odor impression by determining an intensity of one or more scents to be dispersed. The olfactory stimulus system 102 may determine the intensity of the scent(s) to generate an odor impression having the determined spatial characteristics. For example, the olfactory stimulus system 102 may determine an intensity of a scent by determining (1) whether the user is within the boundary of virtual geometry of an odorant component; and/or (2) a position of the user relative to dimensions of the virtual geometry. The system may determine whether the user is within the boundary of virtual geometry using a measure of proximity of the user to a scent generating asset that the virtual geometry is associated with. Examples of how the olfactory stimulus system 102 may determine intensity of scent(s) are described herein with reference to FIGS. 24A-28B.

In some embodiments, the olfactory stimulus system 102 may generate one or more commands to generate an odor impression having the determined spatial characteristics. The olfactory stimulus system 102 may transmit the command(s) to a controller (e.g., processor 104) configured to control the piezoelectric device 105 for execution (e.g., to control dispersal of scented media 107 using the delivery hardware 106). In some embodiments, the olfactory stimulus system 102 may generate the command(s) by encoding one or more intensity values for one or more scents to be output (e.g., using delivery hardware 106) in a command. The olfactory stimulus system 102 may encode the intensity value(s) in a command data structure. For example, the intensity value(s) may be encoded in a message that is to be sent to the controller. The olfactory stimulus system 102 may encode an identification of a scent to be outputted as indicated by the encoded intensity value(s). In some embodiments, the olfactory stimulus system 102 may encode one or more durations for the intensity value(s) in the command(s). For example, the olfactory stimulus system 102 may encode a duration for each intensity value. Example command data structures are described herein.

In some embodiments, the olfactory stimulus system 102 may transmit commands to a controller (e.g., processor 104). The command(s), when executed by the controller, cause the controller to control the piezoelectric device 105 to disperse one or more scented mediums of the scented media 107 via the delivery hardware 106.

As illustrated in the example of FIG. 1, olfactory stimulus system 102 includes a processor 104 that controls operation of system 102 components. In some embodiments, the processor 104 may be a component of a controller. Olfactory stimulus system 102 includes one or more piezoelectric devices (e.g., piezoelectric device 105) which control the delivery of one or more types of scented media 107 for the purpose of rendering scent information to the user (e.g., user 113). Piezoelectric device 105 may deliver an olfactory output via the delivery hardware 106. For example, the piezoelectric device 105 may cause the delivery hardware 106 to disperse one or more scented mediums.

In some embodiments, the processor 104 may obtain a command for generating an odor impression of a scent. The processor 104 may obtaining data including a command data structure (e.g., via communication interface 108). In some embodiments, the processor 104 may obtain the command from a software component of the olfactory stimulus system 102. For example, the software component may be plugged into the game engine 111 of the game system 101. The processor 104 may obtain the command from the software component via the communication interface 108. The processor 104 may execute the obtained command. In some embodiments, the processor 104 may execute the command by controlling one or more of multiple scent generators (e.g., aerosol generators) to disperse scented media of the scent generator(s) and generate the odor impression of the scent. The processor 104 may control the scent generator(s) by (1) generating one or more control signals for controlling the scent generator(s) according to the command; and (2) inputting the generated control signal(s) to the scent generator(s). For example, the processor 104 may translate intensity value(s) and duration(s) encoded in the command into electrical signal(s) which are input to the scent generator(s).

As shown in the example embodiment of FIG. 1, the olfactory stimulus system 102 includes a piezoelectric device 105. The piezoelectric device 105 may include one or more scent generators. Each of the scent generator(s) may include a respective scented medium from the scented media 107. A scene generator may include vessels, interconnecting tubes, reservoirs, venturi elements, inlets, outlets, channels and/or any other active or passive delivery mechanisms. A scent generator may disperse its scented medium (e.g., by a control signal from the controller). For example, the scent generator may be an aerosol generator that is used by the piezoelectric device 105 to release scented medium.

In some embodiments, a controller may control the piezoelectric device 105 to generate an odor impression. The controller may control the scent generator(s) (e.g., using piezoelectric device 105) by executing a command. For example, the olfactory stimulus system 102 may generate a command that, when executed by the controller, causes the controller to use the piezoelectric device 105 to disperse scented media according to the command. By executing the command, the olfactory stimulus system 102 may generate an odor impression having particular spatial characteristics (e.g., determined by the olfactory stimulus system 102 from odorant components). In some embodiments, a command may indicate intensity and duration for one or more scents. The controller may use the piezoelectric device 105 to release the indicated scent(s) with the indicated intensity and duration.

As shown in the example embodiment of FIG. 1, the olfactory stimulus system 102 includes delivery hardware 106. The delivery hardware 106 may be hardware for delivering scented media (e.g., dispersed by the piezoelectric device 105) to the user 113. The delivery hardware 106 may deliver scented media to a nasal cavity of the user 113. For example, the delivery hardware 106 may deliver scented media to the olfactory epithelium inside the nasal cavity of the user 113. Examples of delivery hardware and scented media are described herein.

In some embodiments, the olfactory stimulus system 102 may generate an odor impression of a scent by controlling multiple scent generators to release multiple scented mediums. A controller of the olfactory stimulus system 102 (e.g., processor 104) may control multiple scent generators to release the multiple scented mediums. The multiple scented mediums may each have a respective scent. The combination of the multiple scents, when experienced by a user (e.g., olfactory epithelium of the user), may generate the odor impression of the scent. The olfactory stimulus system 102 may thus generate scents by mixing scents provided by scented media 107 of the scent generators.

In some embodiments, the controller may store instructions for generating a scent. The controller may generate an odor impression of the scent by executing the instructions. For example, the instructions may indicate an activation of multiple different scent generators for generating the odor impression of the scent. In some embodiments, the instructions may indicate a function for activating a scent. For example, the instructions may indicate that a mildew scent is to be preceded by a scent of moisture, followed by the mildew scent. In some embodiments, the controller may store instructions for multiple different scents, where instructions for a respective scent indicate a function for activating the scent. In some embodiments, the controller may execute instructions for a scent in response to obtaining a command indicating an odor impression of the scent.

As shown in the example of FIG. 1, the olfactory stimulus system 102 includes a communication interface 108. The communication interface 108 may be used by the olfactory stimulus system 102 to communicate with the game system 101. In some embodiments, the communication interface 108 may comprise hardware for communicating with the game system 101. For example, the communication interface 108 may comprise a network interface device for communicating with the game system 101. In some embodiments, the communication interface 108 may comprise a software interface for communicating with the game system 101. For example, the communication interface 108 may be an application program interface (API) for communicating with the game system 101. The API may include one or more methods, classes, and/or properties for use by software of the olfactory system 102 to communicate with the game system 101. In some embodiments, the olfactory stimulus system 102 may use the communication interface 108 to transmit information to the game system 101. For example, the olfactory stimulus system 102 may use the communication interface 108 to transmit one or more queries for information to the game system 101. The olfactory stimulus system 102 may obtain information from the game system 101 using the communication interface 108. For example, the olfactory stimulus system 102 may receive information from the game content 110 of the game system 101 through the communication interface 108. For example, the olfactory stimulus system 102 may obtain data indicating odorant components in the XR environment.

In some embodiments, hardware components the olfactory stimulus system 102 may be provided as part of an existing headset device. In some embodiments, the olfactory stimulus system 102 may be provided as an additional device for existing VR/AR hardware (e.g., hardware 103). To accomplish this, a physical coupling 114 may be provided such that the olfactory stimulus system 102 is positioned such that scent outputs may be provided to a user (e.g., user 113).

Although the example of FIG. 1 shows the components of the olfactory system 102 distinct from other systems, some embodiments are not limited in this respect. In some embodiments, components of the olfactory stimulus system 102 may be shared among other components in the distributed system 100. In some embodiments, the processor 104 may be a component of the game system 101 in addition to or instead of the olfactory system 102. For example, the processor 104 may be configured to execute instructions for the olfactory stimulus system 102 and the game system 101. In some embodiments, the olfactory system 102 may be embedded as part of the game system 101. For example, software of the olfactory stimulus (e.g., architecture of scent framework) system 102 may be embedded in the game engine 111 (e.g., as a plugin).

According to one embodiment, processor 104 may include a specially programmed microcontroller that performs certain specified control functions. One example of a specific control processor and circuitry is shown by way of example in FIG. 5 discussed below. In some embodiments, the microcontroller (MCU) may include an ATmega328p Arduino-type controller. It should be appreciated, however, that other controller types may be used. Further, the microcontroller may also include some additional auxiliary components such as a frequency generator, digital potentiometer and one or more operational amplifiers which may be used to adjust voltage into a variable amplitude fixed frequency current that can be used to control a piezoelectric element. In some embodiments, the processor 104 may be any computer hardware processor. For example, the processor 104 may be a central processing unit (CPU) of a computer. Some embodiments are not limited to any processor described herein.

Although the olfactory stimulus system 102 of FIG. 1 is shown in conjunction with a game system 101, some embodiments are not limited in this respect. In some embodiments, the olfactory stimulus system 102 may be used with other types of systems and/or in other applications. A software component of the olfactory stimulus system 102 may be embedded in other systems and/or applications. For example, software functionality of the olfactory stimulus system 102 described herein may be embedded in the systems. Hardware components of the olfactory stimulus system 102 may be adapted for and/or coupled to other systems.

In some embodiments, the olfactory stimulus system 102 may be used with any XR system. For example, the olfactory stimulus system 102 may be used with an augmented reality (AR) system of a mobile device. In some embodiments, the olfactory stimulus system 102 may be used with a multimedia system. For example, the olfactory stimulus system 102 may be used with a home theater system. In some embodiments, the olfactory stimulus system 102 may be used with a fragrance delivery system. For example, the olfactory stimulus system 102 may be used with a system for delivering fragrances in a home. In some embodiments, the olfactory stimulus system 102 may be used with a reactive chemistry application. For example, the olfactory stimulus system 102 may provide scent experiences resulting from chemical reactions. In some embodiments, the olfactory stimulus system 102 may be used with an advertising system. For example, the system 102 may provide scent experiences as part of advertisements provided by the advertisement system. In some embodiments, the system 102 may be used with a medicine delivery system. For example, the system 102 may be used to deliver medicine via a user's nose (e.g., to be inhaled by the user). In some embodiments, the system 102 may be used with a skin care system. For example, the system 102 may be used to disperse scent for skin care applications.

Figure 2:
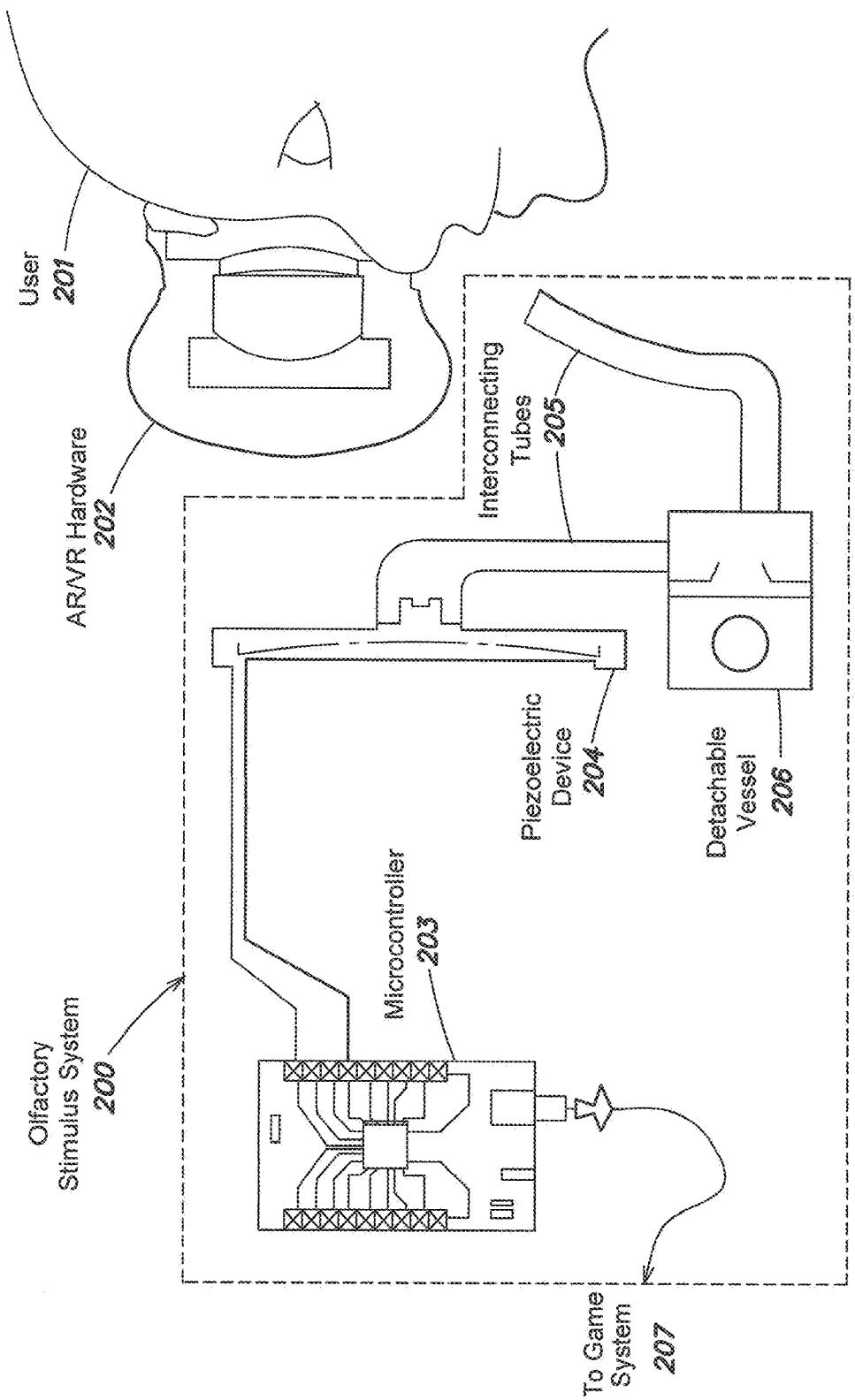
FIG. 2 shows an example olfactory stimulus system according to some embodiments.
Figure 3:
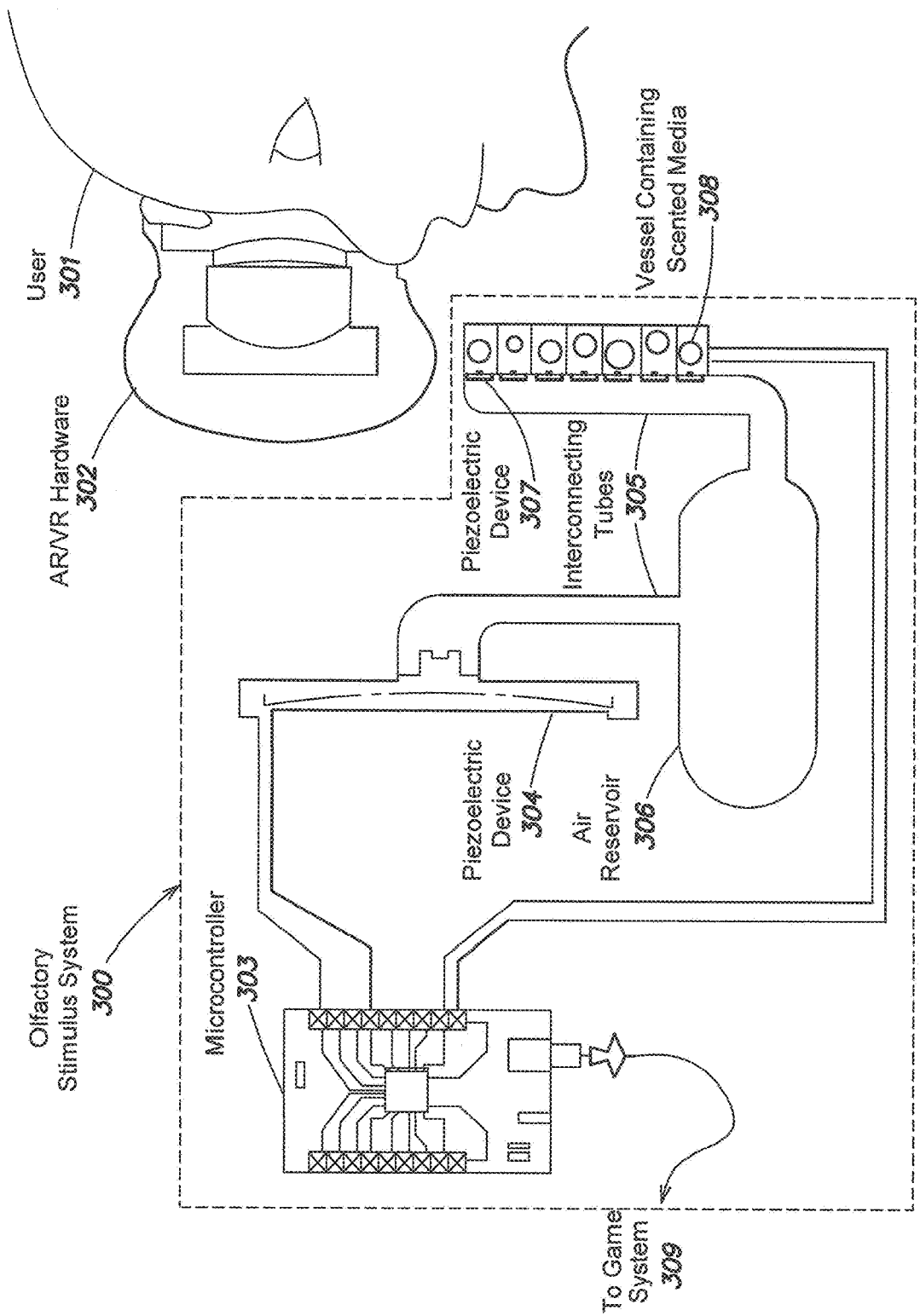
FIG. 3 shows another example olfactory stimulus system according to some embodiments.

FIGS. 2 and 3 show various implementations of olfactory stimulus systems according to some embodiments. In particular, FIG. 2 shows an olfactory stimulus system 200 which can be used with existing AR/VR hardware 202 to present scent information to user 201. System 200 includes a microcontroller 203 that controls a piezoelectric device 204. The piezoelectric device 204 acts as a pump which blows air passed a detachable vessel 206 which contains scent media. Air and/or scent particles are routed between elements using one or more channels such as those provided by interconnecting tubes 205.

According to some embodiments, piezoelectric components may be used to move air and possibly diffuse liquids into a channel. Channels may be constructed using tubes manufactured using chemically resistant materials (e.g., brass or some other material). In some embodiments there may be manufactured using chemically resistant materials to counter the effects of water and possibly mild amounts of alcohol present within the scented media. According to some embodiments, such channel elements may be internally molded and/or printed elements.

Detachable vessel 206 (among other elements and embodiments described herein) may also be made from chemically resistant materials (e.g., glass, Plastic (PTFE, PEEK, UHMW, PTE, possibly HDPE chemically resistant variants), stainless steel, or other material(s) either alone or in combination with other materials).

Further, microcontroller 203 may be coupled to a game system 207 via one or more interfaces (e.g., a communication interface such as a wired or wireless connection (e.g., Bluetooth, Wi-Fi, or other type wireless communication protocol)).

FIG. 3 shows an alternative configuration of an olfactory stimulus system 300. In particular, similar to system 200, FIG. 3 shows an olfactory stimulus system 300 which can be used with existing AR/VR hardware 302 to present scent information to user 301. Similarly, olfactory stimulus system 300 may include a microcontroller 3031 or more piezoelectric devices (e.g. devices 304, 307) interfaces to a game system (e.g., game system 309), and one or more channel elements including reservoirs (e.g., air reservoir 306), tubes (e.g. interconnecting tubes 305), vessels (e.g. one or more vessels containing scented media 308) among other items. Notably, the system may have a two-stage design where there are smaller piezoelectric elements provided in addition to a main piezoelectric element that provide the majority of air movement.

Notably, in an alternative configuration shown in FIG. 3, separate piezoelectric devices are provided for specific vessels that contain various scented media. The microcontroller may be selectively controlled to activate certain piezoelectric devices to control delivery of particular scented media. As discussed further below, commands that specifically address particular piezoelectric devices may be provided such that the game system may control delivery of particular scents. In some embodiments, different vessels contain different scents. In one implementation, vessels may contain active logic that communicate their information (e.g., what scents they contain, status, level of media, etc.) with microcontroller 303. Also, in some implementations, collections of vessels or individual vessels may be removed and/or replaced when they are exhausted. Air reservoir 306 may be provided such that air pressure may be stored in controlled and selectively delivered to individual vessels to provide a rendered output.

Figure 4:
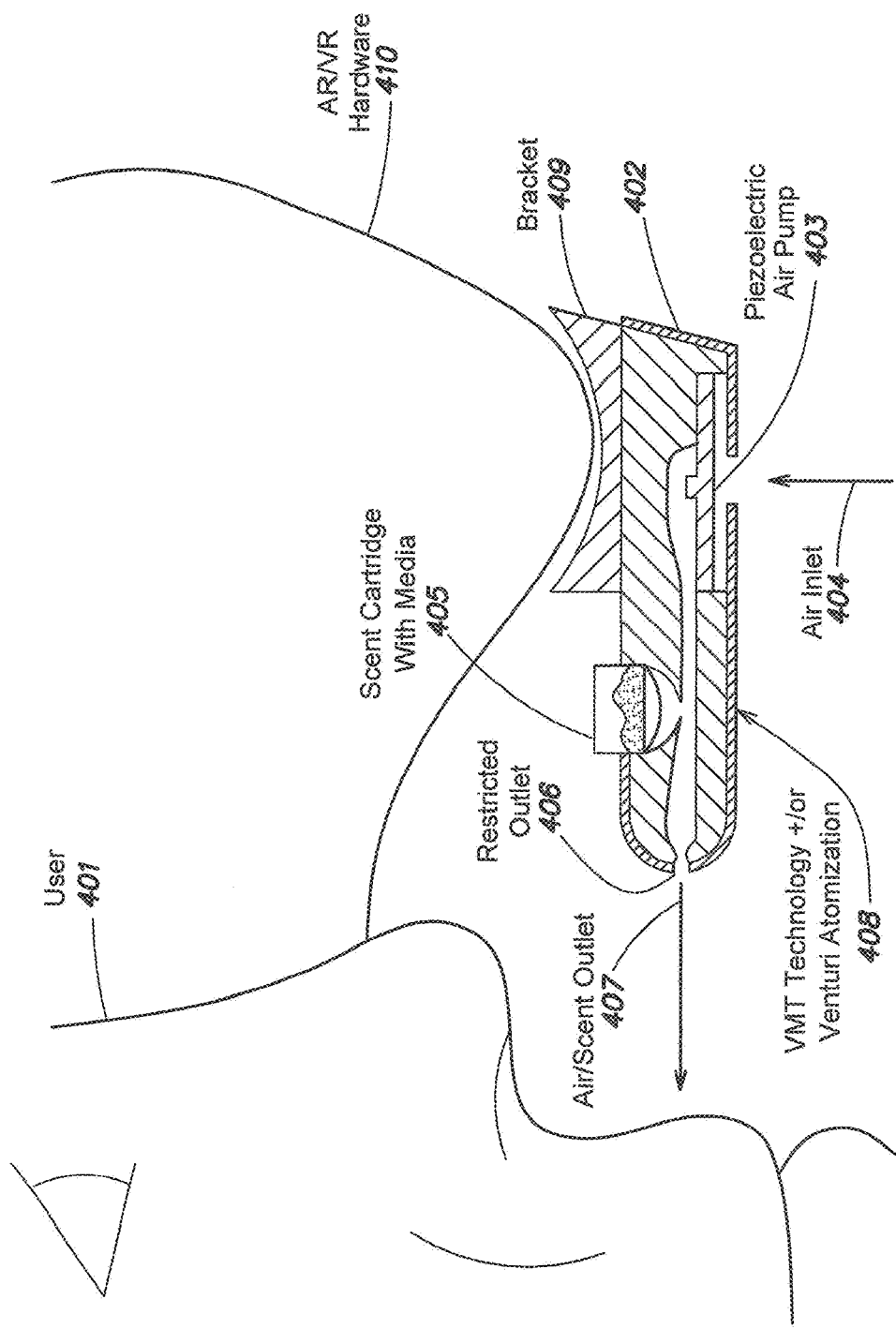
FIG. 4 shows an example olfactory stimulus system physical configuration according to various embodiments.

FIG. 4 shows another example device configuration 402 that may be used alone or in connection with other embodiments. For instance, as shown in FIG. 4, element 402 is connected to existing AR/VR hardware for 10 via a physical bracket 409. Notably, the position of element 402 may be adjusted so that an olfactory output (e.g., air/scent outlet 407) may be positioned near a user's nose (e.g., the nose of user 401). In the configuration shown in FIG. 4, element 402 includes an air inlet 404 a restricted outlet 406 a piezoelectric air pump 403 and venturi technology (e.g., an atomizer nozzle). In particular, the piezoelectric air pump 403 operates to pump air from an air inlet 404 within the chamber which mixes with an output of a scent cartridge having media (e.g., cartridge 405) in the mixture is pumped through a restricted outlet 406 to the nose of the user (e.g. user 401).

Figure 5:
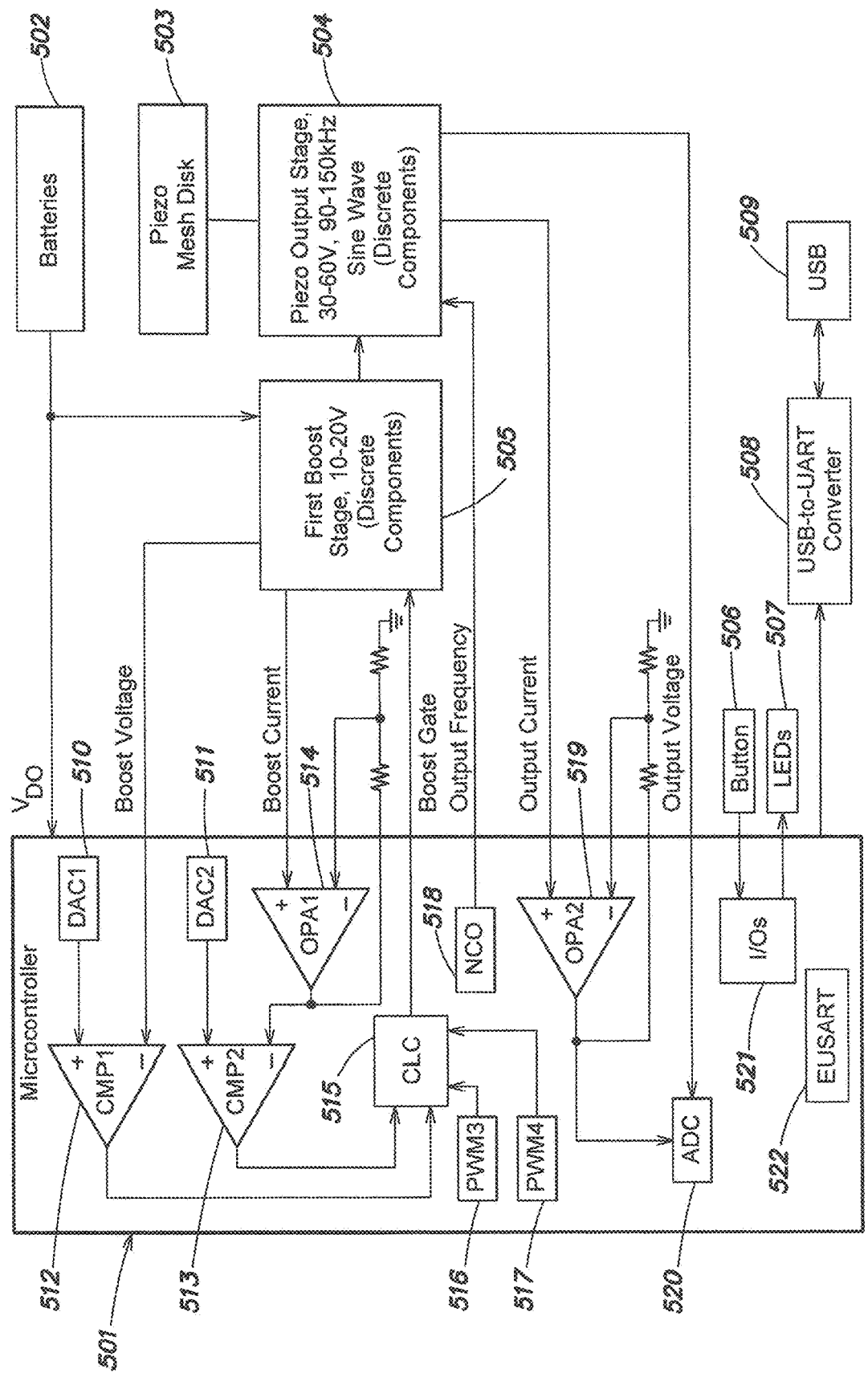
FIG. 5 shows an example control system according to various embodiments.

FIG. 5 shows an example circuit in control function circuitry used to implement various aspects. For instance, a microcontroller 501 may be provided which includes one or more digital to analog converters (e.g., elements 510, 511) one or more comparators (e.g. comparators 512, 513), operational amplifiers (e.g. operational amplifiers 514, 519). Among other elements. As discussed above, the circuit may be used to boost current and voltage and output gate frequency to operate a piezoelectric output stage (e.g., 504) which in turn controls a piezo mesh disk (e.g., element 503) which renders the scented output.

Microcontroller 501 may include one or more I/O ports to communicate information and receive information from various elements (e.g. button 506, LEDs 507). Further, microcontroller may include an element (e.g., EUSART 522) to communicate serial data to outside elements (e.g., such as by converting serially formed UART data to a USB output using a USB-to-UART converter 508 and USB interface 509). Also, in some embodiments, the device may operate on its own power supply which could include batteries (e.g., batteries 502) or some other power input.

Various embodiments may relate to ways of representing scent information in a distributed system, and encoding and decoding such information. FIG. 6 shows one example implementation including example scent classification information that may be used for communicating scent information in a distributed communication network. It is appreciated that smell architecture may be of great importance when it comes to creating a realistic experience, especially in an AR/VR environment such as those provided in virtual reality, altered reality or telecommunication devices using headsets or other devices.

According to various embodiments shown by way of example in table 600, various types of information may be used to classify or qualify scent information. In particular, a particular scent may include proximity information 601, activity information 602, duration information 603, and appeal information 604.

Proximity

In one implementation, proximity information may be used to express how close the user or player is to an odorant object (e.g., within an AR/VR environment). An odorant object may also be referred to herein as a "scent generating asset." In one embodiment, the proximity settings dictate whether a smell is "on" or "off". Proximity information may include one or more of the following.

Ambient (e.g., the foundation)—The overall smell of a particular environment meant to set an emotional tone.

Burst (e.g., walls, floors, lighting, furniture)—The smell of an object or collection of objects noticeable when passing within a particular distance (e.g., 1 meter).

Specific (e.g., appliances)—The smell of a specific object noticeable only when less than or equal to a distance (e.g., 12 inches) from a user's face.

Activity

In one implementation, activity information may be used to express the level of conscious interaction the player is having with the odorant object. It is appreciated that the level of conscious interaction is not necessarily directly linked to the proximity of the player to the object, but generally speaking, the activity may be proportionate. Activity information may include one or more of the following.

Passive—Smells that are activated by passing by an object that is not necessarily interactable but plays a role in creating ambience or foreshadowing in the narrative. A burst may be a passive smell.

Active—When the player interacts with an object deliberately. For example, the player may interact either for curiosity or to gain information/solve a puzzle.

Invisible—Smell that is only released upon performing a specific action like opening a bottle or drawer. In some embodiments, this characteristic may allow for circumventing the standard proximity protocols.

Predictive—Predictive smells are ones that come on the breeze around a corner or from behind a closed door. They may be predictive (fire/smoke) or ever changing to promote a sense of doom.

Causal—The effect when the user takes an exaggerated breath in.

Duration

In one implementation, duration information may be used to express how long is the smell being activated for in the hardware. Duration information may include one or more of the following.

Burst—A burst will generally be a release of a predetermined time (e.g., 1 second) of a single or series of heavily diffusive aromas. Navigating through the VR environment will also be navigating through different bursts. The pockets of scent experienced in succession through space and time will create an aromatic tapestry potentially as rich as the visual one.

Sustained—A slow continuous release of scent to either block outside odor or create subconscious reaction. In some embodiments, the scent may be very faint.

Undulating—A single smell meant to me experienced over a longer period of time. In some embodiments, due to the "habituating effect" of the olfactory system it may be necessary to increase and decrease intensity in a set predictable manner.

Intervals—A way to mimic smell intensity by modulating rapid microbursts.

It should be appreciated that other types of encoding scent information may be used, and some embodiments may use different types of encoding.

Figure 7:
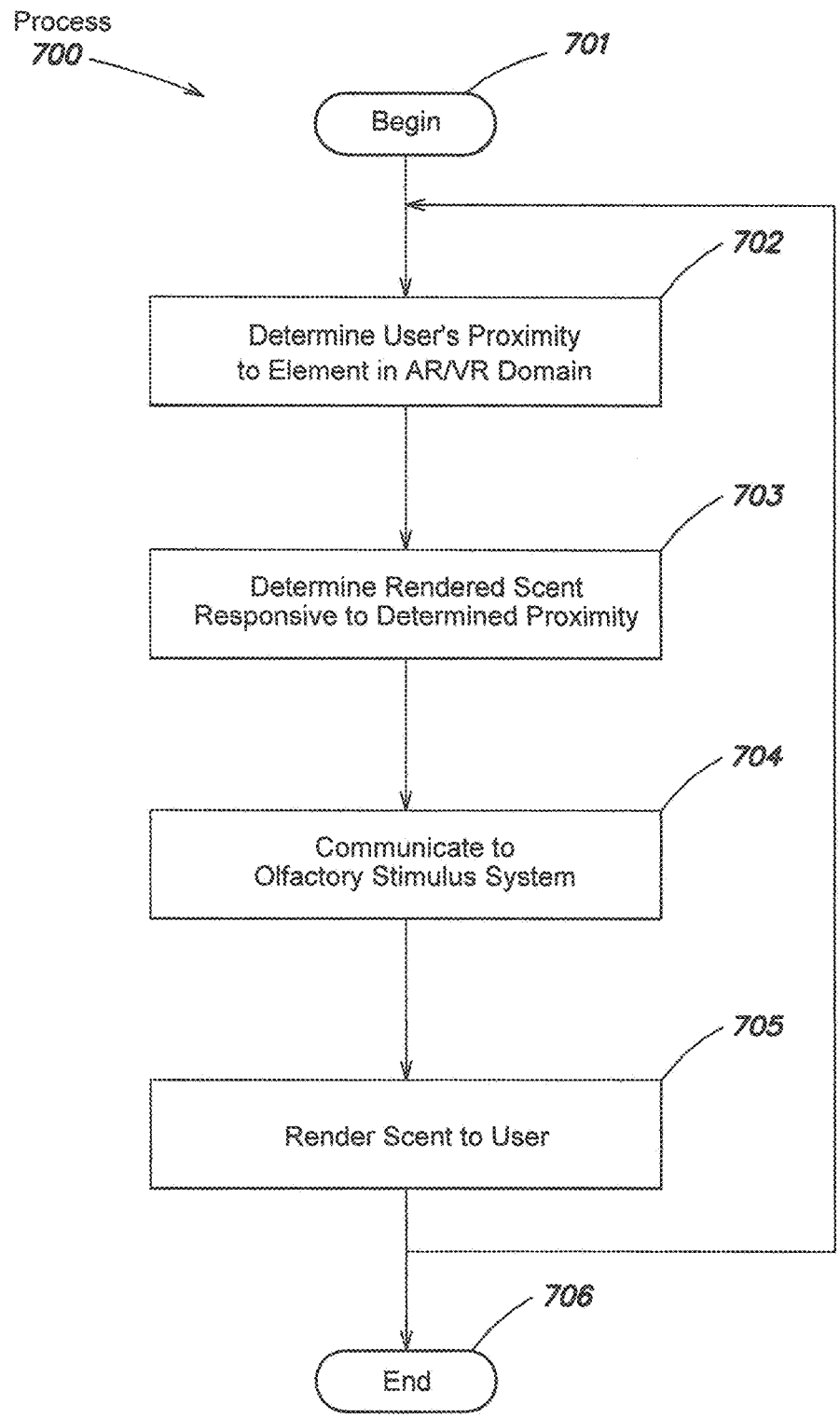
FIG. 7 shows an example process for rendering scent information according to various aspects.

FIG. 7 shows an example process 700 for rendering scent information according to various aspects. Process 700 may be performed to generate an odor impression (e.g., in an XR environment). For example, process 700 may be performed by game system 101 described above with reference to FIG. 1.

At block 701, process 700 begins. At block 702 the user's proximity is determined in relation to an element in an AR/VR domain. For instance, the game engine (e.g., of game system 101) while executing the game code may monitor the user's proximity to one or more virtual elements such as environmental elements, game elements or other surface or object.

At block 703, the system may determine a rendered scent responsive to the determine proximity between the user and the element. For example, if the user is within a certain proximity of a surface that has a scent associated with it, the executing software may determine a scent to be "played" to the user at some point in time during the game execution or other contact rendering to the user.

At block 704, the system communicates control information indicating the scent to be rendered to the olfactory stimulus system (e.g., a controller of olfactory stimulus system 102). Such information may include any type of encoding information, such as a duration of a scent to be rendered, an intensity value or other information. Such information may be transmitted, as discussed above, over a wired or wireless communication link between a content providing system and the olfactory stimulus system.

At block 705, the olfactory stimulus system renders the sent to the user. At block 706, process 700 ends, although it is appreciated that this process may work as a continuous loop as the user is experiencing the AR/VR content.

Figure 8:
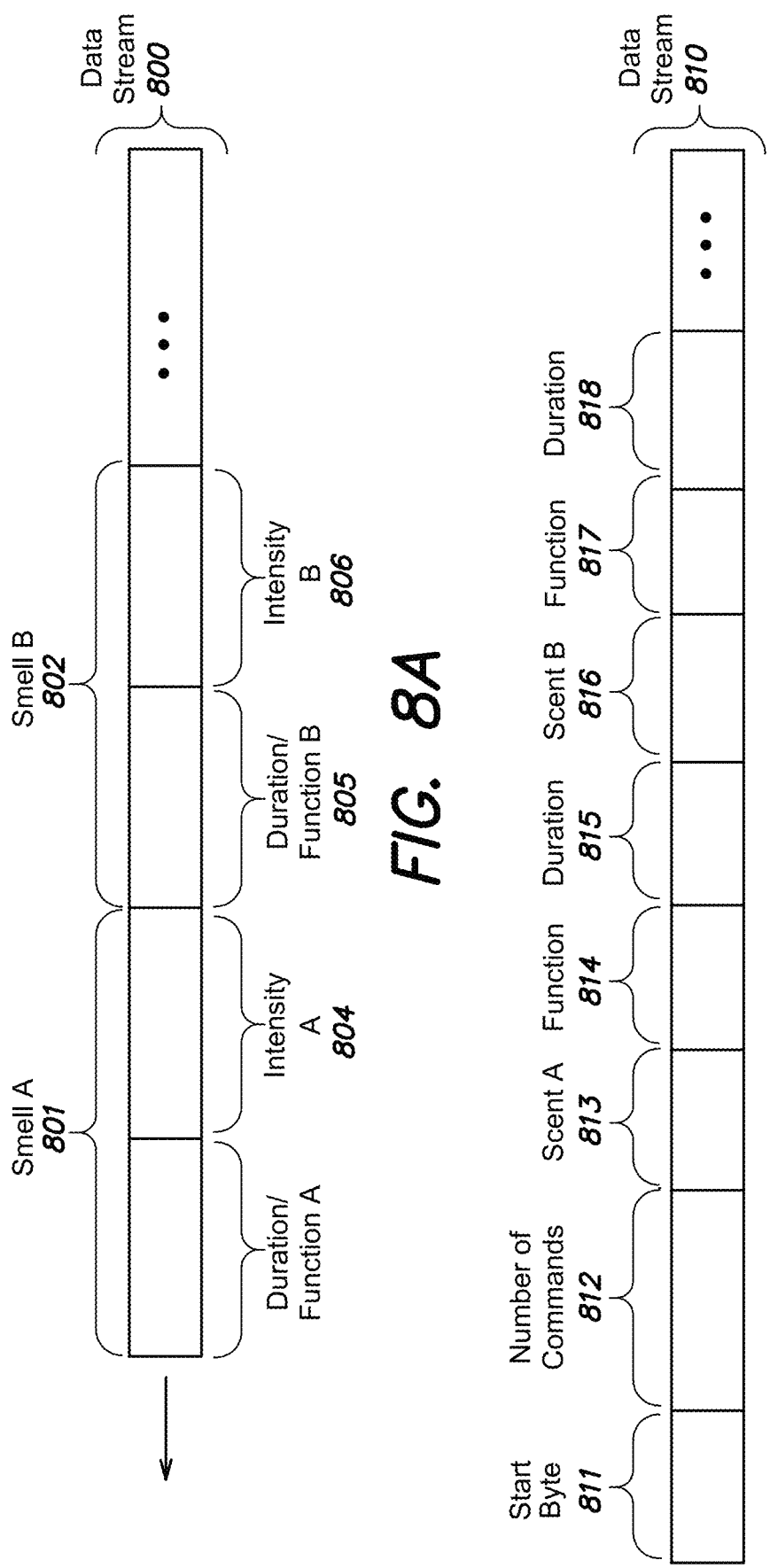
FIGS. 8A-B shows example data formats for communicating scent information according to various embodiments.

FIG. 8A shows an example format for communicating scent information according to various embodiments. As discussed above, the olfactory stimulus system may be capable of receiving a data stream (e.g., data stream 800) sent from a game engine (e.g., of game system 101) or other content providing system for the purpose of communicating smell information. As shown, the data stream may include one or more pieces of information that correspond to particular smells to be rendered to the user.

For instance, a portion of information corresponding to smell A (e.g., item 801) may be transmitted serially from the content provider to the olfactory stimulus system. Data element 801 may include a number of fields, characteristics, and/or values that qualify a particular smell. Element 801 may include specific information that identifies which smell to be played, what duration, in what intensity. Data element 801 may include additional information encoded that reflects how the sent is to be delivered to the user. In some embodiments, element 801 includes a duration/function for smell A. Such information may include a value that specifies the duration, as well as a specific identification of smell A. Further, element 801 may include an intensity value A 804 that numerically represents a played intensity of the identified smell. The system may be capable of transmitting multiple smells (e.g., Smell B 802 with duration/function B 805 and intensity B information 806).

FIG. 8B shows another example format for communicating scent information according to various embodiments. As discussed above similar to the system described above with reference to FIG. 8A, the olfactory stimulus system may be capable of receiving a data stream (e.g., data stream 810) sent from a game engine (e.g., of game system 101) or other content providing system for the purpose of communicating smell information. As shown, the data stream may include one or more pieces of information that correspond to particular smells to be rendered to the user. Notably, data stream 810 may be a different format which is communicated to the olfactory stimulus system when the scent is needed such that data is not continually sent and need not be processed when scent should not be present. In such a format, the data stream 810 (e.g., a partial stream or finite string of data) may be sent to the olfactory stimulus system.

Data 810 may include a start byte 811 that appears at the start of the message and which indicates to the olfactory stimulus system (e.g., a microcontroller operating the olfactory stimulus system) to start processing remaining bites and the string or partial stream of data. In a resting state, a microcontroller of the olfactory stimulus system may be constantly for receipt of a start byte (or other header type or indication). The second portion of the message includes a number of commands 812 which indicates the number of scents in the stream, and which indicates how long the stream will be. Following data element 812 are the actual scent indications to be rendered (e.g., scent A, scent B, etc.). Each of the scent indications includes, for example, a scent label or designation (e.g., an encoded form of Scent A placed within data element 813), a function state of the scent (e.g., an intensity, delivery pattern, etc. for the scent encoded in data element 814), and a duration of the scent (e.g., element 815). Each of the various scents to be rendered may include respective function and duration information encoded within the data stream.

It should be appreciated that smell information may be communicated in real time between entities for the purpose of delivering a realistic environment. Such information may be transmitted in parallel with AR/VR environment information, and in some embodiments, there may be a coordination protocol that synchronizes such information.

Figure 9:
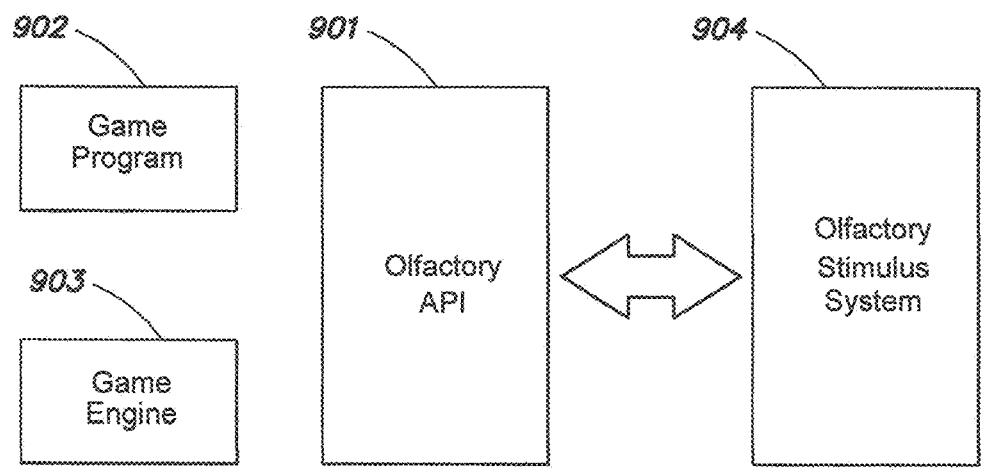
FIG. 9 shows an example software architecture according to some embodiments.

FIG. 9 shows an example software architecture according to various embodiments. In particular, game program 902 and game engine 903 may be capable of communicating to the olfactory stimulus system 904 via an olfactory API 901. Olfactory API 901 may provide functions, interfaces, and parameters through which the game program 902 may communicate with the olfactory stimulus system 904. Further, in some embodiments, communication through the API may be bidirectional, in that information may be received from the OVR system. For example, a status of the OVR system may be communicated and may be visible to a content providing application. For example, whether the OVR system is functioning, has appropriate and suitable levels of media, etc. may be provided to another computing entity.

Although the embodiment of FIG. 9 shows the olfactory stimulus system 904 separate from the game program 902 and the game engine 903, in some embodiments, the olfactory stimulus system 904 may be implemented a component of the game program 902 and/or the game engine 903. For example, the olfactory stimulus system 904 may include a software package that may augment the game program 902 and/or the game engine 903.

In a practical example, when someone encounters an object in VR there are things that occur on the game software/driver side of the game and then there are things that happen on the hardware/firmware side of the game. On the software side, a player interacts with an object based on proximity to that object. The user's proximity to an object generates a value in the gaming engine. Other objects may distort that proximity value such as a wall or wind effects.

The value (whether or not it is modified) is then formatted into a string of characters by the API. That string of characters is then passed on to the microcontroller via USB or Bluetooth or LAN/WAN/Wi-Fi or any other digital wired or wireless communication link. In one example implementation, the system is connected via USB. The string's length is determined by the multitude of scents. In some embodiments, the more scents there are to be rendered, the longer the data string sent over the digital connection.

On the hardware side, the string of characters is then relayed to the microcontroller and is interpreted by the firmware (e.g., residing on the memory of the controller). The firmware selects a mode in which the smell will be delivered and then finally executes an amplitude on the piezoelectric value system(s) which is based on the proximity value generated from the software side. In one implementation, the entire process can be performed about 10-100 times per second and updates the amplitude of the scent as a user interacts with the VR environment and the predetermined or tagged objects in that environment. VR objects can be tagged during the development of the game by a game designer or post compilation of a game through the use of computer vision algorithms during game play.

It should be appreciated that the system, mechanical implementation, software and controls may have a number of features that are usable either alone or in combination with other features. For example, in another implementation, the system may be capable of limiting "brown smell" or residual smells produced as a byproduct of playing previous smells. One example process for eliminating brown smell includes several methods. This first method includes using scent formulas and controlled atomization sizes which are highly dispersive and do not stick to surfaces very well. This ensures that the scent will clear away in a relatively short amount of time. A second process includes restricting the outlet size orifice near the scent cartridge which creates a passive high-pressure area. This functions as a passive gate to keep additional scent molecules or atomized clumps from exiting the outlet when the piezoelectric devices are in a resting state. Essentially this function acts as the brakes to the scent delivery mechanism. The third function is to maintain control over the particle release size (nominally 20-2 um in size). Maintaining particle size may be accomplished, for example, through a VMT, venturi and/or other dispersion mechanisms. It should be appreciated that other features may be provided according to other implementations.

FIG. 10 shows another example device that may be used to render scent according to some embodiments. For example, FIG. 10 shows a piezoelectric device 1000 that may be used to render scent information. Device 1000 may be relatively small in size (e.g., 1-2 cm in diameter, or other size) such that it may be used in a personal scent rendering device such as that shown by way of example in FIG. 11. Device 1000 may be circular in form, and include an area 1001 where scent is released. Device 1000 may include scent media either embedded within the device, or the device is capable of receiving scented material from a channel, or reservoir (e.g., in liquid form). Device 1000 may be operated by providing an activating signal through one or more electrical leads (e.g., leads 1002).

FIG. 11 shows an example device 1102 that may use one or more devices to render various scents according to some embodiments. In particular, device 1102 may be adapted to receive one or more piezoelectric elements such as those shown by way of example in FIG. 10. Further, device 1102 may be adapted to attach to an AR/VR headset (e.g., AR/VR hardware 202). For instance, device 1102 may be adapted to mount to an AR/VR headset via a mounting plate 1101. Device 1102 may be affixed to the headset via one or more attachment elements such as screws, mounts, adhesive elements, or similar elements. Device 1102 may include one or more openings 1103 through which scent is rendered. Because device may be mounted near a lower surface of the headset, the openings of device 1102 may be positioned near a user's nose. Device 1102 may be arc-shaped such that the openings are positioned substantially around an area near the user's nose.

Figure 12:
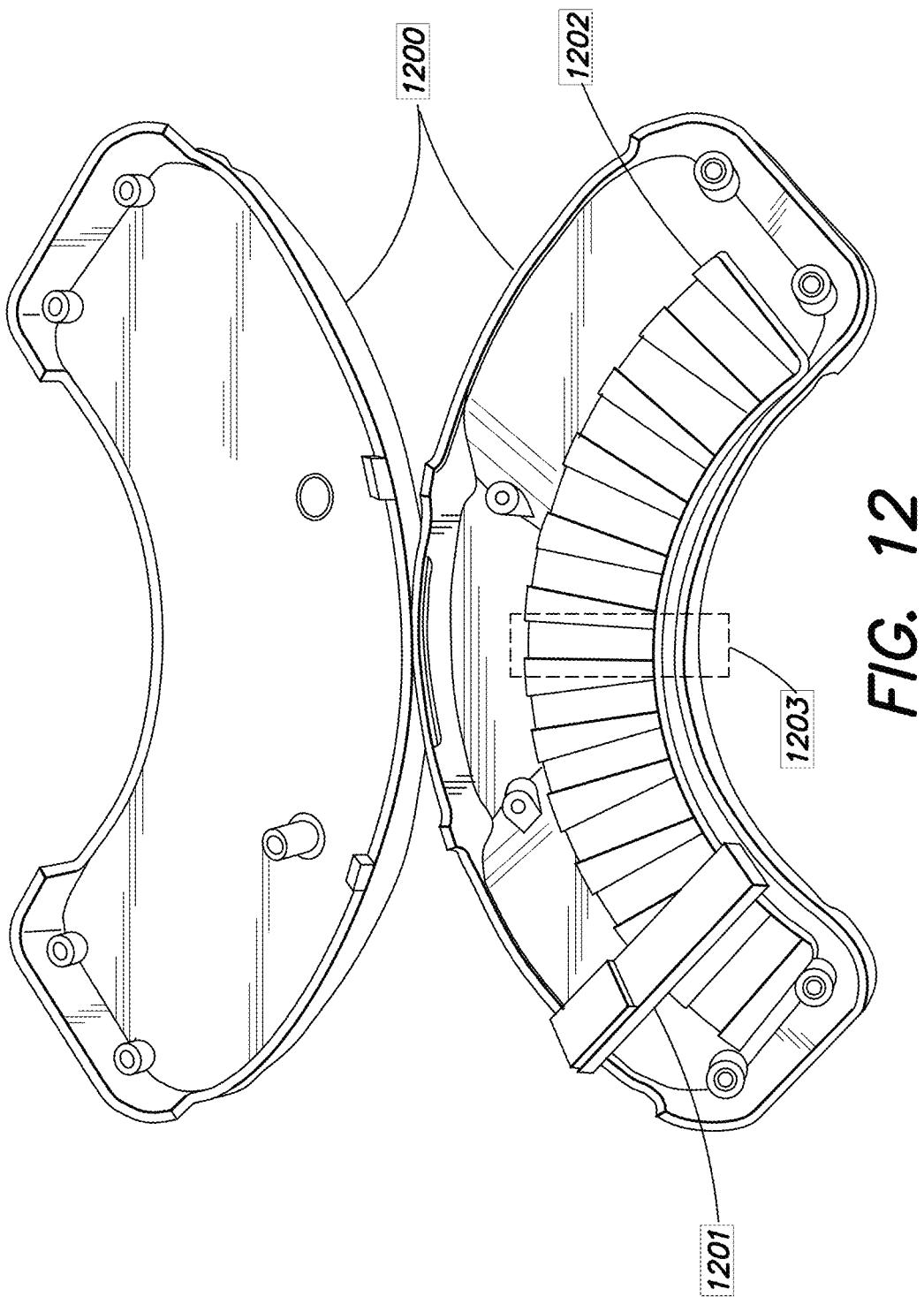
FIG. 12 shows another device that many be used to render various scents according to some embodiments.
Figure 13A:
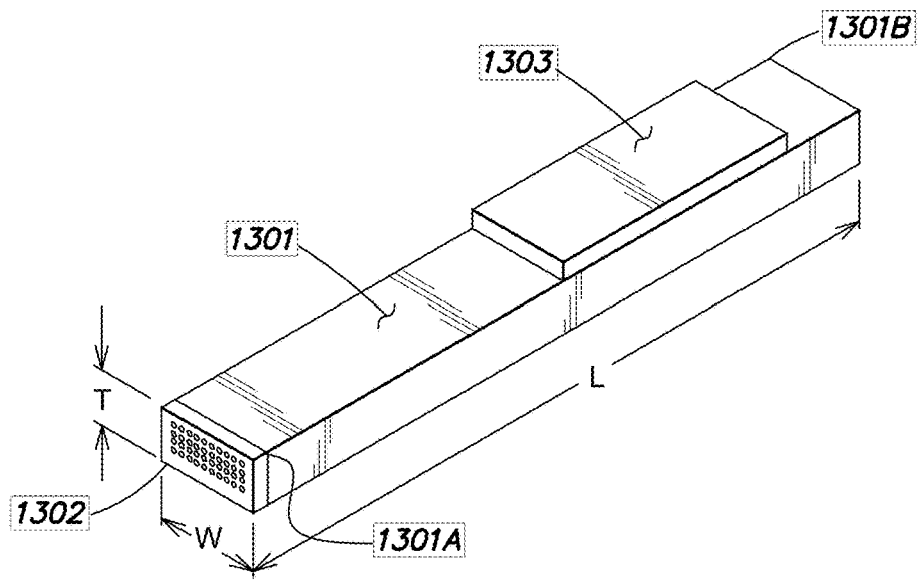
FIGS. 13A-13D show a device for generating atomized fluid according to some embodiments.
Figure 13B:
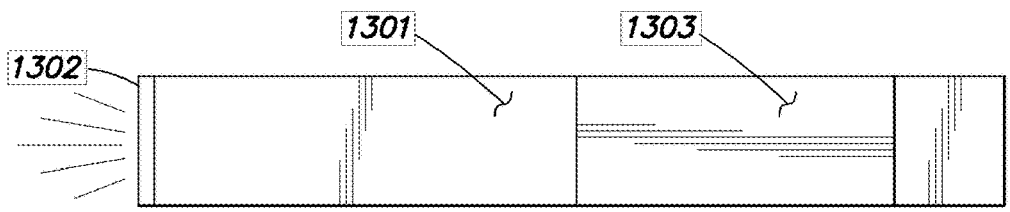
Figure 13C:
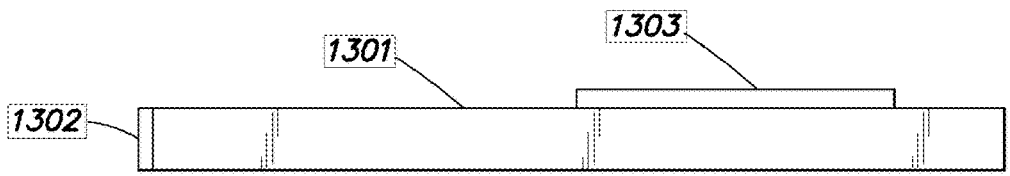
Figure 13D:
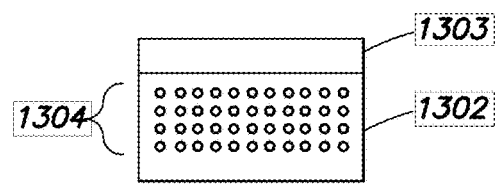

FIG. 12 shows another device 1200 that many be used to render various scents according to some embodiments. Similar to device 1102, device 1200 may be arc-shaped and may be adapted to be attached to an AR/VR headset. Also, device 1200 may be adapted to receive one or more piezoelectric elements (e.g., piezoelectric element 1201). In some embodiments, such elements may be rectangular in shape, and as discussed below with respect to FIGS. 13A-13D, they may be configured to atomize a fluid and project the atomized fluid out of an end of the tube towards a user's nose. Several piezoelectric elements may be arranged in an arc of the device 1200. The elements may be held in channels (e.g., channel 1203) by a holding element 1202. In some embodiments, the holding element may be manufactured using a rubber-like material to isolate the elements and their vibratory effects from one another and the main housing of device

1200. In some embodiments, the piezoelectric elements are sandwiched between several holding elements, thereby positioning and holding the piezoelectric elements within their respective channels. The piezoelectric elements may be adapted to render different scents. Each of the elements may be selectively activated by a controller that sends activating signals to a particular selected element.

FIGS. 13A-13D show a device for generating atomized fluid according to some embodiments. In particular, FIGS. 13A-13D show some embodiments of a device for generating atomized fluid. The device comprises a rectangular tube (1301) having a cross-sectional shape a width (W), a depth (T) and a length (L). A piezoelectric plate (1303) is attached across the width (W) of the tube. In some embodiments, the piezoelectric plate (1303) may be attached to the rectangular tube (1301 via glue, epoxy, solder or other adhesive. It should be appreciated that although a rectangular tube is shown, other shapes of tubes may be used (e.g., circular, triangular, square, etc.).

An aperture plate (1302) is attached to an end of the tube (1301A) while a second end (1302B) is open and is configured to receiving a fluid and supplying the fluid to the aperture plate (1302) through the tube. The piezoelectric plate (1303) is connected to a circuit that generates an electrical signal at a frequency that is equal to the resonance frequency of tube and in an amplitude that is sufficient to produce a flow of atomized droplets. The electrical signal may be, in some embodiments, an alternating signal that is applied to contacts of the piezoelectric plate 1303.

In one embodiment, the tube is made of brass and has a width of 6.35 mm, a depth of 3.125 mm, and a length of 40 mm, with a resonance frequency of 50,000 Hz. It should be appreciated however, that other dimensions, configurations and resonant frequencies may be used. In some embodiments, the piezo element and tube form a unimorph device including an active layer (e.g., the piezo element) and an inactive layer (e.g., the tube surface). One implementation includes a tube having a rectangular or square in shape. In some conventional piezo elements, they may use a pinching/squeezing mechanism to deliver liquids, however, in some embodiments as disclosed herein, a medium (e.g., a liquid) is aerosolized via perpendicular acoustical waves induced by a piezo element.

In some implementations, there are multiple ways that the medium can come into contact with the plate:

Free in housing—The liquid is just free in the tube and capped at the end opposite the aperture plate end to seal inside. The vibration pattern forces the liquid in contact with the plate.

Wick—A wick is placed in the tube and capped in with the liquid to force the correct capillary action to move the liquid to plate in conjunction with the vibration. In some embodiments, the wick may be shaped to fill the area within the tube (e.g., a rectangular, tubular, or square shape). In some implementations, the wick element may be a replaceable item, and may be accessible to be replaced. The wick may also be part of or coupled to a reservoir that holds liquid to be dispersed. The wick may be, in some embodiments, bidirectional or unidirectional wicking material made out of, for example, natural fibers and/or synthetic fibers including cotton, polyethylene, nylon, metal, graphene, among others.

Cartridge—A cartridge of custom design is inserted into the back to the tube with a connection point to the tube and plate. The cartridge may, or may not, use a wick or material that has a wicking property.

Figure 14:
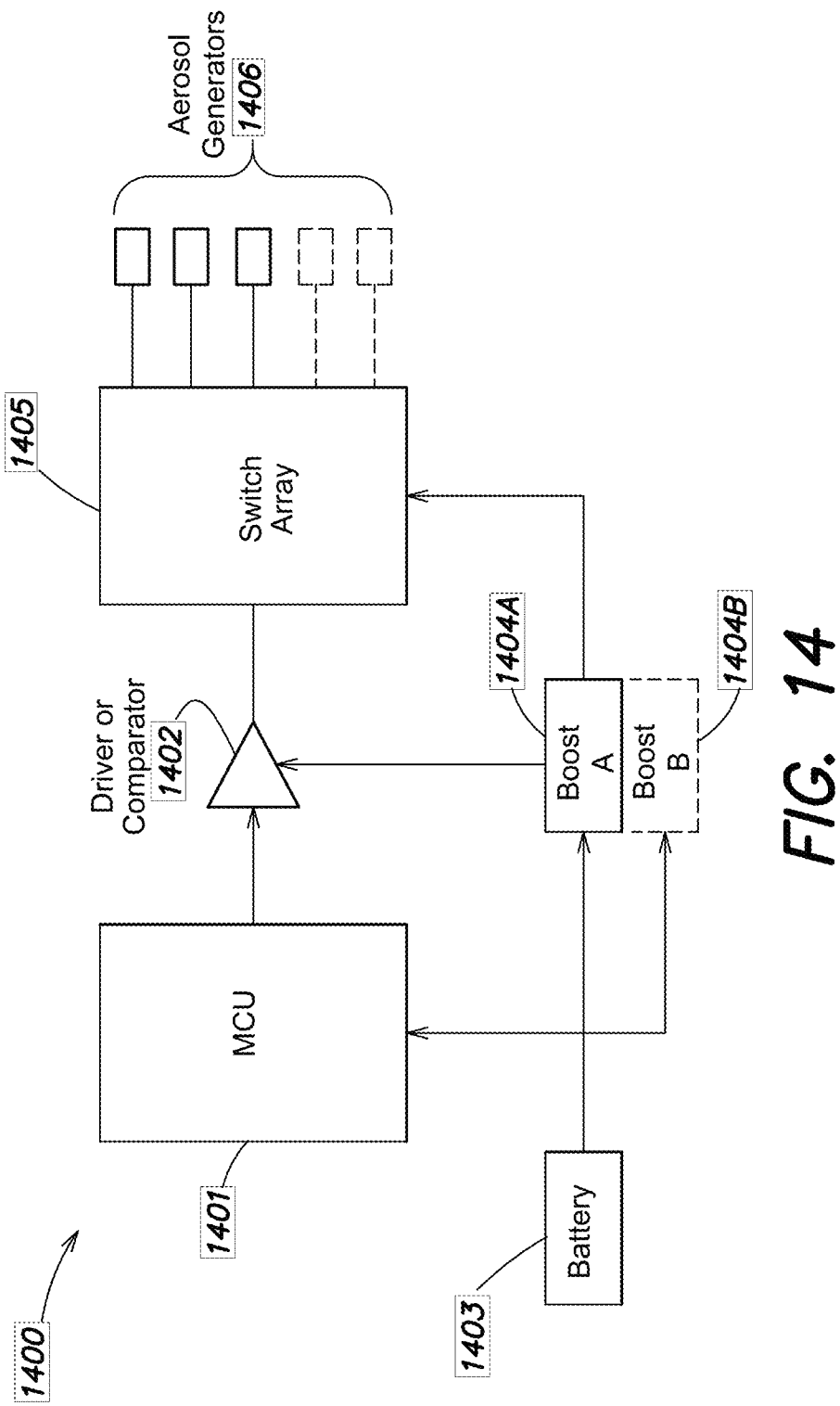
FIG. 14 shows an alternative control system according to some embodiments.

FIG. 14 shows an alternative control system according to some embodiments. In particular, one or more alternative control systems may be used in some embodiments where the piezo device includes one or more tube structures arranged in an array. The circuit may operate, for example, similarly to the system described above with respect to FIG. 5, which performs similar functions. In particular, a device driver circuit may be used to selectively activate different piezo elements (e.g., in an array) according to what scent is addressed (e.g., within a received stream of commands).

In particular, generally within the driver circuit shown in FIG. 14, a microcontroller generates a frequency which is then amplified in power greatly in order to drive selected piezo elements. Switches may be used to control the activation of the amplified power signal. The signal itself can be, for example, a signal of a fixed frequency with a 50% duty cycle. However, it should be appreciated that parameters of the signal (e.g., shape, length, height, pattern, etc. of the signal waveform) may be selectively varied to produce different intensities and lengths (e.g., duration) of scent production. Further, it should be appreciated that a DC signal may be used which includes positive signals or alternatively an AC signal may be used consisting of both positive and negative signals.

FIG. 14 shows a general circuit design which includes several subcomponents including a battery (e.g., battery 1403), a microcontroller (e.g., MCU 1401), a power conversion "boost" (e.g., via boost device A, boost B (elements 1404A, 1404B) and a switching array (e.g., switching array 1405). Optionally, a driver or comparator (e.g., a MOSFET comparator, e.g., element 1402) may be used to drive the logic coming from the MCU to a higher or lower power level to drive the switching array. Also, optionally a secondary power conversion may be used in order to provide a power source used to drive a second logic level voltage. The switching array 1405 is adapted to receive serial signal and convert that signal into the actuation of a specific channel. Each channel coming from the switch array is used to drive each of the individual aerosol generators (e.g., generators 1406). In some embodiments, the array should be sufficiently fast and rated for the appropriate voltage and current in order to be able to drive the aerosol generators in a real-time manner.

Figure 15:
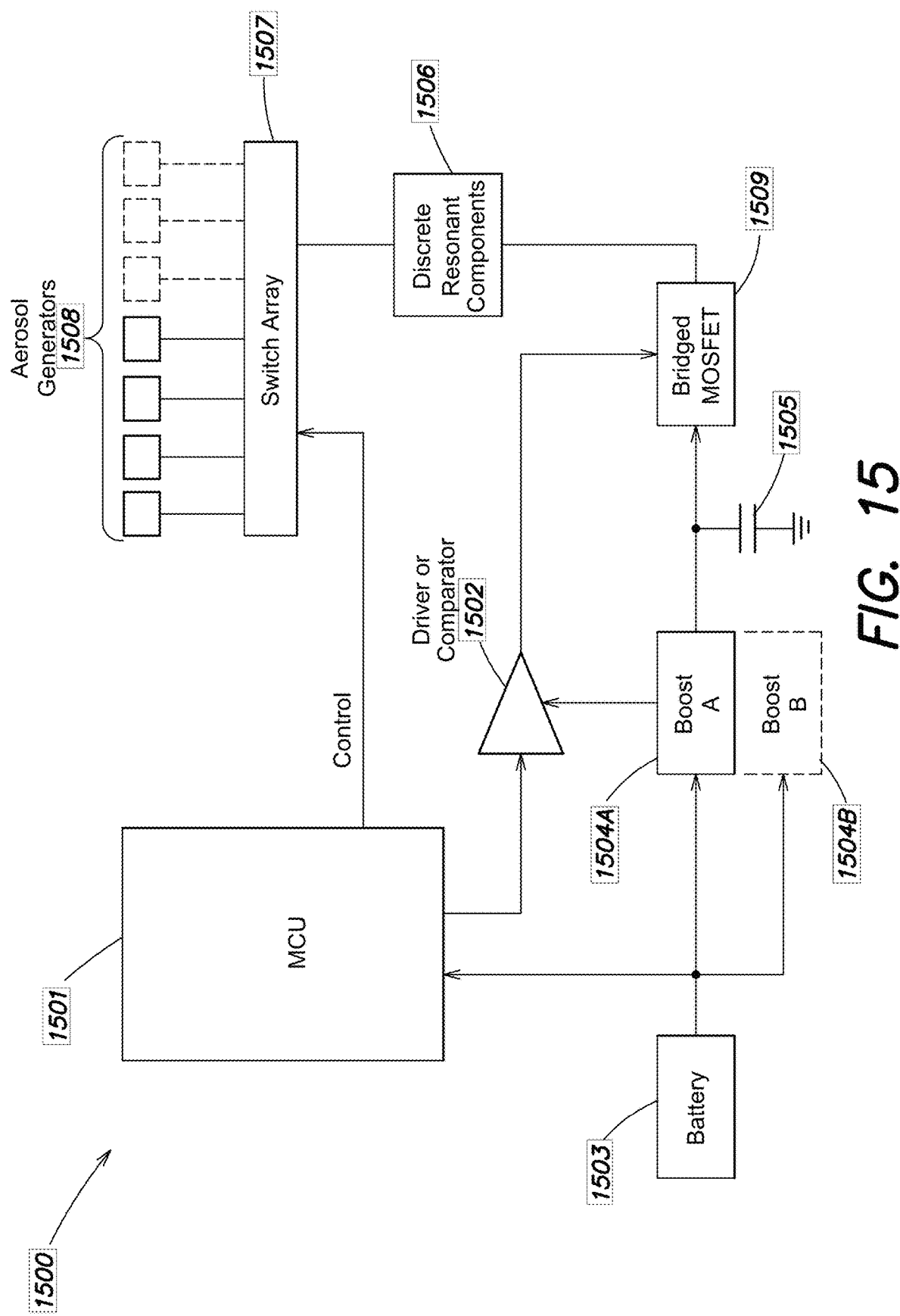
FIG. 15 shows another alternative control system according to some embodiments.

FIG. 15 shows another alternative control system according to some embodiments. In particular, FIG. 15 shows a general circuit design which includes several subcomponents including a battery (e.g., battery 1503), a microcontroller (e.g., MCU 1501), a power conversion "boost" (e.g., via boost device A, boost B (elements 1504A, 1504B), a bridged MOSFET (e.g., element 1506) and a switching array (e.g., switching array 1507). Optionally a driver or comparator (e.g., a MOSFET comparator, e.g., element 1402) may be used to drive the logic coming from the MCU to a higher or lower power level to drive the switching array and or the bridged MOSFET. In some embodiments, optional discrete resonant components (e.g., discrete resonant components 1506) such as capacitors/inductors can be used for further power amplification and signal smoothing. In the circuit shown in FIG. 15, the bridged MOSFET takes signals, (typically in the form of a timed frequency with a duty cycle) from the microcontroller and then amplifies that signal to a higher power level. The switching array is then opens a channel in which the power signal coming from the half bridge can then actuate the aerosol generators with the assistance/amplification of the resonant components.

Figure 16B:
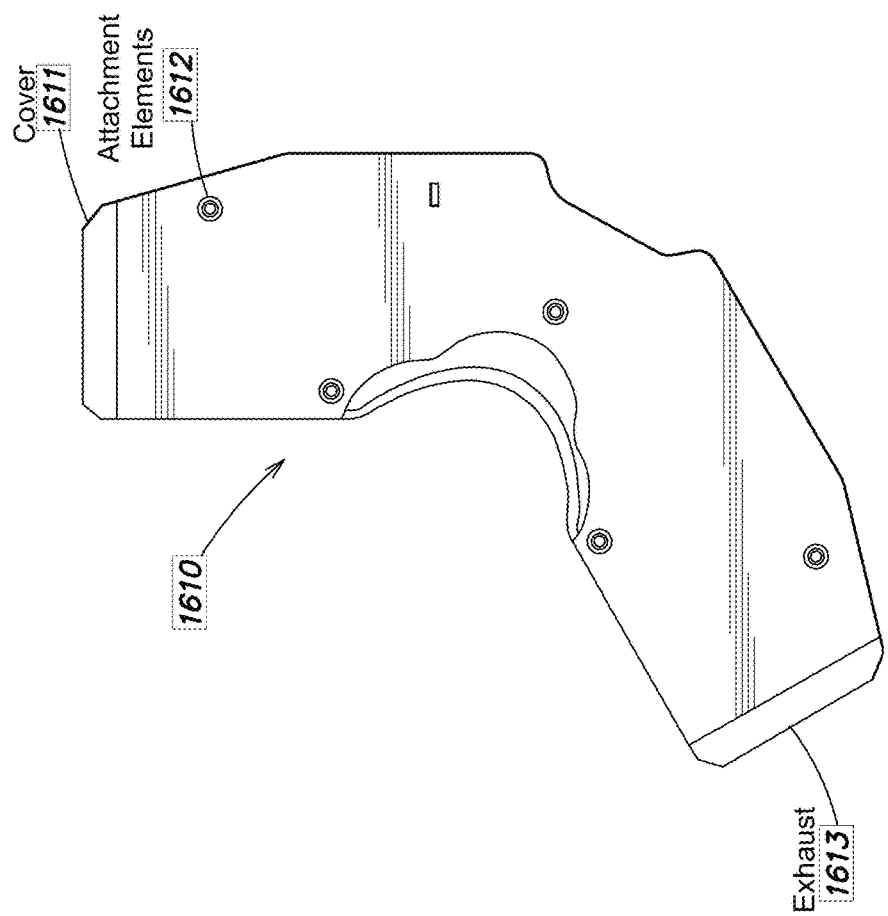
FIGS. 16A-16E show various views of an example olfactory stimulus system according to some embodiments.
Figure 16A:
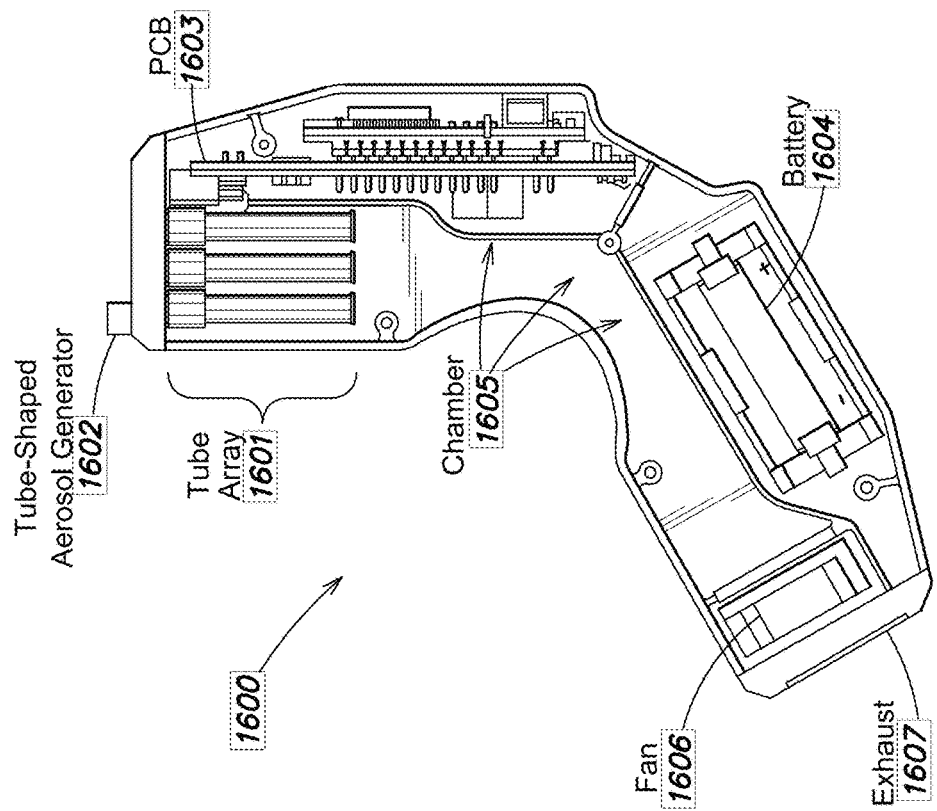
Figure 16C:
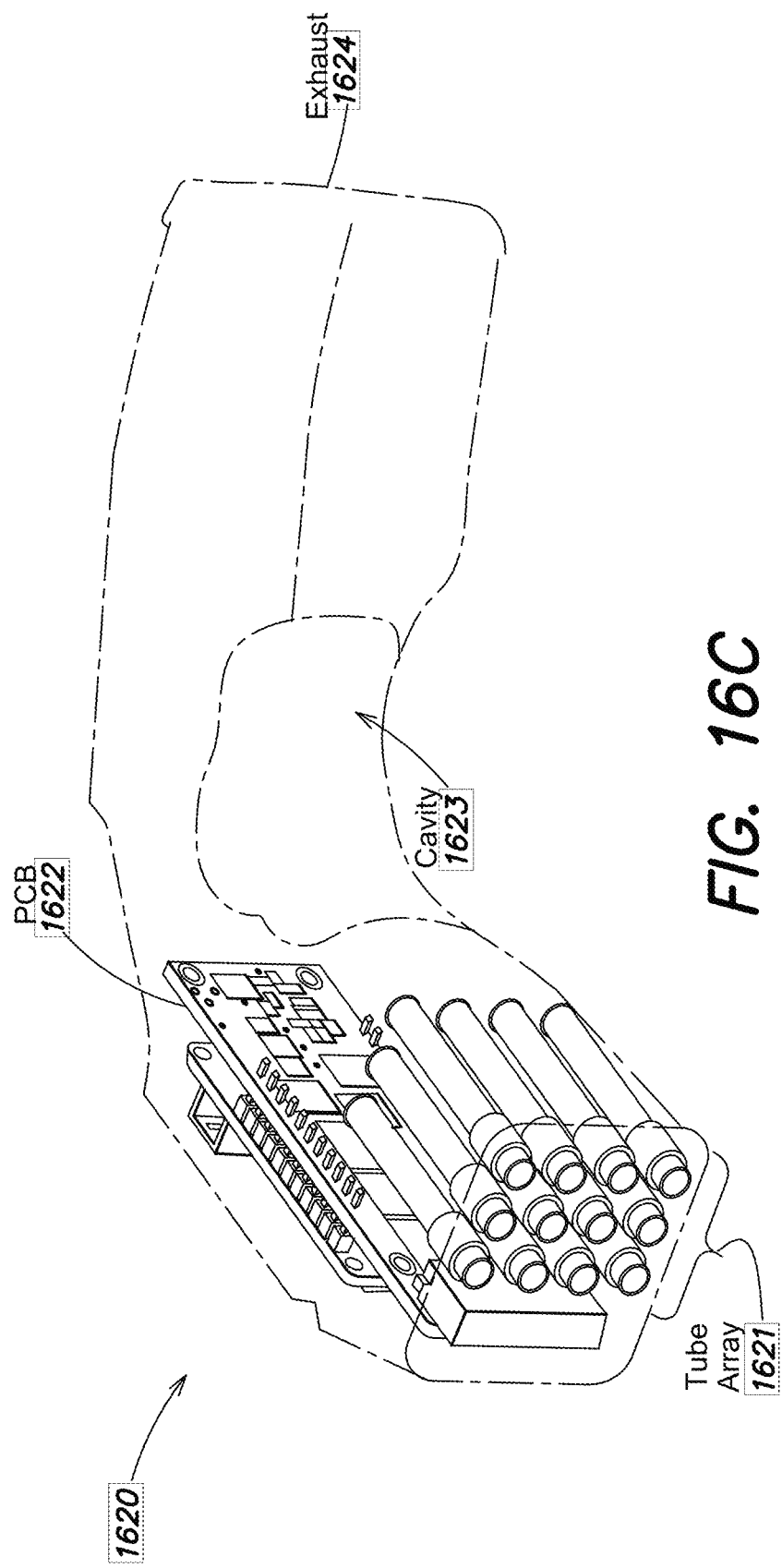
Figure 16D:
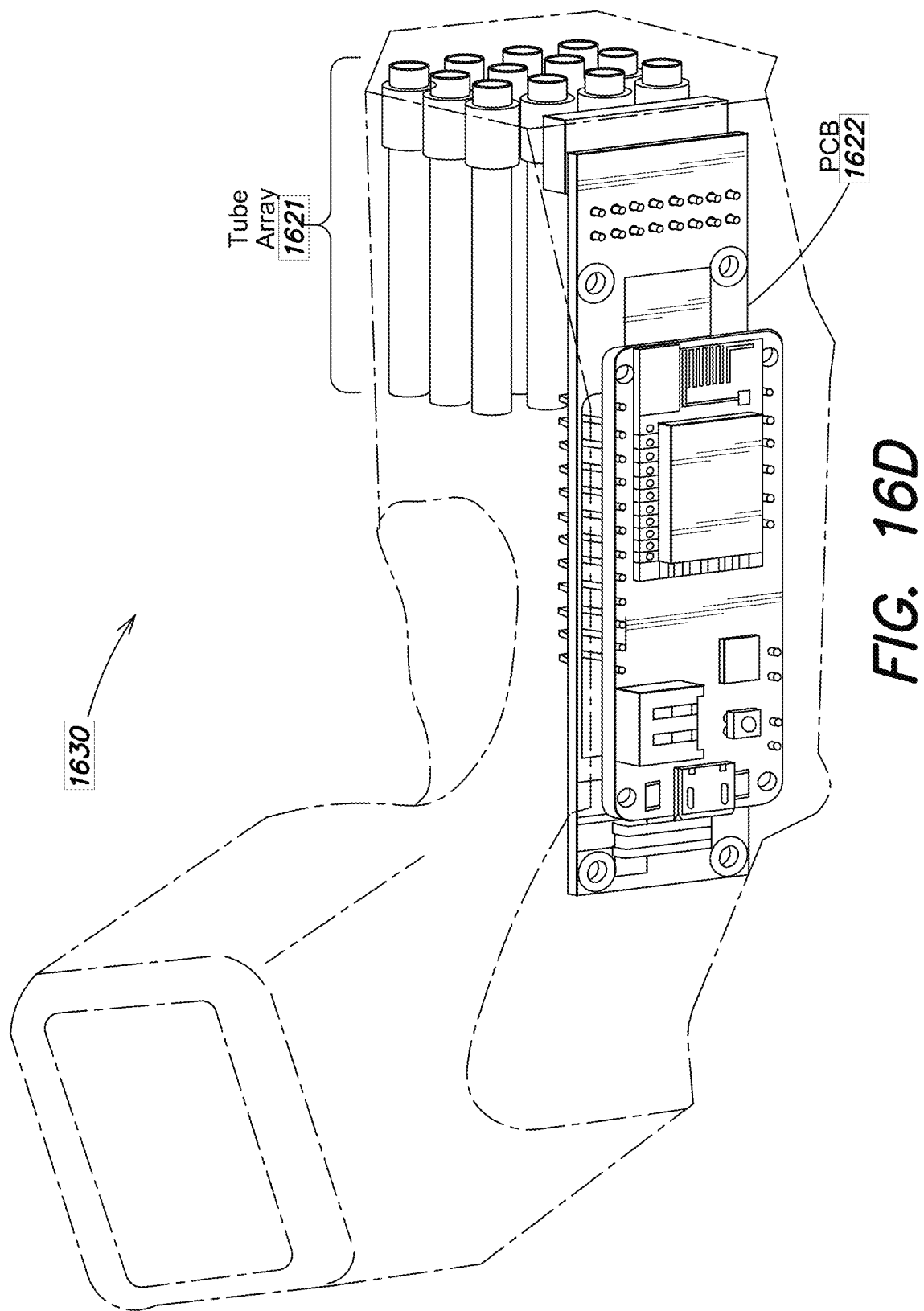
Figure 16E:
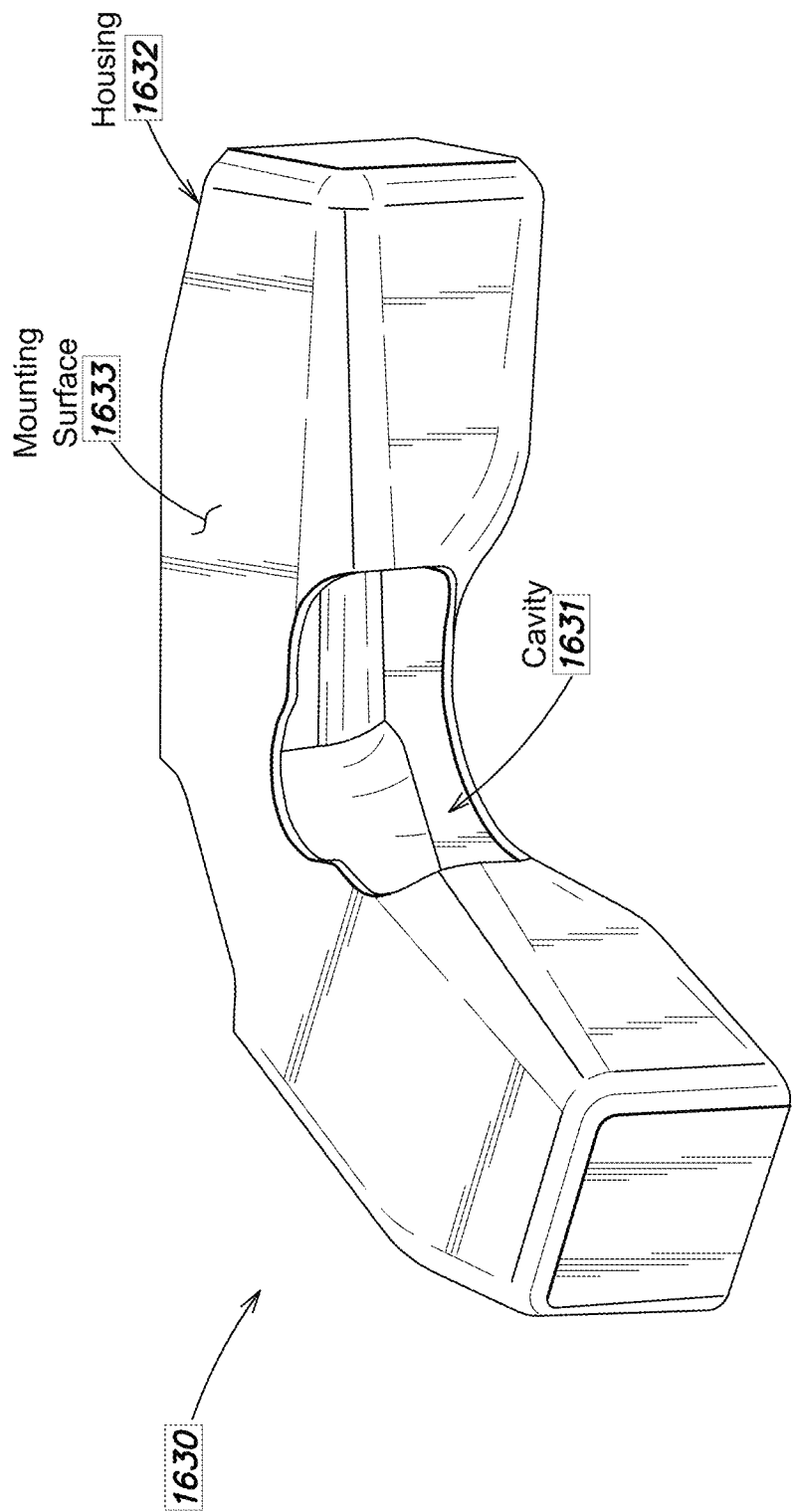
Figure 17A:
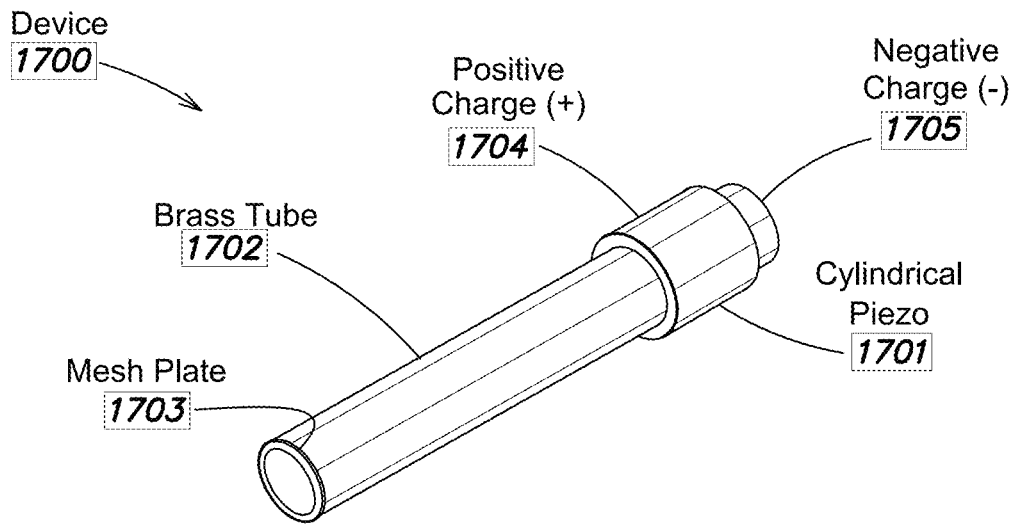
FIGS. 17A-17B show a device for generating atomized fluid according to some embodiments.
Figure 17B:
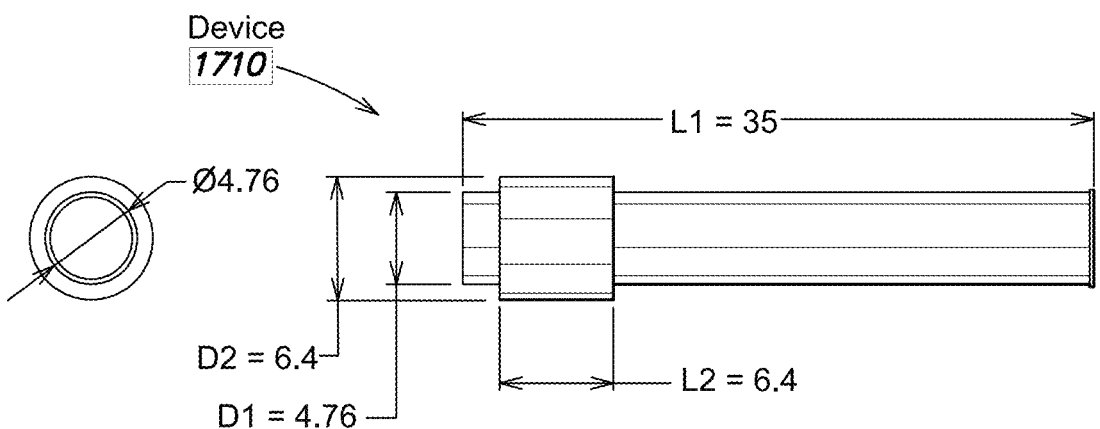
Figure 18:
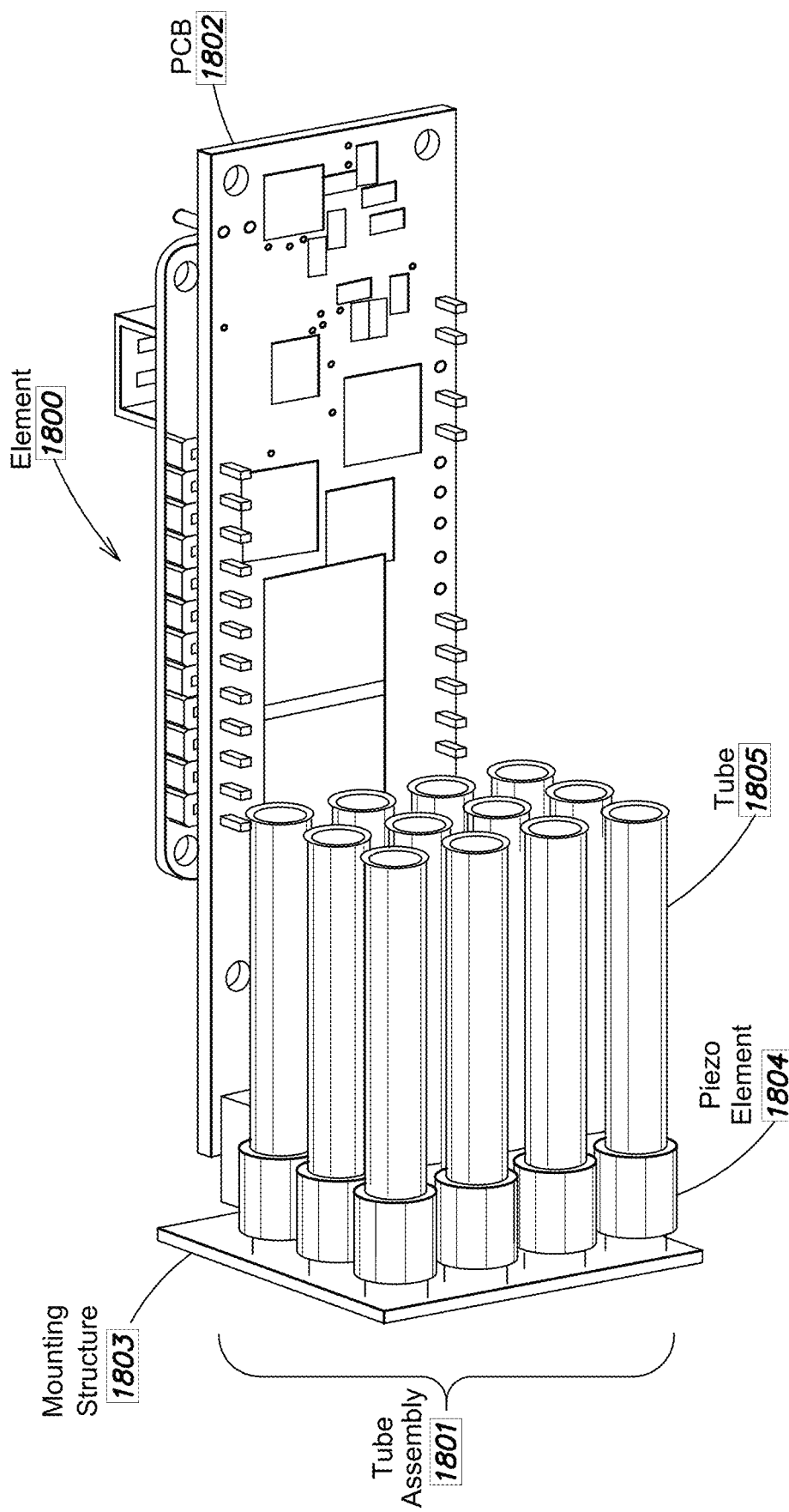
FIG. 18 shows a more detailed view of an element including a tube assembly according to some embodiments.

FIGS. 16A-16E show various views of an example olfactory stimulus system according to some embodiments. In FIG. 16A, an example olfactory stimulus system 1600 is shown which includes an L-shaped housing including a number of different components similar to those discussed above with reference to FIG. 1. In particular, system 1600 includes one or more piezo elements and in some embodiments, the Piezo elements take the form of tube—shaped aerosol generators (e.g., elements 1602).

In some embodiments, the elements are arranged within a tube array 1601. The piezo elements may be electrically connected to a PCB 1603 which includes one or more circuit elements such as those discussed above with reference to FIGS. 14-15. System 1600 may include a battery 1604 that is used to power one or more components and generate signals that may be used to drive the production of scent by one or more aerosol generators. Outputs of the tube array 1601 may be positioned abutting a chamber 1605. As discussed further below, a user's nose may be positioned within an opening of the chamber in order to receive one or more outputs of the tube array. In some embodiments, the individual tubes, their media, and/or the array may be a removable and replaceable item (e.g., to renew exhausted media).

At an opposite and of the system, there may be an exhaust 1607 which is used to remove sent from the chamber 1605. Near the output of the exhaust may be positioned a fan element 1606 (or other air moving device) which can be configured to move air in and out of the chamber from the exterior of the system 1600. Notably, it may be useful to clear sent away from the chamber as well as mix outside air with scents produced by one or more of the aerosol generators.

FIG. 16B shows a device 1610 similar to system 1600 whereby a cover 1611 encloses the elements within device 1600. Cover 1611 is attached to the remainder of the housing via one or more attachment element 1612. Cover 1611 encloses the chamber whereby outside air is input via exhaust 1613 or sent is removed from the chamber via the exhaust 1613.

FIG. 16C shows a three-dimensional view of a device that is similar to that shown in FIGS. 16A-16B. In particular, FIG. 16C shows a device 1620 that shows a three-dimensional tube array 1621 including as shown, 12 different aerosol generators positioned within the array. In some embodiments, the tubes are vibrationally isolated from each other such that vibration induced in one tube will not be translated significantly to another tube within the array. A housing of device 1620 includes several openings including a cavity 1623 in which a user's nose is placed. As shown, a PCB 1622 and tube array 1621 is positioned opposite an exhaust 1624 located at the other side of the device. FIG. 16D shows another view of the device (now shown as device 1630) which shows relative positioning of the PCB and tube array with respect to the housing and openings. FIG. 16E shows another view of the device (e.g., as device 1630) whereby only the external housing and viewable elements are seen. As can be more clearly seen, the housing 1632 forms a cavity 1631 in which a user's nose may be positioned. Further, device 1630 includes a mounting surface 1633 which may be attached by one or more methods to an AR/VR headset, such that the device is positioned near the user's nose. It should be appreciated that elements shown in FIGS. 16A-16E (e.g., PCB elements, tube arrays, etc.) may be similar or the same items among the various figures, but may be substituted with other elements as described herein.

FIGS. 17A-17B show a device for generating atomized fluid according to some embodiments. In particular, FIG. 17A shows a round tube device 1700 similar in function to the device discussed above with respect to FIGS. 13A-13D. Device 1700 may include a tube 1702 having a length (L1) and diameter (D1). A piezoelectric sleeve is attached at an end of the cylindrical tube, the element having a length (L2) and diameter (D2). In some embodiments, the piezoelectric sleeve may be attached to the cylindrical tube via glue, epoxy, solder or other adhesive.

Similar to the rectangular embodiment, an aperture plate (e.g., mesh plate 1703) is attached to an end of the tube while a second end is open and is configured to receiving a fluid and supplying the fluid to the aperture plate through the tube. The piezoelectric element is connected to a circuit that generates an electrical signal at a frequency that is equal to the resonance frequency of tube and in an amplitude that is sufficient to produce a flow of atomized droplets. The electrical signal may be, in some embodiments, an alternating signal that is applied to contacts of the piezoelectric element (e.g., via positive charge 1704 being applied to the piezo layer and a negative charge 1705 being applied to the tube).

In one embodiment, the tube is made of brass and has a diameter of 4.76 mm, and a length of 35 mm, with a resonant frequency in a range of substantially 100-300 KHz. The piezo element may have a diameter of 6.4 mm and length of 6.4 mm. It should be appreciated however, that other dimensions, configurations and resonant frequencies may be used. For example, the range of the frequency that a particular device may function can vary from a relatively low frequency (e.g., 20 kHz) to a relatively high value (e.g., 1 GHz). Using the example circular tube devices described above, the resonant frequency may be determined to be in a range of 100-300 KHz. Generally speaking, if the size of the tube is decreased, the frequency increases, but it should be appreciated that the resonant frequency depends on a number of factors and can be determined heuristically from testing the device.

In some embodiments, the piezo element and tube form a unimorph device including an active layer (e.g., the piezo element) and an inactive layer (e.g., the tube surface). In some conventional piezo elements, they may use a pinching/squeezing mechanism to deliver liquids, however, in some embodiments as disclosed herein, a medium (e.g., a liquid) is aerosolized via perpendicular acoustical waves induced by a piezo element. It should be appreciated that although certain shaped devices having certain dimensions are shown, other shaped elements having different dimensions may be used.

FIG. 18 shows a more detailed view of an element including a tube assembly according to some embodiments. In particular, FIG. 18 shows an element 1800 including a PCB 1802 having power and control circuitry that is used to selectively activate one or more piezo-based tubes within a tube assembly 1801. Each of the tubes (e.g., tube 1805) may be mounted on a mounting structure 1803. In some embodiments, the tubes are mounted to isolate them vibrationally from other tube elements. In some cases, spacers or other elements may isolate the tube elements. In some embodiments, piezo elements of each tube (e.g. piezo element 1804) are positionally separated by adjacent tubes yet are mounted by a common electrical connection (e.g., via a separate PCB). In some cases, there may be isolation elements that isolate each tube from the mounting structure.

Other Applications

Although such devices may be used in gaming and entertainment applications, it should also be appreciated that some embodiments described herein may be useful in a number of different applications outside the gaming/entertainment area. For example, some embodiments described herein may be used for one or more of the following.

Cognitive behavioral therapy—Cognitive behavioral therapists use a number of techniques to help their patients work through traumatic experiences including exposure therapy and virtual reality. It is appreciated that conditions such as PTSD from war and sexual trauma are the hardest to overcome for one reason: smell. These experiences are hardwired into our brains. By integrating unique, curated aromas into the therapy with VR, thousands of people may be helped to live normal lives and have normal relationships.

Remote surgery—It is appreciated that people's sense of smell works more quickly and efficiently than all of our other senses combined. VR has the unique ability to allow surgeons to perform complicated surgeries remotely but still only effectively offers 2D sense of objects during complex procedures. By augmenting the surgeon's sense of critical areas with scent, the chance of error may be decreased without the need for the surgeon to break a visual plane.

Sight impaired—For the visually impaired to participate in VR or AR, various systems must take advantage senses other than eyesight.

Forensics—Witnesses identifying the perpetrator is dangerously inaccurate and subject to implicit bias. Because of the direct link between scent, memory and emotion, VR may be coupled with scent creating a stronger, impartial, more just method of suspect identification, crime scene analysis and jury trials).

Therapeutic uses—Office, team, family, and relationship productivity goes up dramatically when people feel calm, rested and refreshed. For example, spending 10 minutes in scent enhanced, augmented reality can offer the same benefits as meditation, sleep or an hour of mindfulness.

Sports medicine—Training in VR kick starts psychosomatic response (i.e., nothing can create a "Pavlovian response" more quickly and powerfully than scent training. When an athlete is training for an event—like the Tour de France for example—in VR, aromatic stimuli may be created that increase or decrease heart rate, testosterone, or even pain/pleasure response that will be recreated during actual competition.

Piloting—As aeronautics and combat become more technologically advanced, any opportunity to make controls and feedback more intuitive to the pilot is paramount. It is appreciated that very second the pilot has to pay attention to a gauge or otherwise take his eye off more important visual cues can have catastrophic events. Furthermore, in high stress combat situations quick decision making without hesitation is key. Because smell stimulates the limbic (fight or flight) portion of the brain before being processed by the pre-frontal cortex, it is appreciated that VR training simulations utilizing olfactory cues can increase response time, preserve focus and decrease stress responses in real life situations.

Transposing senses and environmental conditions—For example, information of the environment such as temperature, humidity, radiation, unscented poisonous gas. For example, rover exploration in environments that are dangerous or toxic to humans rely too heavily on sight and crude robotics. By utilizing a VR/AR interface with a detection capability of scent that can be translated and communicated to an OVR system, the capability may be provided to explore the deep sea, radioactive sites, caves, and the like. In particular, human operators can receive and interpret data in real time in a much more meaningful way than ever before.

Space applications—Astronauts often need to be able to sense physical phenomena on the edge of perception, e.g., gamma rays, x rays, oxygen and carbon dioxide levels, and an OVR system may be used to accomplish experiencing these environments.

In some embodiments, an atomizer is provided for dispensing liquids into the air. In some implementations, a device is provided for generating atomized fluid specifically, but not exclusively, for production of small droplets of scented oil and other fluid-based fragrances, among other types of liquids. In some embodiments, the device comprises a tube having a proximal opening and a distal opening, wherein media inside the tube is forced out of the proximal opening via an aperture plate, examples of which are shown in FIGS. 13A-13D and 17A-17B. Such tubes may have any shape and size, such as rectangular or cylidricalcylindrical tubes.

In some embodiments, the tube further includes at least one piezoelectric plate that is attached to a face of the tube. The device further includes an aperture plate that is attached to the proximal end of the tube whereas the distal end of the tube is connected to a fluid supply source for supplying fluid through the tube to aperture plate at the proximal end of the tube. In some embodiments, the aperture plate includes a plurality of conical apertures that extend through the thickness of the plate.

In some embodiments, the device comprises a tube having a proximal opening and a distal opening, wherein fluid enters the distal end and is forced out of the proximal opening via an aperture plate. In some embodiments, fluid may be existing within the tube and/or added via the distal end, such as by a mechanism to add fluid as the device operates and forces the fluid out. In some embodiments, the device is provided with the fluid located within the tube.

The device further includes a signal generator circuit capable of producing an electrical signal at a selected frequency and voltage. When the frequency generator is connected to the piezo plate, cyclical stress waves are generated by the piezo plate which subsequently propagates along the length of the tube and produces oscillation which vibrates the aperture plate and generates a flow of atomized liquid through the apertures. In some embodiments, it is desirable that at least one surface of the tube has sufficient surface area and enables attachment of the piezo substrate. In some embodiments, the tube may be rectangular in shape, and a surface of the piezo substrate may be affixed to a substantial portion of a surface of the tube. In some embodiments, the piezo element is positioned more closely to distal end, allowing the stress waves to travel more significantly to the proximal opening.

In some embodiments, a single piezo attached to the tube generates longitudinal oscillation within the tube. In some embodiments, the tube does not bend due to the tube shape structure having a very high bending stiffness due to high moment of inertia of the tube's cross-sectional shape. However, vibration is produced within the tube as the piezo may vibrate with a resonant frequency of the tube, and the cyclical stress waves force the liquid through the apertures.

In some embodiments, a plurality of devices may be placed in a linear array. In such an arrangement, it may be desirable that one side of the tube will be narrow such that multiplicity of devices can be stacked together with a minimum space.

In some embodiments, the induced frequency produced by the piezo element is equal to the natural frequency of the rectangular tube in a longitudinal mode or bending mode.

In some embodiments, the tube is a rectangular tube having two wide faces such that the area of at least one of the faces is sufficiently wide to attach at least one piezoelectric element that is capable of generating a sufficient amplitude.

In some embodiments, the tube has trapezoidal cross-sectional shape and having at least one face that is sufficient to attach at least one piezoelectric element that is capable of generating a large amplitude.

In one embodiment the tube is circular in cross-sectional shape and having one face that is sufficient to attach at least one piezoelectric element that is capable of generate large amplitude.

In one specific embodiment, the width of the tube is between 0.05 mm to 0.1 mm and the length between 1 mm and 45 mm. In some embodiments, it is appreciated that a small device may be preferred for some applications, yet the size may be optimized so as to not require an excessively large resonant frequency. In some embodiments, the aperture plate is secured to the end of the tube via solder or glue and covers the entirety of the end of the tube. In some techniques, the aperture plate is circular and bent before connecting to edge of the tube. Additionally, the aperture plates may be flat or domed with the dome shaped outward from the end of the tube.

In some other applications, the aperture plate is sized to fit perfectly on the end of the tube. In some implementations, aperture sizes may be less than approximately 10 μm. For instance, apertures of approximately 5 μm range (+/−2 μm) may work for some applications. Generally, smaller aperture sizes are preferred, but the aperture sizes may be optimized to reduce clogging and the amount of force necessary to generate atomized fluid.

Example Processes for Generating Odor Impressions

Figure 19:
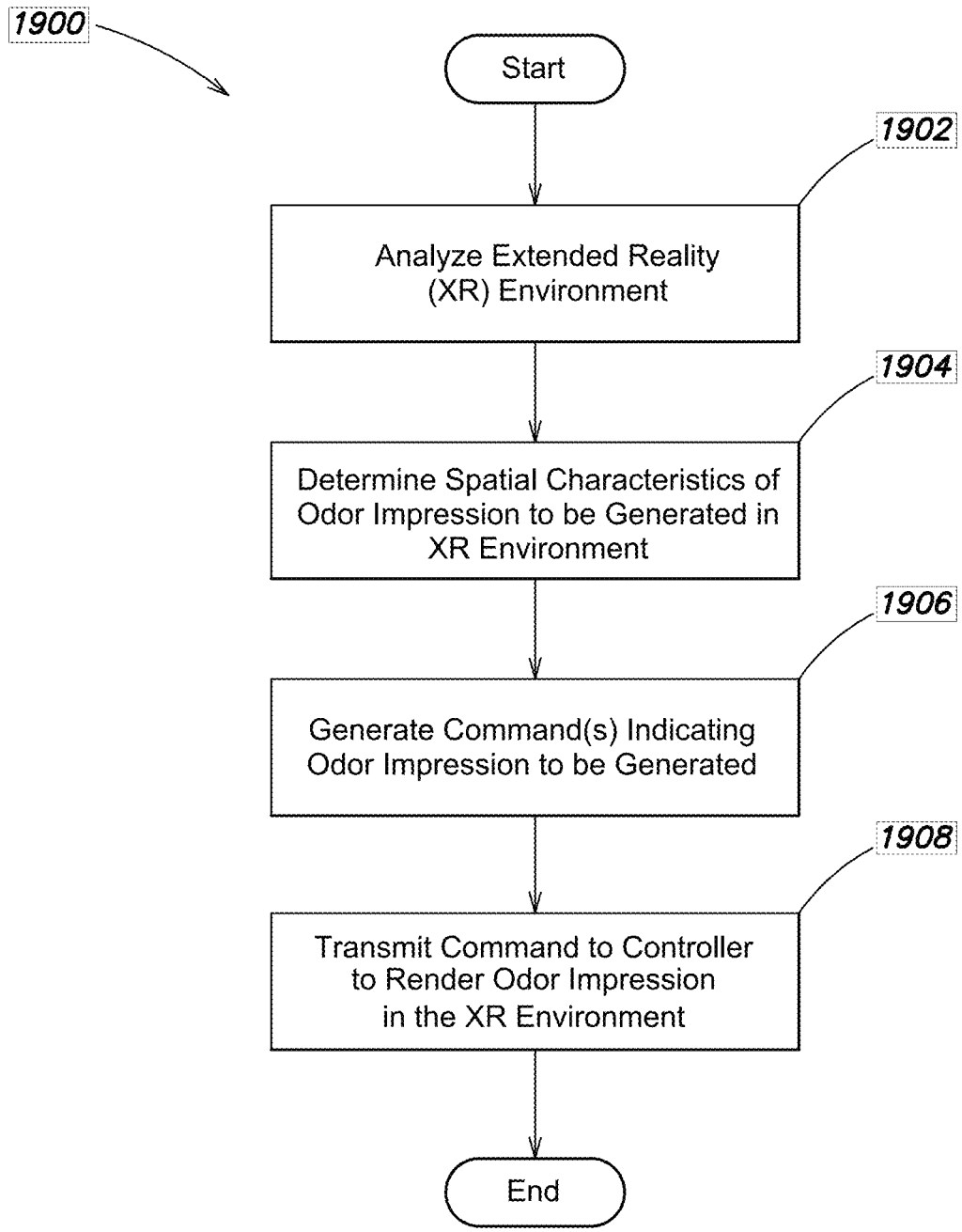
FIG. 19 shows an example process for rendering an odor impression according to some embodiments.

FIG. 19 shows an example process 1900 for generating an odor impression according to some embodiments. Process 1900 may be performed by any suitable computer system. In some embodiments, process 1900 may be performed by olfactory stimulus system 102 described herein with reference to FIG. 1. For example, process 1900 may be performed by a processor executing an architecture of scent software framework of the olfactory stimulus system 102.

Process 1900 begins at block 1902 where the system performing process 1900 analyzes an extended reality (XR) environment. In some embodiments, the XR environment may be an environment generated by the system. For example, the XR environment may be a virtual reality environment generated by a game engine. The system may analyze the XR environment to identify one or more scent generating assets in the XR environment. For example, the system may identify objects (e.g., flowers, food, and/or fire) in the XR environment that are to release a scent to be the scent generating asset(s) in the XR environment. In some embodiments, the system may identify the scent generating asset(s) by identifying objects encoded as scent generating object(s). For example, the object may be defined from a class of the system. The system may include an indication (e.g., a Boolean value) in the class that an object of the class is a scent generating asset. In some embodiments, the system may store an indication of one or more scent properties in the class. For example, the system may store an identification of a scent produced by an object generated from the class.

In some embodiments, the system may determine information about the identified scent generating asset(s) in the XR environment. The information may include a measure of proximity between a user and the scent generating asset(s). For example, the measure of proximity may be a distance between the user and the scent generating asset(s) in the XR environment. In some embodiments, the information may include an indication of motion of the scent generating asset(s). For example, the information may include an indication of a speed, acceleration, and/or direction of movement of the scent generating asset(s) relative to the user in the XR environment. In some embodiments, the system may analyze the XR environment to determine a setting of the user. For example, the system may determine characteristics of the setting such as whether it is indoor or outdoor, climate, temperature, humidity, altitude, and/or other characteristics that may affect a user's experience of scent in the XR environment.

Next, process 1900 proceeds to block 1904 where the system determines spatial characteristics of an odor impression to be generated in the XR environment. In some embodiments, the system may determine spatial characteristics of the odor impression by determining one or more odorant components output into the XR environment. The odorant components may comprise virtual geometry that represents scent produced by the scent generating asset(s) in the XR environment. The virtual geometry may have motion in the XR environment. Collision of virtual geometry may represent interaction between multiple different scents from multiple scent generating assets. In some embodiments, the virtual geometry may be invisible to the user, and may be experienced through scent (e.g., an odor impression). The virtual geometry may provide a computerized model of scent produced by scent generating asset(s) in the XR environment. In some embodiments, the virtual geometry may include one or more shapes. For example, the shape(s) may include spheres, concentric spheres, cones, and/or other shapes. The shape(s) may represent one or more regions of scent in the XR environment. Examples of virtual geometry are described herein.

In some embodiments, the odorant components determined in the XR environment may be determined from analyzing the XR environment at block 1902. For example, the odorant components may be determined based on identification(s) of scent generating asset(s). In one implementation, a game engine may detect various objects in the XR environment. The game engine may determine one or more odorant components to be outputted in the XR environment. In some embodiments, the system may provide a set of predefined odorant component classes. The classes may be used to instantiate odorant component objects. For example, a game engine may instantiate an odorant components for scent generating assets in an XR environment. The system may obtain an indication of the odorant component(s) in the XR environment. In some embodiments, the system may obtain an indication of the odorant component(s) in the XR environment by receiving data from a game engine indicating the odor component(s). In some embodiments, the system may determine the odorant component(s) in the XR environment. For example, the system may analyze the XR environment (e.g., as described at block 1902) and determine odor components to be generated for scent generating asset(s) in the XR environment.

In some embodiments, the system may determine spatial characteristics of an odor impression from one or more parameters of the odorant components. For example, an odorant component may include an effusion rate (e.g., associated with a respective scent generating asset). The effusion rate may indicate a rate at which scent particles are being released from the scent generating asset. As another example, the parameter(s) may include a maximum scent intensity to be generated for an odorant component. The parameter(s) may include a base component mixture. For example, the system may determine multiple odorant components to generate in an XR environment for an odor impression. An example process 2100 of determining spatial characteristics of an odor impression is described herein with reference to FIG. 21. For example, the system may perform the steps at blocks 2102-2106 of process 2100 to determine the spatial characteristics of the odor impression.

Next, process 1900 proceeds to block 1906 where the system generates a command indicating the odor impression to be generated. In some embodiments, the command may indicate an identification of one or more scents to be generated, intensity of the scent(s), and duration of the scent(s). The system may encode the identification of the scent(s), intensity of the scent(s), and duration of the scent(s) in a command data structure. Examples of command data structures are described herein with reference to FIGS. 8A-B.

In some embodiments, the system may be configured to encode one or more intensity values and durations for respective scents in the command such that an odor impression having the determined spatial characteristics is experienced by a user in the XR environment as a result of execution of the command (e.g., by a controller). In some embodiments, the system may determine the intensity value(s) and the duration value(s) based on (1) virtual geometry determined by the system; and/or (2) a measure of proximity between the user and the scent generating asset(s). In some embodiments, an intensity value may be a value between 0 and 255. In some embodiments, an intensity value may be a value between 0 and 1. Some embodiments are not limited to a particular range values described herein. In some embodiments, the duration may be a time period for which to release a scent at a respective intensity. For example, the duration may be a number of seconds for which to release the scent at the respective intensity.

Next, process 1900 proceeds to block 1908 where the system transmits the command to a controller to generate the odor impression in the XR environment. In some embodiments, the system may be configured to transmit the command through a communication interface (e.g., a wireless or wired interface). For example, the system may transmit the command over a USB connection using a software API. As another example, the system may transmit the command over a Bluetooth connection. To illustrate, the game system 101 may transmit the command to a controller (e.g., olfactory stimulus system 102). The controller may execute the command and, as a result, control one or more scent generators (e.g., of piezoelectric device 105) to disperse one or more scented media according to the command. An example process by which the controller may execute a command is described herein with reference to FIG. 20.

After transmitting the command at block 1908, process 1900 ends.

Figure 20:
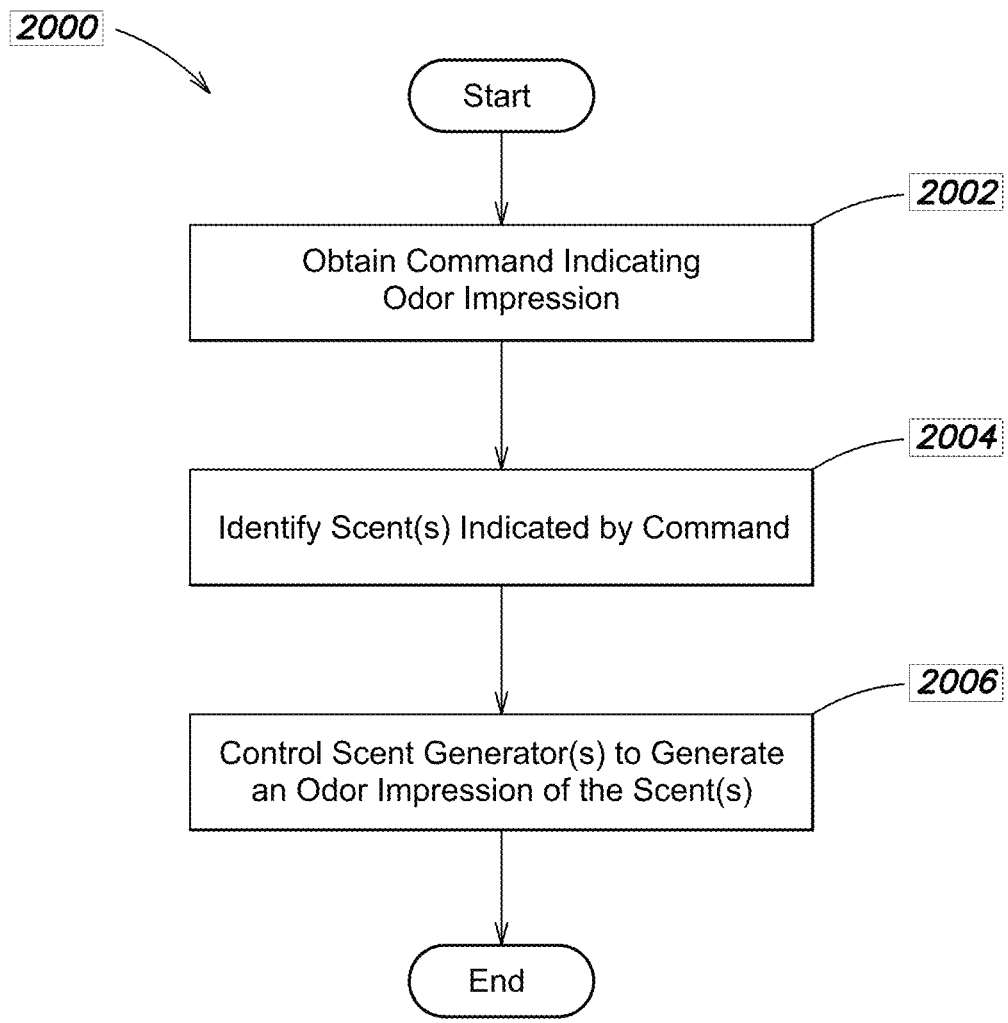
FIG. 20 shows an example process for executing an odor impression command according to some embodiments.

FIG. 20 shows an example process 2000 for executing an odor impression command according to some embodiments. Process 2000 may be performed by a controller. For example, the controller may be performed by processor 104 of olfactory stimulus system 102 described herein with reference to FIG. 1.

Process 2000 begins at block 2002 where the system obtains a command indicating an odor impression. For example, the system may obtain a command generated from performing process 1900 described above with reference to FIG. 19. The system may receive a transmitted command (e.g., from game system 101). In some embodiments, the system may obtain the command by requesting the command. For example, the system may periodically request new commands and, in response, receive new commands generated by the system. In some embodiments, the system may obtain the command from a software component of an olfactory stimulus system (e.g., embedded in a game engine). The system may obtain data indicating the command. Example command data structures that may be obtained by the system are described herein.

Next, process 2000 proceeds to block 2004 where the system identifies one or more scents indicated by the command. In some embodiments, the system may identify scent(s) indicated by the command by identifying scent identifier(s) encoded in the command. For example, the system may identify one or more alphanumeric strings in the command that are associated with respective scent(s). The system may determine the scent(s) that are to be dispersed based on the strings encoded in the command.

Next, process 2000 proceeds to block 2006 where the system controls one or more scent generators to generate an odor impression of the scent(s). The system may disperse the scent(s) at a respective intensity and duration indicated for each scent. For example, the system may disperse a scent for fire at an intensity of 200 for a duration of 15 seconds as indicated by the command. The system may control the scent generator(s) to disperse one or more scents to render the odor expression of the scent(s) for a user. For example, the system may control the scent generator(s) to render the odor expression of the scent(s) for a user interacting in an XR environment (e.g., a VR environment). In some embodiments, the system may control a scent generator using a piezoelectric device. Examples of piezoelectric devices are described herein.

In some embodiments, the system may store information for generating scents. The information may include instructions for generating respective scents. The system may execute the command by executing instructions stored for generating the scent(s) identified from the command. For example, the system may use an identifier of the scent to access instructions (e.g., from memory) for generating the scent(s). The system my execute the instructions to control the scent generator(s) to generate an odor impression of the scent(s).

In some embodiments, the system may generate an odor impression of a scent by releasing multiple scented mediums that, when combined, would result in the odor impression of the scent. The system may release multiple different scented mediums such that when the different scented mediums are sensed by an olfactory epithelium of a user, the user may experience a target sense indicated by the command. In some embodiments, the system may store information indicating a combination of scented mediums to use to release a respective scent. For example, the system may store instructions indicating a function for controlling each of multiple different scent generators to render a scent. In response to receiving a command indicating the scent, the system may execute the function for controlling the multiple different scent generators to render an odor impression of the scent. As an illustrative example, the system may identify a first scent from the command. In this example, the system may control (1) a first scent generator to disperse a second scent; and (2) a second scent generator to disperse a third scent. The second and third scent, when mixed at the olfactory epithelium of the user, may result in the odor impression of the first scent for the user.

In some embodiments, the system may control the scent generator(s) to release scent(s) according to the command by transmitting control signal(s) to the scent generator(s). For example, the system may transmit control signal(s) to a piezoelectric device that releases scented media through delivery hardware. The released scented media may be delivered to a nose (e.g., olfactory epithelium) of a user. For example, the delivery hardware may output scented media in an area around the user's nose. Examples of piezoelectric devices and delivery hardware are described herein. In some instances, the system may control multiple scent generators to release multiple scents that, when experienced by the user (e.g., at the user's olfactory epithelium), result in the odor impression of a scent.

After block 2006, process 2000 ends. For example, the system may stop dispersing scented media after it has executed the command.

Figure 21:
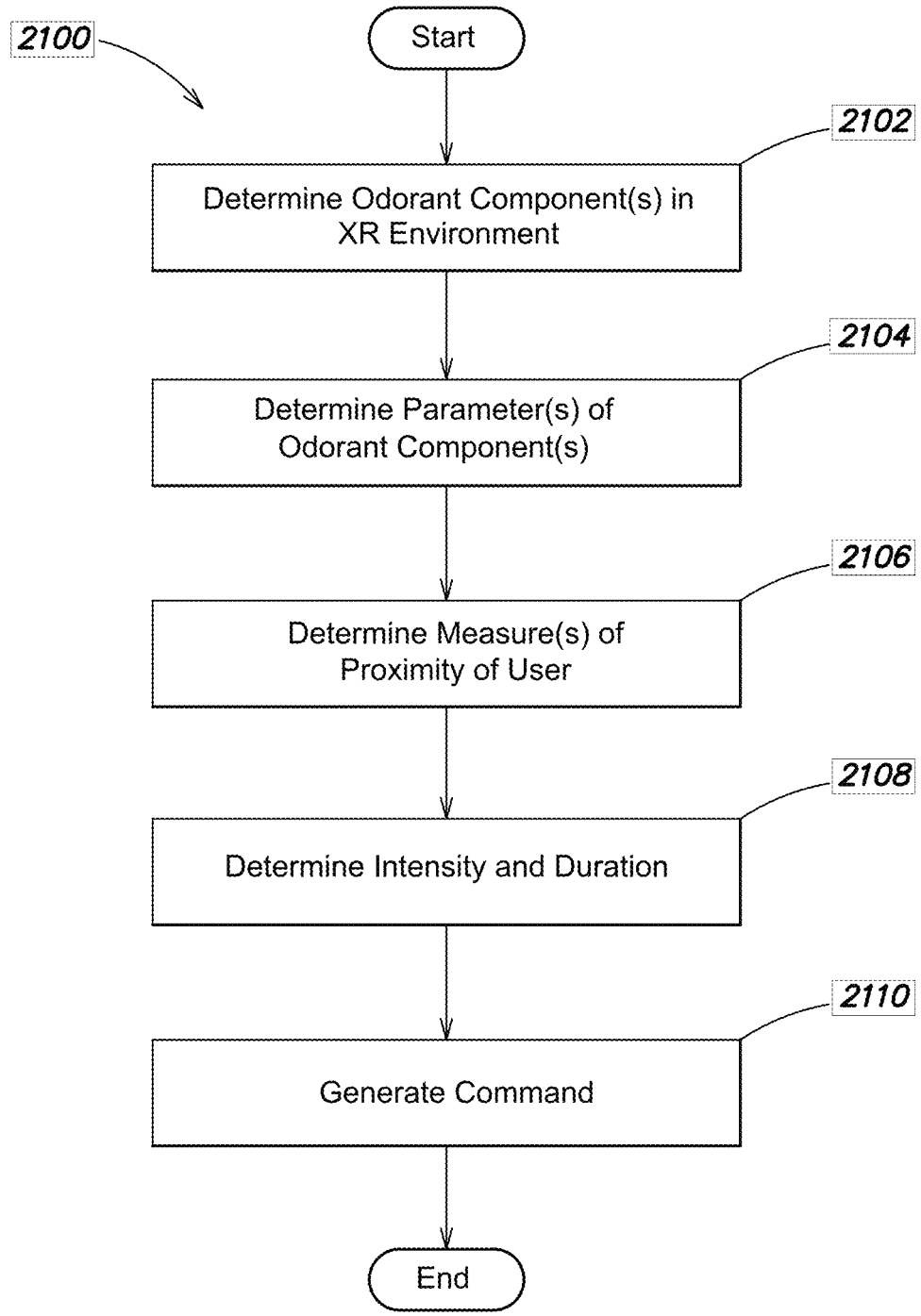
FIG. 21 shows an example process for generating a command for rending an odor impression command according to some embodiments.

FIG. 21 shows an example process 2100 for determining spatial characteristics of an odor impression and generating a command indicating the odor impression having the determined spatial characteristics, according to some embodiments. Process 2100 may be performed by any suitable computing system. For example, process 2100 may be performed by olfactory stimulus system 102 described here with reference to FIG. 1. A processor executing the software framework of the olfactory stimulus system 102 may perform the process. In some embodiments, process 2100 may be performed as part of process 1900 described herein with reference to FIG. 19. For example, process 2100 may be performed as part of blocks 1904-1906 of process 1900.

Process 2100 begins at block 2102, where the system determines one or more odorant components in an XR environment. The odorant component(s) may have been generated in the XR environment for one or more scent generating assets. For example, a game engine employing an architecture of scent framework may generate the odorant component(s) as software objects. In some embodiments, the system may determine the odor component(s) in the XR environment. For example, the system may identify one or more scent generating assets and generate odor component(s) in the XR environment for the identified scent generating asset(s). In some embodiments, each component may comprise a respective virtual geometry to be output in an XR environment (e.g., generated by game system 101). Virtual geometry may also be referred to herein as "geometry."

In some embodiments, the virtual geometry that the system outputs in the XR environment is invisible. The virtual geometry may be experienced by a user in the XR environment through generation of the odor impression. For example, as a user moves through the XR environment and collides with the virtual geometry, the system may generate an odor impression in which the user experiences the scent represented by the virtual geometry. Examples of virtual geometry are described herein.

Figure 22:
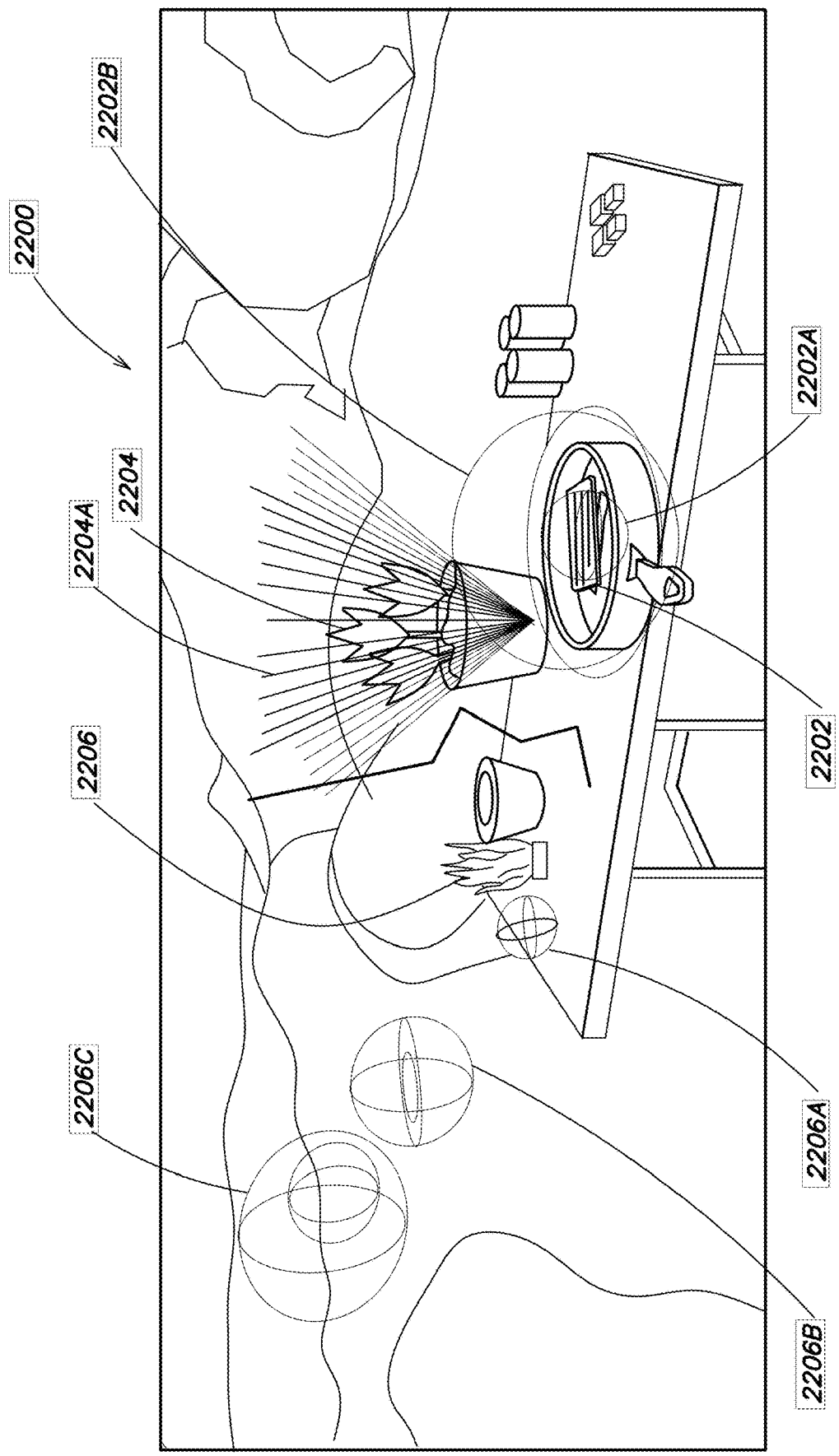
FIG. 22 shows an example depiction of generating virtual geometry in an XR environment according to some embodiments.

FIG. 22 shows an illustration 2200 of example virtual geometry of odorant components output in an XR environment, according to some embodiments. As shown in the illustration 2200, the XR environment includes various scent generating assets. The scent generating assets include food 2202 in a pan, a flower 2204, and a fire 2206. The XR environment includes various odorant components outputted (e.g., by a game engine) from the scent generating assets. The odorant components comprise geometry in the XR environment. In the example of FIG. 22, the geometry includes: (1) a first sphere 2202A and a second sphere 2202B outputted for the food 2202; (2) a cone shaped geometry 2204A outputted for the flower 2204; and (3) three spheres 2206A-C outputted for the fire 2206. The virtual geometry may represent scent in the XR environment produced from the scent generating assets. In some embodiments, the virtual geometry may collide with other virtual geometry. For example, referring again to the example of FIG. 22, the virtual geometry 2202A associated with the food 2202 in the XR environment may move and collide with virtual geometry 2204A associated with the flower 2204. The system may use collision of geometry to indicate interactions between multiple different scents from different scent generating assets (e.g., the food 2202 and the flower 2204).

In some embodiments, each component may provide a respective scent style. In some embodiments, a first component may provide an ambient scent, a second component may provide a burst scent, a third component may provide a specific scent, and a fourth component may provide a background scent. An ambient scent is one that may represent scent from an overall environment of a user in the XR environment. In some embodiments, an ambient component may have a low intensity (e.g., less than 50). The ambient component may further have a low rate of decay (e.g., greater than 1 unit of intensity per minute). As an example, when the user has remained in an area for greater than a length of time (e.g., two minutes), the system may output the first component to generate an ambient scent in the XR environment. A burst scent may be one that is triggered when a user enters an area of influence of a scent generating asset. The scent from a burst may increase initially and then decrease with time. In one implementation, the intensity resulting from a burst scent may be a bell curve. For example, when a user first becomes proximate a scent generating asset (e.g., by opening a garbage can), the system may determine to use a burst component. When the user first becomes proximate the scent generating asset, an intensity of scent may increase followed by a decrease in intensity. A specific scent may be one that occurs when a user deliberately interacts with a scent generating asset to smell it. For example, the user may deliberately smell the asset (e.g., a flower). Examples of components respective styles of scent provided are described herein.

Next, process 2100 proceeds to block 2104 where the system determines one or more parameters of the odorant component(s). In some embodiments, the parameter(s) may indicate properties of the virtual geometry and, in turn, affect a scent experience provided by the virtual geometry (e.g., when the user collides with the virtual geometry in the XR environment). The parameter(s) may include spatial dimensions of the geometry of an odorant component. For example, a first odorant component may comprise spherical geometry including two concentric spheres. Parameters for the spherical geometry may include a first radius of the inner sphere and a second radius for the outer sphere. As another example, a second odorant component may comprise box geometry. Parameters for the box geometry may include a length, width, and height of a rectangular prism space in the XR environment in which scent from one or more scent generating assets exists. Example odorant components and respective parameters are described herein with reference to FIGS. 24A-28B.

In some embodiments, the parameter(s) may include a maximum intensity for the virtual geometry. In one implementation, the system may include a maximum intensity of scent that may be experienced from interaction with a geometric component. The parameter(s) may include parameters specifying a scaling function for determining one or more scalars to apply to the maximum intensity (e.g., by multiplication) to obtain an intensity. The system may determine the value of the scaling function based on a user's location in the XR environment relative to the virtual geometry. For example, the scaling function may be determined from a location of a user between an inner sphere and an outer sphere of spherical geometry. In another example, the scaling function may be determined from an angle of the user relative to an axis of the virtual geometry. Examples of scaling functions are described herein. In some embodiments, the parameter(s) may include a rate of decay of intensity. For example, the parameter(s) may specify a function of time indicating a rate at which intensity of scent for an odorant component is to decrease. The parameter(s) may include dimensions of virtual geometry of odor component(s). The parameter(s) may include an offset of the virtual geometry (e.g., relative to a scent generating asset that the virtual geometry is associated with). The parameter(s) may include an effusion rate of scent particles (e.g., in meters per second).

Next, process 2100 proceeds to block 2106 where the system determines a measure of proximity of the user. In some embodiments, the system may determine a measure of proximity between the user and one or more scent generating assets in the XR environment. For example, referring to the example shown in FIG. 22, the system may determine a measure of proximity between the user and each of the food 2202, the flower 2204, and the fire 2206. In some embodiments, the system may determine the measure of proximity of the user relative to one or more portions of virtual geometry in the XR environment. For example, referring to the example shown in FIG. 22, the system may determine a measure of proximity of the user to the geometry 2202A-B, 2204A-B, and/or 2206A-C. In some embodiments, the measure of proximity may be a distance in the XR environment between the user and the portion(s) of the geometry. For example, the system may determine a distance between the user and the center of the inner sphere of virtual geometry 2206C in FIG. 22. In another example, the system may determine a location of the user relative to the two concentric spheres (e.g., within the inner sphere, a location between the inner sphere and outer sphere, or outside of the outer sphere). In another example, the system may determine a location of the user relative to a set of concentric cones. In this example, the system may determine (1) whether the user is inside the inner cone; (2) a location of the user between the inner cone and the other cone; or (2) whether the user is outside of the outer cone. In some embodiments, the measure of proximity of the user may be an angular displacement of the user relative to an axis or direction. For example, the measure of proximity of the user may be an angular displacement (e.g., in degrees) between a direction of scent diffusion and the user.

In some embodiments, the system may determine the measure of proximity of the user using an olfactory epithelium component. The olfactory epithelium component may be an element in the XR environment representing a user's nose. The location of the olfactory epithelium may be tracked by the system. The system may determine the measure of proximity of the user using a position of the olfactory epithelium in the XR environment. For example, the system may determine the measure of proximity by determining a distance between the position of the olfactory epithelium and a position of a scent generating asset.

Next, process 2100 proceeds to block 2108 where the system determines one or more intensity and duration values. In some embodiments, the system may determine the intensity and duration value(s) using the measure(s) of proximity of the user and the parameter(s) of the odorant component(s). In some embodiments, the system may determine intensity based on a measure of proximity of the user (e.g., distance to a scent generating asset). For example, the system may use the measure of proximity to determine a scalar. In some embodiments, the system may determine intensity based on time. For example, the system may determine a scalar value based on a decay function of time. In some embodiments, the system may determine intensity based on an angle of the user relative to a direction of scent in an odorant component. The system may use an angular offset to determine a directional scalar. The system may apply one or more scalars to a maximum intensity of an odorant component (e.g., by multiplication) to obtain an output intensity (e.g., that is encoded in a command). In some embodiments, the system may apply any combination of one or more scalars described herein to a maximum intensity (e.g., by multiplication) to obtain the output intensity. In some embodiments, the system may determine an intensity based on whether a user is within boundaries of geometry of an odorant component. For example, if the system may determine a scalar value based on a location of the user relative to the geometry.

In some embodiments, the system may use a function to obtain output indicating intensity value(s) and duration(s) of the intensity value(s). The system may determine inputs to the function based on parameters of an odorant component, a measure of proximity of the user, and/or a location of the user relative to the odorant component. In some embodiments, the system may use a respective function for each type of component. For example, the system may use a first function for a first component, a second function for a second component, and a third function for a third component. As an illustrative example, the system may determine an odorant component with concentric spheres for a scent generating asset in the XR environment. The system may specify a nominal intensity of 100 for the odorant component. The system may (1) multiply the nominal intensity by 1.25 if the user (e.g., olfactory epithelium) is determined to be within the inner sphere; (2) apply a multiplicative scalar between 0 and 1 when the user is between the inner sphere and the outer sphere; and (3) apply a multiplicative scalar of 0 when the user is outside of the outer sphere. Other example calculations of intensity for various types of geometry are described herein.

In some embodiments, the system may continuously obtain intensity and duration values. For example, the system may provide input to the function periodically (e.g., every millisecond or second) to obtain intensity and duration value(s). The system may thus generate odor impressions as a user interacts in an XR environment. In some embodiments, the system may generate duration value(s) based on parameters of an odorant component. For example, the system may generate the duration value(s) based a time period that the user is within boundaries of geometry of the odorant component.

Next, process 2100 proceeds to block 2110 where the system generates a command. The system may generate a command as described at block 1906 of process 1900, described herein with reference to FIG. 19. For example, the system may encode the determined intensity and duration value(s) in a command data structure (e.g., as described herein with reference to FIGS. 8A-B). The command may indicate one or more scents to be dispersed with a corresponding intensity and duration for each scent. For example, the system may encode in the command that (1) a first scent is to be dispersed with an intensity of 125 for a period of 2 seconds; and (2) a second scent is to be dispersed with an intensity of 35 for a period of 1 second.

After block 2110, process 2100 ends. For example, the system may transmit the command to a controller for execution (e.g., as described in process 2000 described herein with reference to FIG. 20). The controller may execute the command to generate an odor impression in an XR environment.

Figure 24A:
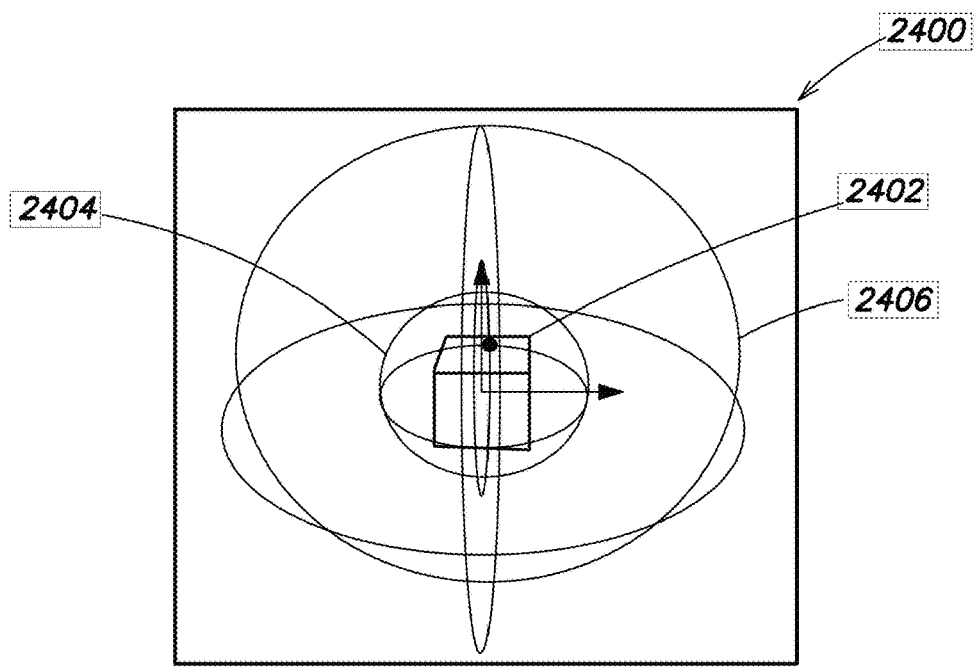
FIGS. 24A-B show views of an example odorant component with spherical geometry, according to some embodiments.

FIG. 24A shows a perspective view 2400 of an odorant component with spherical geometry, according to some embodiments. The odorant component is associated with a scent generation asset 2402. For example, the scent generating asset 2402 may be an object in an XR environment. The spherical geometry of the odorant component includes an inner sphere 2404 and an outer sphere. The spheres may represent boundaries of areas in an XR environment where a user may experience one or more scents.

Figure 24B:
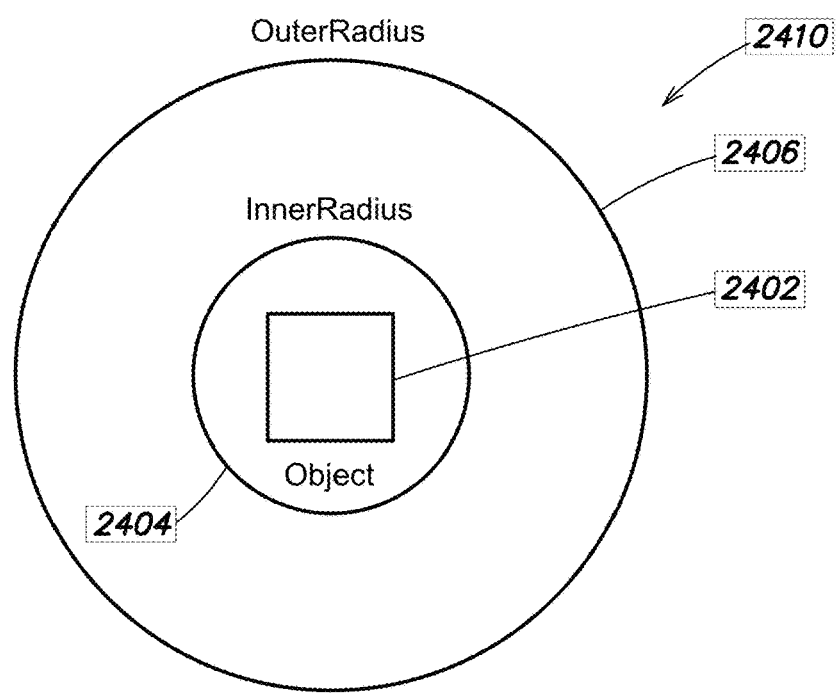

FIG. 24B shows an aerial view 2410 of the odorant component of FIG. 24A. As shown in FIG. 24B, the odorant component includes: (1) an inner radius defined by the inner sphere 2404; and (2) an outer radius defined by the outer sphere 2406. A user may experience scent from the object 2402 when the user is within outer sphere 2406 of the odorant component. In some embodiments, the system may determine an intensity of one or more scents to be output (e.g., by olfactory stimulus system 102) according to a measure of proximity of the user to the object 2402. The system may store a maximum intensity for the odorant component (e.g., specified by a value between 0 to 255, or a value between 0 and 1). The system may use a function to adjust the maximum intensity based on the relative location of the user to the odorant component determined from the measure of proximity. When the user is within the inner sphere 2404, the system may output the maximum intensity (e.g., encode the maximum intensity value in a command). When the user is between the inner sphere 2404 and the outer sphere 2406, the system may (1) use a function to determine a scalar; and (2) apply the scalar to the maximum intensity to obtain an output intensity. For example, the function may be a linear function that outputs a value between 0 and 1 based on a relative location of the user between the inner sphere 2404 and the outer sphere 2406. In this example, the function may output 1 when the user is located at the boundary of the inner sphere 2404 and output 0 when the user is located at the boundary of the outer sphere 2406. In some embodiments, the system may use a nonlinear function for determining a scalar, as embodiments are not limited in this respect. The system may output the scaled intensity value (e.g., by encoding the scaled intensity value in a command).

In some embodiments, the system may determine one or more parameters for the odorant component of FIGS. 24A-B. The parameter(s) may include a maximum intensity, radius of an inner sphere, and/or radius of an outer sphere. In some embodiments, the parameter(s) may include parameters defining a function for determining a scalar. For example, the parameters may include a slope and intercept of a linear function for calculating a scalar as a function of radial distance of the user from the inner sphere. In some embodiments, the parameter(s) may include an offset of the geometry. The offset may indicate an offset of the geometry relative to the object 2402. For example, an offset of (0, 0, 0) may indicate that the spheres are positioned such that the object 2402 is at the center of the inner sphere 2404. In another example, an offset of (0, 1, 0) may indicate that the geometry is offset by one unit (e.g., of distance) in a direction (e.g., along a y-axis) from the object 2402.

Figure 25A:
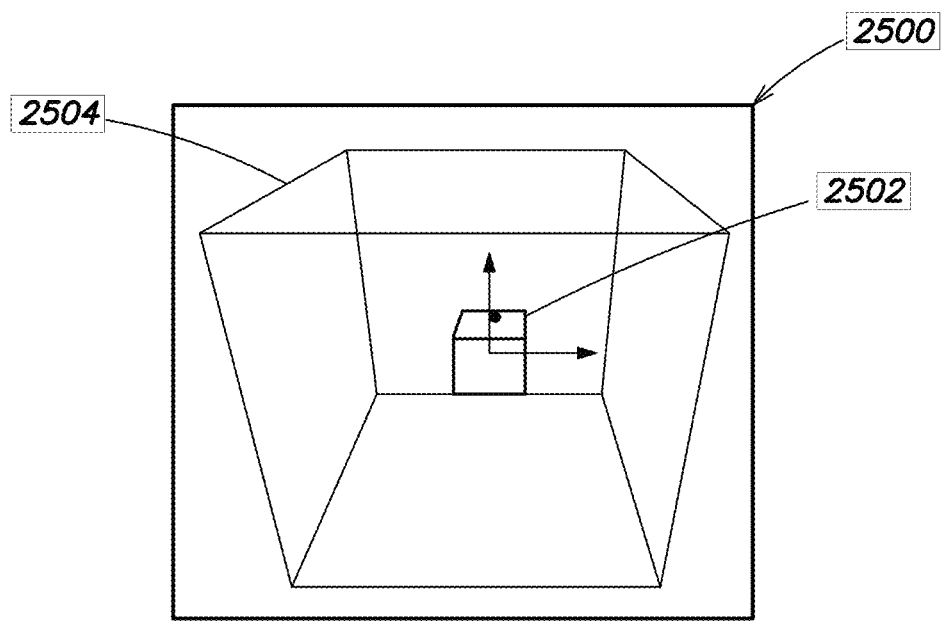
FIGS. 25A-B show views of an example odorant component with box geometry, according to some embodiments.

FIG. 25A shows a perspective view 2500 of an odorant component with box geometry, according to some embodiments. The odorant component is associated with a scent generation asset 2502. For example, the scent generating asset 2502 may be an object in an XR environment. In some embodiments, the scent generating asset may not be a visible object in an XR environment. For example, the system may determine a scent generating asset to be a virtual scent source representing multiple scents in a setting of the XR environment. The box geometry of the odorant component includes a box 2504. The box 2504 may represent an area in an XR environment where a user may experience one or more scents.

Figure 25B:
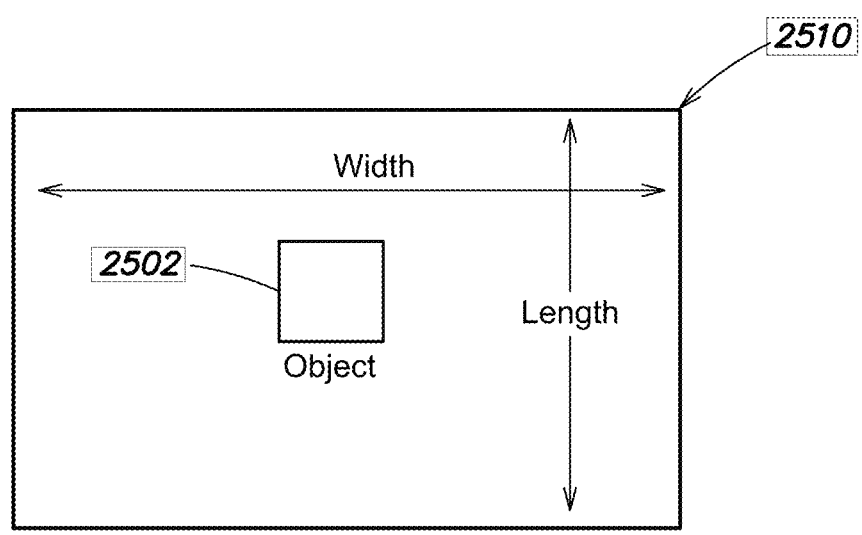

FIG. 25B shows an aerial view 2510 of the odorant component of FIG. 25A. As shown in FIG. 25B, the odorant component includes a box with respective dimensions (e.g., length, width, and height). A user may experience scent from the object 2502 when the user is within the box 2504. In some embodiments, the system may determine an intensity of one or more scents to be output (e.g., by olfactory stimulus system 102) to be a constant and/or slow decaying intensity (e.g., less than 5 units of intensity per second) when the user is within the boundary defined by the box 2504. For example, the system may determine a single intensity value of 100 when the user is in the box 2504. As another example, the system may determine an intensity that begins at 100 and decays at a rate of 0.1/second.

In some embodiments, the system may be configured to determine one or more parameters for the odorant component of FIGS. 25A-B. The parameter(s) may include a scent intensity when the user is inside the box 2504, dimensions of the box (e.g., length, width, and height), and/or an offset of the box (e.g., relative to a scent generating asset). The offset may indicate an offset of the geometry relative to the object 2502. The offset may be indicated by a vector originating at the object 2502. For example, an offset of (0, 0, 0) may indicate that the box is positioned such that the object 2502 is at the center of the box 2504. In another example, an offset of (0, 1, 0) may indicate that the geometry is offset by 0 units along a first axis (e.g., x-axis), 1 unit along a second axis (e.g., y-axis), and 0 units along a third axis (e.g., z-axis).

In some embodiments, the box geometry may be used for background scents. For example, the intensity for box geometry may be low to create an odor impression of a background scent in an XR environment. In some embodiments, multiple boxes associated with different respective scent generating assets may overlap to generate an odor impression of the scents. For example, multiple boxes may overlap to define a region in an XR environment of multiple scents.

Figure 26A:
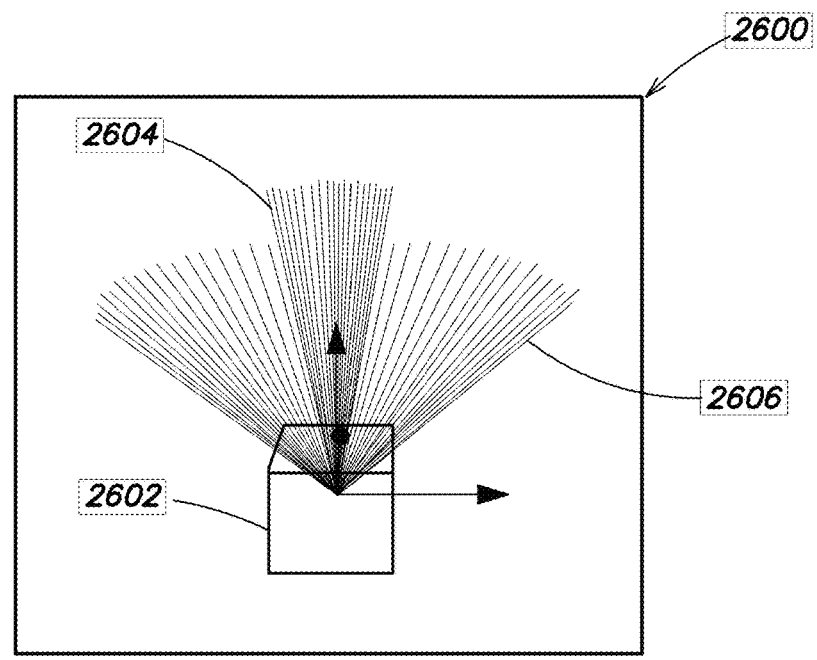
FIGS. 26A-B show views of an example odorant component with cone geometry, according to some embodiments.

FIG. 26A shows a view 2600 of an odorant component with cone geometry, according to some embodiments. As shown in FIG. 26A, the odorant component is associated with a scent generating asset 2602. For example, the odorant component may represent scent originating from the scent generating asset 2602. The odorant component includes an inner cone 2604 and an outer cone 2606.

Figure 26B:
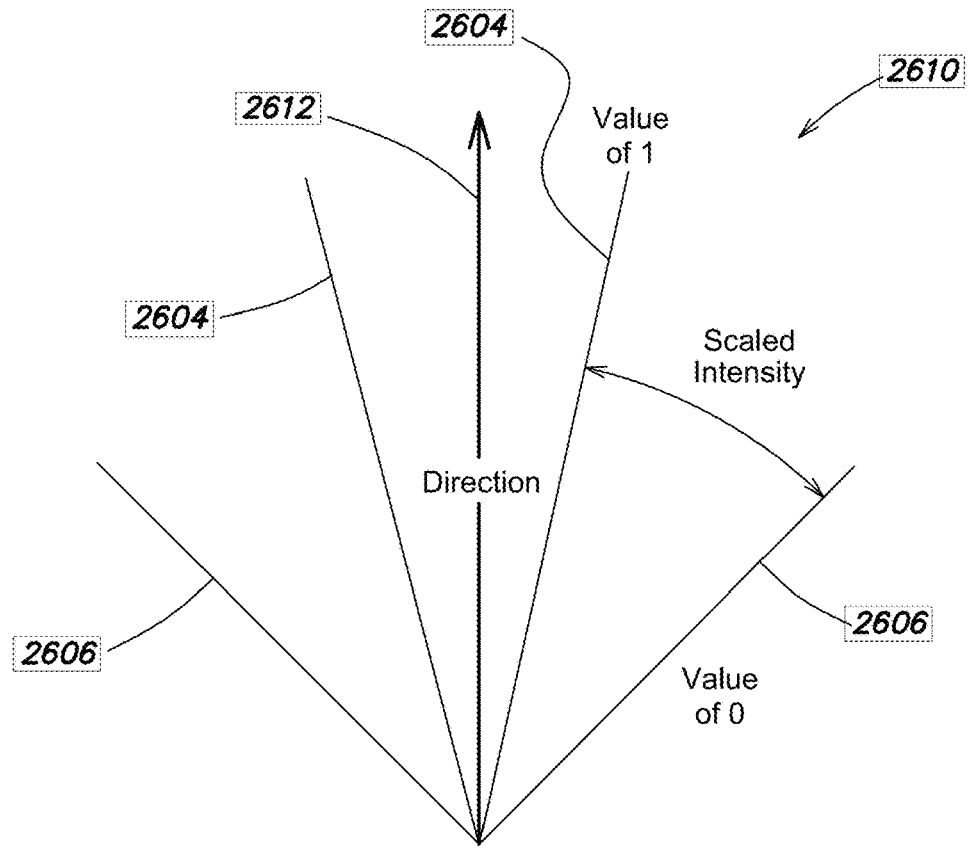

FIG. 26B shows a side view 2610 of the odorant component shown in FIG. 26A, according to some embodiments. The view 2610 shows a direction 2612 of scent dispersal from the scent generating asset 2602. The inner cone 2604 and the outer cone 2606 may be used by the system to define regions of scent intensity based on a measure of proximity of the user. In the example of FIG. 26B, the scent intensity may be scaled according to an angular offset of the user from the direction of the scent. The direction of the scent may be defined by a vector originating from the object 2602. For example, a vector of (0, 3, 0) may indicate a vector 3 units in length along a y-axis originating at the object 2602. The system may store a maximum intensity for the odorant component (e.g., specified by a value between 0 to 255, or a value between 0 and 1). The system may adjust the maximum intensity based on the relative location of the user to the odorant component determined from the measure of proximity (e.g., angular offset from the direction vector 2612 and/or distance from scent generating asset 2602). When the user is within the inner cone 2604, the system may output the maximum intensity (e.g., encode the maximum intensity value in a command). When an angle of the user is between the inner cone 2604 and the outer cone 2606, the system may (1) determine a scalar; and (2) apply the scalar to the maximum intensity to obtain an output intensity. For example, the system may use a linear function that outputs a value between 0 and 1 based on an angle of the user between the inner cone 2604 and the outer cone 2606. In this example, the function may output 1 when the user is located at the boundary of the inner cone 2604 and output 0 when the user is located at the boundary of the outer cone 2606. In some embodiments, the system may use a non-linear function for determining a scalar, as embodiments are not limited in this respect. The system may output the scaled intensity value (e.g., by encoding the scaled intensity value in a command).

In some embodiments, the system may be configured to determine one or more parameters for the odorant component of FIGS. 26A-B. The parameter(s) may include a maximum intensity, an inner cone angle, and an outer cone angle. In some embodiments, the parameter(s) may include parameters defining one or more functions for determining a scalar. For example, the parameters may include a slope and intercept of a linear function for calculating a scalar as a function of angle of the user from the direction vector 2612. As an illustrative example, the geometry may have an inner cone angle of 10 degrees from the direction vector 2612 and an outer cone angle of 45 degrees from the direction vector 2612. When a user is 10 degrees or less from the direction vector 2612, the scalar may have a value of 1. When the user is between 10 degrees and 45 degrees (i.e., e.g., between the inner cone 2604 and outer cone 2606), the scalar may be determined as a function (e.g., a linear function) of the user's angle (e.g., in degrees). When the user is beyond the 45 degrees (i.e., outside of the outer cone 2606), the scalar may be 0. In some embodiments, the parameter(s) may include parameters defining a scalar based on a distance of the user from the object 2602. For example, the parameters may include a slope and intercept of a function for calculating the scalar.

In some embodiments, the parameter(s) may include an offset of the geometry. The offset may indicate an offset of the geometry relative to the object 2602. For example, an offset of (0, 0, 0) may indicate that the apex of the cones is positioned at the center of the object 2602. In another example, an offset of (0, 1, 0) may indicate that the geometry is offset by one unit (e.g., of distance) in a direction (e.g., along a y-axis) from the object 2602.

In some embodiments, the system may be configured to use the odorant component with cone geometry (e.g., as illustrated in FIGS. 26A-B) when the user intentionally smells a scent generating asset. For example, the system may use an odorant component with cone geometry to represent scent experienced by the user when deliberately smelling an object in an XR environment. The cones may define regions of scent diffusion when the user is smelling the object.

Figure 27B:
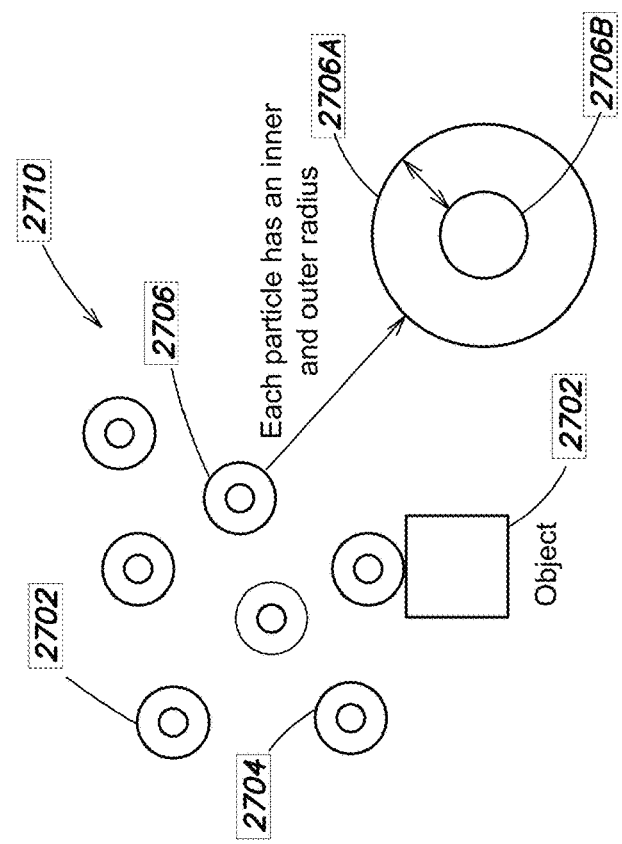
FIGS. 27A-B show views of an example odorant component with multiple spherical particle geometry, according to some embodiments.
Figure 27A:
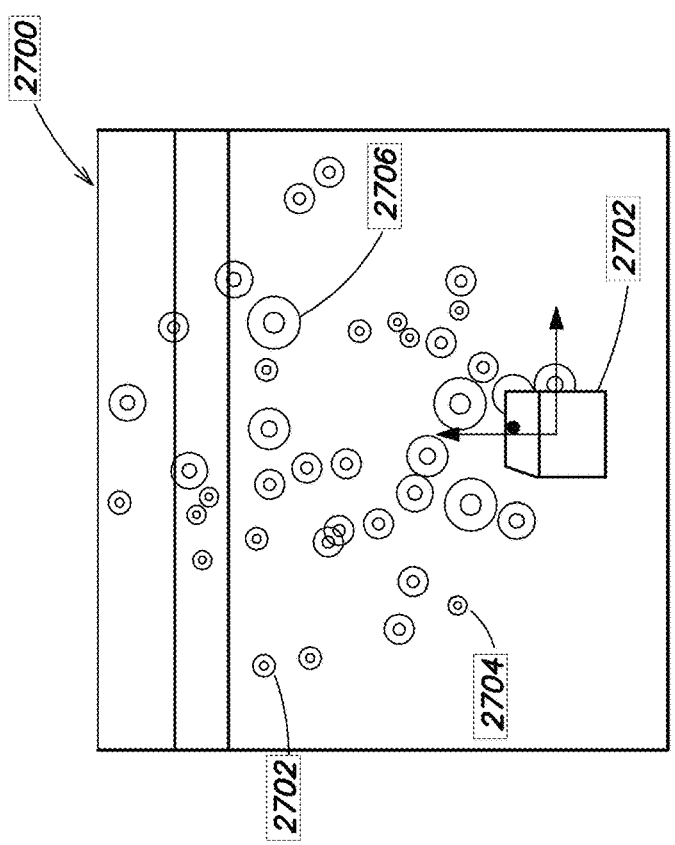

FIG. 27A shows a view 2700 of an odorant component with multiple spherical particles, according to some embodiments. As shown in FIG. 27A, the odorant component is associated with a scent generating asset 2702. For example, the odorant component may represent scent originating from an object in an XR environment. The odorant component has a plurality of particles including particles 2704, 2706, and 2708. In some embodiments, the particles (e.g., particles 2704-2708) may disperse from the scent generating asset 2702. For example, the particles may disperse radially throughout an environment from the scent generating asset 2702.

FIG. 27B shows an aerial view 2710 of the odorant component of FIG. 27A, according to some embodiments. As illustrated in the example of FIG. 27B, each of the particles of the odorant component comprises an inner sphere and an outer sphere. For example, the particle 2708 includes an outer sphere having an outer radius 2708A and an inner sphere having an inner radius 2708B. In some embodiments, each of the particles may have the same dimensions. In some embodiments, each of the particles may have different dimensions.

In some embodiments, a user may experience scent from the object 2702 when the user is within an outer sphere of a particle of the odorant component. In some embodiments, the system may determine an intensity of one or more scents to be output (e.g., by olfactory stimulus system 102) according to a measure of proximity of the user to the object 2702. The system may store a maximum intensity for the odorant component (e.g., specified by a value between 0 to 255, or a value between 0 and 1). The system may use a function to adjust the maximum intensity based on the relative location of the user to a particle of the odorant component determined from the measure of proximity. When the user is within the inner sphere of a particle (e.g., 2708B), the system may output the maximum intensity (e.g., encode the maximum intensity value in a command). When the user is between the inner sphere (e.g., 2708B) and the outer sphere (e.g., 2708A), the system may (1) use a function to determine a scalar; and (2) apply the scalar to the maximum intensity to obtain an output intensity. For example, the function may be a linear function that outputs a value between 0 and 1 based on a relative location of the user between the inner sphere 2708B and the outer sphere 2708A. In this example, the function may output 1 when the user is located at the boundary of the inner sphere 2708B and output 0 when the user is located at the boundary of the outer sphere 2708A. In some embodiments, the system may use a non-linear function for determining a scalar, as embodiments are not limited in this respect. The system may output the scaled intensity value (e.g., by encoding the scaled intensity value in a command).

In some embodiments, the system may determine one or more parameters for the odorant component of FIGS. 27A-B. The parameter(s) may include a maximum intensity, radius of an inner sphere(s), and/or radius of an outer sphere(s). In some embodiments, the parameter(s) may include parameters defining a function for determining a scalar. For example, the parameters may include a slope and intercept of a linear function for calculating a scalar as a function of radial distance of the user from the inner sphere. In some embodiments, the parameter(s) may include parameters indicating a movement of the particles (e.g., in an XR environment). For example, the parameter(s) may include a velocity, acceleration, and/or deceleration of the particles. In some embodiments, the system may be configured to use an odorant component with multiple particles for generating an odor impression of scent dispersing in different directions. For example, the system may use the odorant component illustrated in FIGS. 27A-B to generate an odor impression from a fire in an XR environment (e.g., as shown in FIG. 22).

Figure 28A:
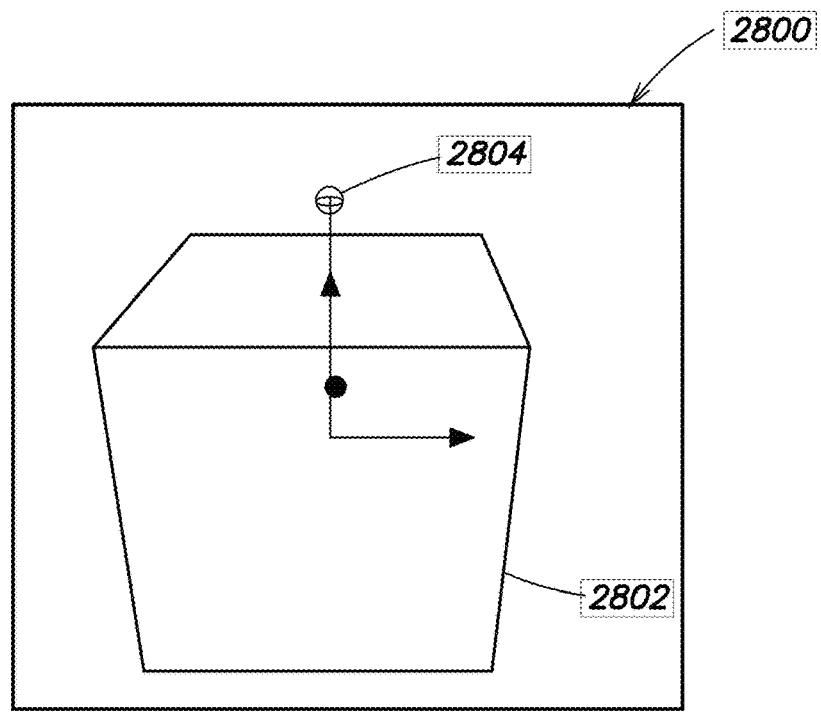
FIGS. 28A-B show views of an example odorant component with expanding spherical geometry, according to some embodiments.

FIG. 28A shows a view 2800 of an odorant component with expanding spherical geometry. The view 2800 shows a scent generating asset 2802 and a location 2804 from which the spherical geometry of the odorant component will expand. The odorant component 2804 may be placed proximate the scent generating asset 2802. In some embodiments, the system may cause the odorant sphere to expand in response to detection of an action in an XR environment. As an illustrative example, the system may trigger the expansion in response to detecting that the user has opened a trash can. The system may execute a function to trigger the expansion.

Figure 28B:
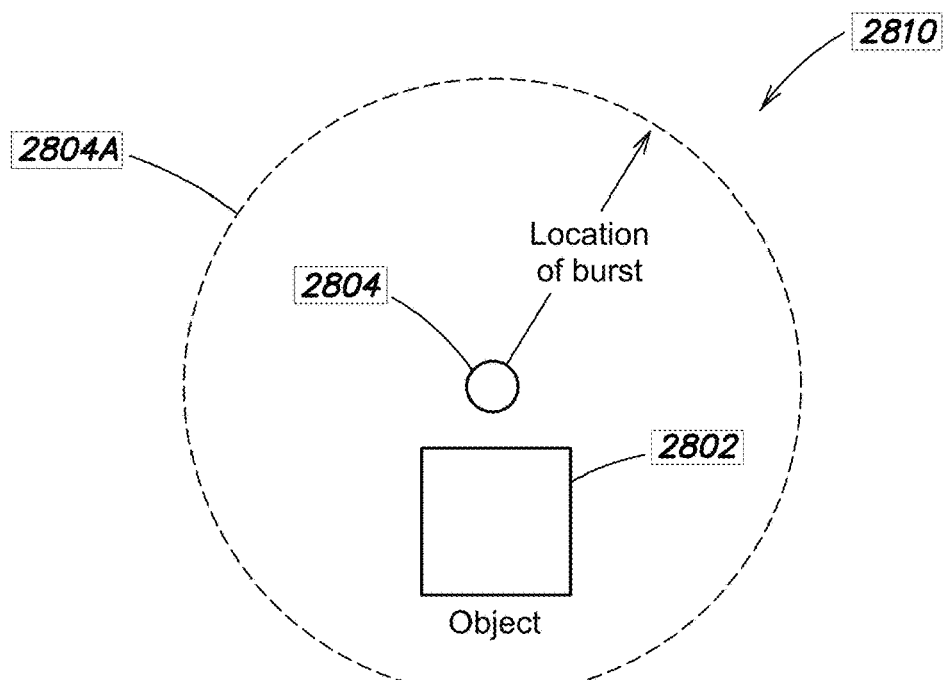

FIG. 28B shows an aerial view 2810 of the expanding geometry of the odorant component. As shown in FIG. 28B, the sphere expands from the location of the burst 2804 as indicated by the radial arrow. The radius 2804A of the sphere expands as indicated by the dotted lines. In some embodiments, the rate of expansion may be specified by an effusion rate (e.g., in meters/second). In some embodiments, the odorant component may include one or more parameters indicating properties of the odorant component. The parameter(s) may include an effusion rate indicating a rate of expansion. The parameter(s) may include an offset indicating an offset of the burst location relative to the scent generating asset 2802. For example, the parameter(s) may include an offset vector (0, 1, 0) indicating a location of the burst location 2804 relative to the scent generating asset 2802 that is one unit along a y-axis originating at the scent generating asset 2802. Although the example of FIG. 28B shows the location of the burst offset from the location of the scent generating asset 2802, the system may additionally and/or alternatively use a location of the scent generating asset 2802 as the location of the burst.

In some embodiments, an odorant component may include one or more parameters indicating a rate of decay of scent for the odorant component. For example, the parameter(s) may indicate an exponential function at which the intensity of a scent decays with respect to time. In some embodiments, an odorant component may include a respective function which the system may use to determine an intensity. The function may include one or more inputs determined by the system using parameters of the odorant component and a measure of proximity of the user. For example, a function may be a product of one or more scalars and a maximum intensity.

Odorant components described herein are provided for illustrative purposes. In some embodiments, the system may use other odorant components not described herein. Parameters of odor components described herein are provided for illustrative purposes. In some embodiments, odor components may include parameters in place of and/or in place of parameters described herein.

Figure 29:
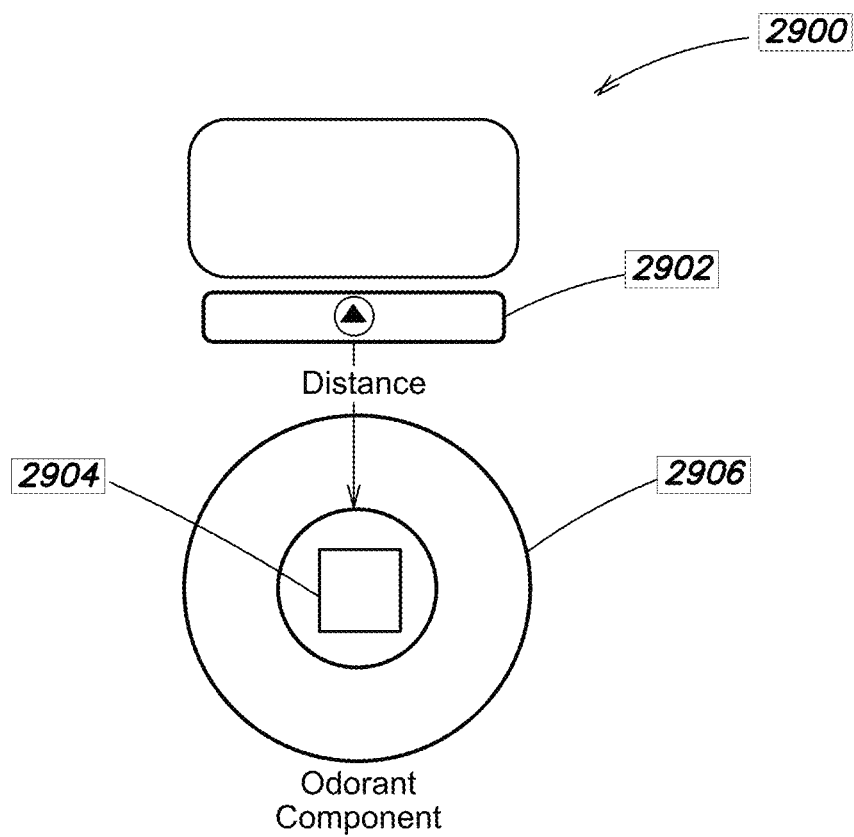
FIG. 29 shows a view of an olfactory epithelium located proximate an odorant component, according to some embodiments.

FIG. 29 shows a view 2900 of an olfactory epithelium 2902 located proximate an odorant component 2906, according to some embodiments. The olfactory epithelium 2902 may represent a user (e.g., in an XR environment). For example, the system may use the location of the olfactory epithelium 2902 in an XR environment for generating an odor expression (e.g., by determining spatial characteristics and/or generating a command to render the odor expression). In the example of FIG. 29, the olfactory epithelium 2902 is located proximate a spherical odorant component 2906 associated with a scent generating asset 2904. As the olfactory epithelium 2902 is located outside of the outer sphere of the odorant component 2906, the system may determine that no scent is to be output (e.g., by determining an intensity value of 0). If the olfactory epithelium 2902 were to enter the outer sphere of the odorant component 2906, the system may determine an intensity value greater than 0 for an odor expression (e.g., as described with reference to FIGS. 24A-B).

Scent Mechanics

Spectrum Of Odorant Appeal

Humans are born with a neutral disposition to almost every odorant. In fact, babies love every smell with the exception of irritants and certain toxic chemicals. Most of our attraction to (or aversion of) smells is learned behavior. Some of these learned behaviors are cultural, some are taught to us by family and peers, while others are from personal experience. These very personal and very subjective experiences create scent/memory associations that are very powerful and can include everything from fond memories of Grandma's chocolate cake on one end of the spectrum to violence and sexual trauma on the other end of the spectrum. We can never know how an individual will react to a particular odorant or set odorants and they might not either; however, there are some assumptions we can make about what is appealing and not appealing to the general public that is backed up by scientific and anecdotal evidence. We can classify odors on two ends of a spectrum: "Inviting" or "Warning."

5 Phases of Olfaction

The process of olfaction is fascinating and complex. It begins outside our bodies independent of us, biochemically stimulates our OE subconsciously, and ends in extremely personal thoughts, emotions and behaviors. It is important to recognize the distinct phases that take place during olfaction and the moment our experience crosses from external, to internal, to cognitive, then to behavioral. The Architecture of Scent breaks this process into 5 phases:

Release of Odorant:

Most things in our world smell. That is to say they contain at least a small amount of volatile organic compounds (VOC) that, due to their physical properties, are always evaporating into the air. Even things like metal that, technically speaking, contain no VOCs (and so cannot have an odor) generally have collected dirt, oil or some organic material that can produce an odor. Odorants vary in size but are almost always too small to see and usually fall in the range of a single or cluster of molecules about 6 nanometers in diameter.

Stimulation of the Olfactory Epithelium:

When one or a number of these odorant molecules enter the nose or the mouth they are likely to collide with the olfactory epithelium. There are thousands of tiny hairs (cilia) that can sense the presence of an odorant and send an electrochemical signal through the OE to the limbic system in our brains that translates the signal.

Perception of Odor by Brain:

When the brain receives the signal through the OE generated by the odorant, it interprets the signal and gives it meaning. Generally speaking, the area of our brain responsible for interpreting the meaning of these odorants operates on a subconscious level and, although they can influence our cognition and behavior, we may not be consciously aware of the affect. There are 3 categories of olfactory motivation: social, environmental, gustatory.

Cognition of Odor:

The area of our brain that processes odor also processes memory and emotion, therefore most odorants either create or reference a "scent memory." When an odorant is in high enough concentration, is dangerous, or memorable, our cognitive brains become aware of its presence and it becomes "recognizable"

Behavior Based on Odor:

Whether or not we are cognitively aware of the odor it will still affect our thoughts, feelings and behavior. Sometimes subtly and sometimes dramatically. The smell of bacon cooking might stimulate hunger, the smell of rotting food will stimulate disgust and the imperceptible smell of pheromones may cause lust and attraction. Odor influences thoughts and thoughts influence behavior.

Proximity Based Scent Algorithms

AMBIENT: An ambient smell is one that is representative of the overall environment. Ambient scents are usually low-level output and follow the undulating algorithm. Due to the potential long length of time the user may be exposed to an ambient smell, special consideration must be taken to limit olfactory fatigue or oversaturation of airspace.

BURST/PROXIMITY: A burst scent is associated with an asset and will trigger when the user breaches the exterior of the sphere of influence and increase or decrease proportionally to the nucleus of the asset. The strength tends to be medium level intensity and follow the "bell curve" type of dispersion. A patchwork of burst smells may create a layered aromatic effect for maximum immersion. Burst smells are generally not items that are immediately identified as interactable but the combination of visual, olfactory and auditory cues can lead the user to the conclusion that they would like to interact. Burst smells can pave the way for a specific smell interaction.

SPECIFIC: A specific smell only occurs when a user deliberately interacts with an asset with the INTENTION of bringing it close to the nose and smelling it. Brain activity is very different when a user is "smelling with intention." Specific smells are usually the most potent and shortest duration and follow the logarithmic curve. Due to the high intensity of specific smells it is important to take special consideration that the smells rarely fall on the repulsive end of the "appeal" spectrum.

Figure 23:
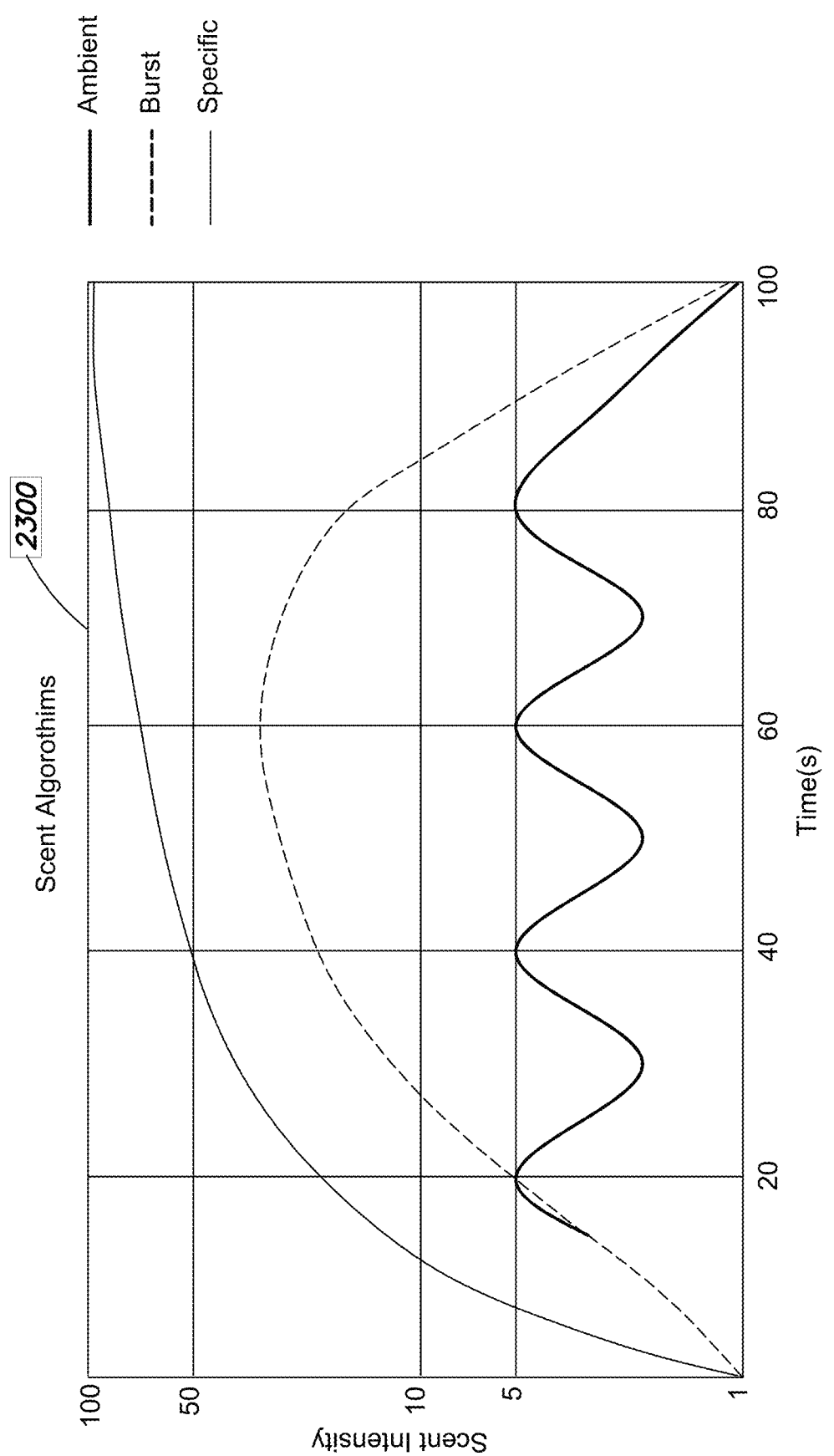
FIG. 23 shows scent intensity with respect to time for various proximity algorithms according to some embodiments.

FIG. 23 shows a graph 2300 of scent intensity with respect to time for various proximity algorithms. As shown in FIG. 23, each proximity algorithm mimics the way we naturally perceive odors and are self-adjusting based on proximity to the asset. An ambient proximity algorithm has a wave-like profile. A burst has a parabolic profile in which the intensity increases during a first time period and then decreases during a second time period after the first time period. A specific proximity algorithm has an increasing intensity where a rate of increase over a first time period (e.g., 0 to 20 seconds) is greater than a rate of increase of a second time period (e.g., 20 seconds to 60 seconds) subsequent to the first time period.

Intensity Protocol

MINIMUM DETECTABLE THRESHOLD (MDT): This value is measured in parts per million (ppm) and is based on biochemical studies as well as from controlled studies using organoleptic feedback. This number is generally below the level that is consciously detectable in humans but can still influence behavior due to the electrochemical signals produced when and odorant molecule stimulates the olfactory epithelium.

JBN (just barely noticeable): This value is the relationship between the ppm and subjective olfactory reporting. In certain cases, the ppm value may be the same as the MDT and on other occasions it may be much higher (user dependent). This is the moment when a user notices a very faint odor but is not able to identify it. As is the case with the MDT, the quantity of odor is not necessarily linked to its influence on behavior and emotion.

MINIMUM RECOGNIZABLE THRESHOLD: This value is the relationship between the ppm and the ability of the user to recognize that there is most certainly an odor and also identify what that odor is. The user will most likely not be able to identify the exact profile of the odor but rather recognize the family/category of the order (eg fruity/smoky/rancid) and give a subjective opinion on the attractiveness of the odor.

MAXIMUM THRESHOLD: Unlike sound and touch, humans' ability to perceive odor does not perpetually increase based on the amount of odorant the olfactory epithelium (OE) is exposed to. There is a maximum threshold at which point the user will cease to experience a higher intensity of odor no matter what the volume of odorant introduced to the OE. This number has been scientifically classified at between 10 and 50 times the MDT number which leaves a rather small window to work within. It should be noted that when the maximum threshold of an odorant is reached, it is generally unpleasant to the user and can cause irritation, pain and unwanted stimulation of the trigeminal nervous system.

In some embodiments and discussed in Appendix A, one or more parameters used to adjust how scents are being delivered to a human in an environment may be used to control one or more sent delivery mechanisms. As described further below, one or more aerosol generators may be used to generate one or more scents that can be perceived by human, such as within an AR/VR environment, within a controlled medical environment, and entertainment forum, or the like. In some embodiments, parameters relating to an intensity protocol and how the sent is delivered to a user over time may be used as control for operating one or more aerosol generators. In an AR/VR environment, a framework may be provided for associating odors to particular objects or places within the environment. Also, programming tools may be provided that defines how and at what distances an odor occurs within the environment. For example, there may be provided one or more functions that define how odors are released by aerosol generators associated with an AR or VR system. In one example including a computer game, thresholds, distances (e.g. radius definitions), and other parameters may be used to determine what distances odors can be perceived within an AR/VR environment. In one implementation, depending on a location of a user within the AR/VR environment, the system may determine a distance from an element within the AR/VR environment, and render a scent based on that perceived distance and/or relative location of the user from the object. Scents may also be released according to various patterns, intesitiesintensities, and in different combinations, depending on one or more programming constructs. Such controls of scent within the environment may be coupled with other output, such as changes in an AR/VR display (e.g., a display of a puff of smoke, simmering of an apple pie, or other display element), haptic feedback, audio or some other output. To achieve such control capability, one or more software controls may be provided for programmers and/or systems to control the performance of one or more aerosol generators.

Olfactory Function Categories

Smell influences our behavior in many small ways but scientists agree that they can all be classified into 3 broad categories: Gustatory, Social & Environmental. The relationship is bidirectional meaning that odorants can illicit behavior and cognition within the 3 categories but we may also use cognitively and behaviorally seek out odorants to fulfill needs within the categories.

GUSTATORY: Our sense of smell is extremely fine tuned to give us information about what we eat and drink. Our noses can lead us great distances to find food and before it ever enters our mouth our retronasal olfaction can tell us how nourishing and safe it is to eat. Once in the mouth, retronasal olfaction kicks in and we receive even more information about the composition of the food and our body responds appropriately. Our retronasal works almost like a failsafe to ensure if we encounter any questionable odor while chewing we can still spit out the food and avoid ingesting any microbes or dangerous chemicals.

SOCIAL: from physical and sexual attraction to family and community bonds olfaction plays a large role. Although pheromones have no noticeable smell of their own, they are still strong chemical indicators and can have a powerful effect on cognition and behavior.

ENVIRONMENTAL: The smells around us paint a picture that our eyes and ears cannot do on their own. By recognizing odorants in the air at concentrations sometimes as low as a single part per billion we can instantly assess dangerous or favorable environmental conditions and react appropriately.

Glossary of Terms for Architecture of Scent

VOC: Volatile Organic Compound

ODORANT: the term for VOC that triggers an electrochemical signal in the olfactory epithelium ODOR: the term for the sensation experienced when an odorant triggers an electrochemical signal in the olfactory epithelium FAMILY: odorant families are determined by the common molecular makeup of VOC groups (ege.g. contains hexane)

ODOR DESCRIPTION: these are subjective qualities that we generally associate with this odor family ORGANOLEPTIC: in general, having to do with the sense organs. For OVR purposes, the objective impression of a human when exposed to an odor DIFFUSIVE STRENGTH: objective calculation by combining the molecular weight of the VOCs and their vapor pressure at room temperature. Vapor pressure is calculated by the tendency of a VOC to "Evaporate" within standard temperatures at 1 atmospheric pressure.

OVERALL IMPACT: a function of diffusive strength and organoleptic sensitivity. It can be changed by adjusting one or both or by the degree of interaction the subject has with their surroundings (passive vs active)

ODOR DETECTION THRESHOLD: the minimum ppm quantity of an odorant material that stimulates the olfactory epithelium enough to trigger a conscious reaction. Measured as just barely noticeable (JBN) or conscious.

ODOR RECOGNITION THRESHOLD: the minimum ppm of an odorant material that is recognizable without prompting MASS MEDIAN AERODYNAMIC DIAMETER (MMAD): this is the average diameter of the particle size released by the device.

SPHERE OF INFLUENCE: this is the area around an in-game asset that will trigger the scent algorithm to activate.

INTERIOR/EXTERIOR DIAMETER: protocols within a sphere of influence that change the scent algorithm from one to another.

OLFACTORY FATIGUE (also referred to as "adaptation"): reduction in the sensitivity to odors inversely proportional to time exposed. The longer we are exposed, the less we perceive the smell TRIGEMINAL NERVE: the system of nerves that sense/respond to temperature CHEMOSENSORY: those senses such as smell and taste that translate molecular information into experience and behavior Example Implementations One example use of such a device according to various embodiments includes aerosol generation of scented liquids (such as for an AR/VR application described in an example application), but it can also be for turning any liquid (e.g., aqueous and non-aqueous) into a mist.

In particular, the device is used to atomize scented material, i.e., the ability to turn scented liquids into mist using vibration and micro-pores to allow the scent permeate in the air in specific quantities.

In other examples, the device may be used to atomize media such as liquid forms of cannabis into aerosol for inhalation: For instance, liquid forms of cannabis or cbd oils, waters or other aqueous solutions may be atomized and inhaled by users. Other media that may be used could include emulsions, solutions, mixtures, and inclusions. In such a case, the generator device may be part of a larger delivery mechanism (e.g., an e-cigarette, vaporizer, or other device) that allows users to inhale atomized liquids or other media types.

In some other applications, the device may be used for dispersing medical liquids (e.g., dispersing certain medicines in an atomized form for inhalation using conventional VMT technology. For instance, VMT devices used in nebulizers could be adapted using some of the embodiments described herein for that purpose.

Some other applications include:

Gel to liquid conversion—Certain theoretic gels have attributes where vibration turns them from a gel into a liquid which would allow for atomization through the device. This could be used primarily to do gel coatings as after vibration, the liquid would coalesce back into a gel.

Volatile liquid atomization (e.g., for alcohol, ethanol, gasoline, Benzine)—For instance, it may be beneficial to able to atomize various less common liquids for reasons like combustion engines.

Water humidification

In some embodiments, the size specification for the device may be relatively small, especially in applications where multiple devices may be used in parallel, such as within a larger device. Other applications (such as an e-cigarette application), the permitted dimension and/or may be limited to a relatively small form factor. Other applications may use a larger form factor, such as a large mist "cannon" that could be used to vaporize large amounts of water or scent or used as part of an engine.

One implementation includes a tube having a rectangular or square in shape. In some conventional piezo elements, they may use a pinching/squeezing mechanism to deliver liquids, however, in some embodiments as disclosed herein, a medium (e.g., a liquid) is aerosolized is via perpendicular acoustical waves induced by a piezo element.

In some implementations, there are a few ways that the medium can come into contact with the plate.

Free in housing—The liquid is just free in the tube and capped at the end opposite the aperture plate end to seal inside. The vibration pattern forces the liquid in contact with the plate.

Wick—A wick is placed in the tube and capped in with the liquid to force the correct capillary action to move the liquid to plate in conjunction with the vibration. In some embodiments, the wick may be shaped to fill the area within the tube (e.g., a rectangular, tubular, or square shape). In some implementations, the wick element may be a replaceable item, and may be accessible to be replaced. The wick may also be part of or coupled to a reservoir that holds liquid to be dispersed. The wick may be, in some embodiments, bidirectional or unidirectional wicking material made out of, for example, natural fibers and/or synthetic fibers including cotton, polyethylene, nylon, metal, graphene, among others.

Cartridge—A cartridge of custom design is inserted into the back to the tube with a connection point to the tube and plate. The cartridge may, or may not, use a wick or material that has a wicking property.

It should be appreciated that there are other applications of this technology and the invention is not limited to the examples provided herein. For example, some embodiments may be used in general entertainment, which could be movies or other experiences. Additionally, some embodiments may be applied to areas such as travel, business, education/training, telepresence, and meditation.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A system for generating odor impressions for a user, the system comprising:
    at least one processor;
    at least one non-transitory computer-readable storage medium storing instructions that, when executed by the at least one processor, cause the at least one processor to:
        generate an odorant component comprising virtual geometry with one or more dimensions in a computer-generated environment of the user;
        determine a plurality of values indicating intensities of a plurality of odorants based on the odorant component; and
        generate the odor impression for the user using the plurality of values indicating the intensities of the plurality of odorants.

2. The system of claim 1, wherein the plurality of values comprises concentrations and/or quantities of the plurality of odorants.

3. The system of claim 1, wherein generating the odor impression for the user using the plurality of values indicating the intensities of the plurality of odorants comprises mixing at least some of the plurality of odorants to generate the odor impression.

4. The system of claim 1, determining the plurality of values indicating the intensities of the plurality of odorants comprise:
    a first plurality of values indicating intensities of the plurality of odorants for a first time; and
    a second plurality of values indicating intensities of the plurality of odorants for a second time, wherein the second plurality of values is different from the first plurality of values.

5. The system of claim 1, wherein the instructions further cause the at least one processor to maintain a constant intensity of the plurality of odorants for a period of time.

6. The system of claim 1, wherein the virtual geometry is invisible to the user in the computer-generated environment.

7. The system of claim 1, wherein determining the plurality of values indicating the intensities of the plurality of odorants based on the odorant component comprises:
    determining one or more dimensions of the virtual geometry; and
    determining the plurality of values indicating the intensities of the plurality of odorants based on the one or more dimensions of the virtual geometry.

8. The system of claim 1, wherein determining the plurality of values indicating intensities of the plurality of odorants comprises:
    using a function associated with the odorant component to determine a scalar; and
    determining at least one of the plurality of values based on the scalar.

9. The system of claim 1, wherein determining the plurality of values indicating the intensities of the plurality of odorants based on the odorant component comprises:
    determining a location of the user in the computer-generated environment relative to a scent generating asset; and
    determining at least one of the plurality of values based on the location of the user in the computer-generated environment relative to the scent generating asset.

10. The system of claim 1, wherein determining the plurality of values indicating the intensities of the plurality of odorants based on the odorant component comprises:
    determining a measure of proximity of the user to a scent-generating asset in the computer-generated environment; and
    determining at least one of the plurality of values based on the measure of proximity of the user to the scent-generating asset in the computer-generated environment.

11. The system of claim 1, further comprising a plurality of vessels containing the plurality of odorants, wherein generating the odor impression comprises:
    controlling release of the plurality of odorants from the plurality of vessels based on the plurality of values indicating the intensities of the plurality of odorants.

12. The system of claim 1, wherein the computer-generated environment comprises an environment of an extended reality (XR) system, a multimedia system, an entertainment system, a fragrance delivery system, a reactive chemistry system, an advertising system, a medicine delivery system, and/or a skin care system.

13. The system of claim 1, wherein determining the plurality of values indicating the intensities of the plurality of odorants based on the odorant component comprises:
    generating an alphanumeric string associated with a scent; and
    determining the plurality of values indicating the intensities of the plurality of odorants based on the alphanumeric string.

14. A method for generating odor impressions for a user, the method comprising:
    using at least one processor to perform:
        generating an odorant component comprising virtual geometry with one or more dimensions in a computer-generated environment of the user;
        determining a plurality of values indicating intensities of a plurality of odorants based on the odorant component; and
        generating the odor impression for the user using the plurality of values indicating the intensities of the plurality of odorants.

15. The method of claim 14, wherein the plurality of values comprise concentrations and/or quantities of the plurality of odorants.

16. The method of claim 14, wherein generating the odor impression for the user using the plurality of values indicating the intensities of the plurality of odorants comprises mixing at least some of the plurality of odorants to generate the odor impression.

17. The method of claim 14, wherein determining the plurality of values indicating the intensities of the plurality of odorants comprises:
   determining a first plurality of values indicating intensities of the plurality of odorants for a first time; and
   determining a second plurality of values indicating intensities of the plurality of odorants for a second time, wherein the second plurality of values is different from the first plurality of values.

18. The method of claim 14, wherein determining the plurality of values indicating the intensities of the plurality of odorants based on the odorant component comprises:
   determining one or more dimensions of the virtual geometry; and
   determining the plurality of values indicating the intensities of the plurality of odorants based on the one or more dimensions of the virtual geometry.

19. The method of claim 14, wherein determining the plurality of values indicating the intensities of the plurality of odorants based on the odorant component comprises:
   determining a location of the user in the computer-generated environment relative to a scent generating asset; and
   determining at least one of the plurality of values based on the location of the user in the computer-generated environment relative to the scent generating asset.

20. The method of claim 14, wherein determining the plurality of values indicating the intensities of the plurality of odorants based on the odorant component comprises:
   determining a measure of proximity of the user to a scent-generating asset in the computer-generated environment; and
   determining at least one of the plurality of values based on the measure of proximity of the user to the scent-generating asset in the computer-generated environment.

21. The method of claim 14, wherein determining the plurality of values indicating the intensities of the plurality of odorants based on the odorant component comprises:
   generating an alphanumeric string associated with a scent; and
   determining the plurality of values indicating the intensities of the plurality of odorants based on the alphanumeric string.

* * * * *